(12) United States Patent
Verkhusha et al.

(10) Patent No.: US 11,008,369 B2
(45) Date of Patent: May 18, 2021

(54) BRIGHT MONOMERIC NEAR-INFRARED FLUORESCENT PROTEINS ENGINEERED FROM BACTERIAL PHYTOCHROMES AND METHODS FOR MAKING SAME

(71) Applicant: Albert Einstein College of Medicine, Bronx, NY (US)

(72) Inventors: Vladislav V. Verkhusha, Bronx, NY (US); Daria M. Shcherbakova, Bronx, NY (US); Mikhail Baloban, Saint-Léonard (CA)

(73) Assignee: Albert Einstein College of Medicine, Bronx, NY (US)

(*) Notice: Subject to any disclaimer, the term of this patent is extended or adjusted under 35 U.S.C. 154(b) by 0 days.

(21) Appl. No.: 16/567,733

(22) Filed: Sep. 11, 2019

(65) Prior Publication Data
US 2020/0079822 A1    Mar. 12, 2020

Related U.S. Application Data

(62) Division of application No. 15/497,667, filed on Apr. 26, 2017, now Pat. No. 10,442,839.

(60) Provisional application No. 62/328,496, filed on Apr. 27, 2016.

(51) Int. Cl.
*C07K 14/195*    (2006.01)

(52) U.S. Cl.
CPC ........ *C07K 14/195* (2013.01); *C07K 2319/00* (2013.01); *C07K 2319/50* (2013.01); *C07K 2319/60* (2013.01)

(58) Field of Classification Search
CPC ............ C07K 2319/00; C07K 2319/60; C07K 2319/50; C07K 14/195
See application file for complete search history.

(56) References Cited

U.S. PATENT DOCUMENTS

| 8,735,555 B2 | 5/2014 | Lagarias et al. |
| 10,442,839 B2* | 10/2019 | Verkhusha ........... C07K 14/195 |
| 2015/0353609 A1 | 12/2015 | Yu et al. |

OTHER PUBLICATIONS

Davidson et al., Engineered fluorescent proteins: innovations and applications. Nat. Methods., 2009, vol. 6(10): 713-717. (Year: 2009).*
Shcherbo et al., Near-infrared flourescent proteins. Nat. Methods., 2010, vol. 7(10): 827-829. (Year: 2010).*
Baloban et al., "Designing brighter near-infrared fluorescent proteins: insights from structural and biochemical studies," Chem. Sci., May 4, 2017, vol. 8, pp. 4546-4557, (Year: 2017).
Shcherbakova et al., "Bright monomeric near-infrared fluorescent proteins as tags and biosensors for multiscale imaging," Nature Communications, Aug. 19, 2016, vol. 7, pp. 1-12, (Year: 2016).
Shcherbakova et al., "Molecular basis of spectral diversity in near-infrared phytochrome-based fluorescent proteins," Chem. Biol., Nov. 19, 2015, vol. 22, pp. 1540-1551, (Year: 2015).

* cited by examiner

*Primary Examiner* — Ganapathirama Raghu
(74) *Attorney, Agent, or Firm* — Amster, Rothstein & Ebenstein LLP

(57) ABSTRACT

Nucleic acid molecules encoding monomeric near-infrared fluorescent proteins, variants and derivatives thereof are provided, as well as proteins and peptides encoded by these nucleic acids. Also provided are proteins that are substantially similar to, or derivatives, homologues, or mutants of, the above-referenced specific proteins. Also provided are fragments of the nucleic acids and the peptides encoded thereby, specifically split fluorescent proteins. In addition, host-cells, stable cell lines and transgenic organisms comprising above-referenced nucleic acid molecules are provided. The invention also refers to methods of making and using monomeric fluorescent proteins derived from bacterial phytochromes. The subject protein and nucleic acid compositions find use in a variety of different applications and methods, particularly for labeling of biomolecules, cells or cell organelles, and for detecting protein-protein interactions. Finally, kits for use in such methods and applications are provided.

7 Claims, 15 Drawing Sheets
(14 of 15 Drawing Sheet(s) Filed in Color)

Specification includes a Sequence Listing.

```
miRFP670v1        MVAGHASGSPAFGTASHSNSEHEEIHLAGSIQPHGALLVVSEHDHRVIQASANAAEFLN
miRFP670          MVAGHASGSPAFGTASHSNCEHEEIHLAGSIQPHGALLVVSEHDHRVIQASANAAEFLN
miRFP703          MVAGHASGSPAFGTASHSNCEHEEIHLAGSIQPHGALLVVSEHDHRVIQASANAAEFLN
miRFP709          MVAGHASGSPAFGTASHSNCEHEEIHLAGSIQPHGALLVVSEHDHRVIQASANAAEFLN
RpBphP1(PAS-GAF)  MVAGHASGSPAFGTADLSNCEREEIHLAGSIQPHGALLVVSEPDHRIIQASANAAEFLN miRFP670v1        LGSVLGVPLAEIDGDLLIKILPHLDPTAEGMPVAVRCRIGNPSTEYCGLMHRPPEGGLIIE
miRFP670          LGSVLGVPLAEIDGDLLIKILPHLDPTAEGMPVAVRCRIGNPSTEYCGLMHRPPEGGLIIE
miRFP703          LGSVLGVPLAEIDGDLLIKILPHLDPTAEGMPVAVRCRIGNPSTEYCGLMHRPPEGGLIIE
miRFP709          LGSVLGVPLAEIDGDLLIKILPHLDPTAEGMPVAVRCRIGNPSTEYCGLMHRPPEGGLIIE
RpBphP1(PAS-GAF)  LGSVLGVPLAEIDGDLLIKILPHLDPTAEGMPVAVRCRIGNPSTEYDGLMHRPPEGGLIIE miRFP670v1        LERAGPSIDLSGTLAPALERIRTAGSLRALCDDTVLLFQQCTGYDRVMVYRFDEQGHGE
miRFP670          LE      SIDLSGTLAPALERIRTAGSLRALCDDTVLLFQQCTGYDRVMVYRFDEQGHGE
miRFP703          LERAGPSIDLSGTLAPALERIRTAGSLRALCDDTVLLFQQCTGYDRVMVYRFDEQGHGE
miRFP709          LE      SIDLSGTLAPALERIRTAGSLRALCDDTVLLFQQCTGYDRVMVYRFDEQGHGE
RpBphP1(PAS-GAF)  LERAGPPIDLSGTLAPALERIRTAGSLRALCDDTALLFQQCTGYDRVMVYRFDEQGHGE miRFP670v1        VFSECHVPGLESYFGNRYPSSVVPQMARQLYVRQRVRVLVDVTYQPVPLEPRLSPLTGR
miRFP670          VFSECHVPGLESYFGNRYPSSVVPQMARQLYVRQRVRVLVDVTYQPVPLEPRLSPLTGR
miRFP703          VFSECHVPGLESYFGNRYPSSLVPQMARQLYVRQRVRVLVDVTYQPVPLEPRLSPLTGR
miRFP709          VFSECHVPGLESYFGNRYPSSFIPQMARQLYVRQRVRVLVDVTYQPVPLEPRLSPLTGR
RpBphP1(PAS-GAF)  VFSERHVPGLESYFGNRYPSSDIPQMARRLYERQRVRVLVDVSYQPVPLEPRLSPLTGR miRFP670v1        DLDMSGCFLRSMSPCHLQFLKDMGVRATLAVSLVVGGKLWGLVVCHHYLPRFIRFELR
miRFP670          DLDMSGCFLRSMSPCHLQFLKDMGVRATLAVSLVVGGKLWGLVVCHHYLPRFIRFELR
miRFP703          DLDMSGCFLRSMSPIHLQFLKDMGVRATLAVSLVVGGKLWGLVVCHHYLPRFIRFELR
miRFP709          DLDMSGCFLRSMSPIHLQFLKDMGVRATLAVSLVVGGKLWGLVVCHHYLPRFIRFELR
RpBphP1(PAS-GAF)  DLDMSGCFLRSMSPIHLQYLKNMGVRATLVVSLVVGGKLWGLVACHHYLPRFIHFELR miRFP670v1        AICKRLAERIATRITALES
miRFP670          AICKRLAERIATRITALES
miRFP703          AICKRLAERIATRITALES
miRFP709          AICKRLAERIATRITALES
RpBphP1(PAS-GAF)  AICELLAEAIATRITALES
```

Fig. 8.

```
                           1                                                50
RpBphP1 (PAS-GAF)    (1)   MVAGHASGSPAFGTADLSNCEREEIHLAGSIQPHGALLVVSEPDHRIIQA
    miRFP670v1       (1)   MVAGHASGSPAFGTASHSNSEHEEIHLAGSIQPHGALLVVSEHDHRVIQA
      miRFP670       (1)   MVAGHASGSPAFGTASHSNCEHEEIHLAGSIQPHGALLVVSEHDHRVIQA
      miRFP703       (1)   MVAGHASGSPAFGTASHSNCEHEEIHLAGSIQPHGALLVVSEHDHRVIQA
      miRFP709       (1)   MVAGHASGSPAFGTASHSNCEHEEIHLAGSIQPHGALLVVSEHDHRVIQA

RpBphP6 (PAS-GAF)    (1)   ----------MPRKVDLTSCDREPIHIPGSIQPCGCLLACDAQAVRITRI
     miRFP670-2      (1)   ----------MARKVDLTSCDREPIHIPGSIQPCGCLLACDAQAVRITRI
       miRFP702      (1)   ----------MARKVDLTSCDREPIHIPGSIQPCGCLLACDAQAVRITRI

RpBphP2 (PAS-GAF)    (1)   -----MTEGSVARQPDLSTCDDEPIHIPGAIQPHGLLLALAADMTIVAGS
       miRFP682      (1)   -----MAEGSVARQPDLLTCDDEPIHIPGAIQPHGLLLALAADMTIVAGS
       miRFP713      (1)   -----MAEGSVARQPDLLTCDDEPIHIPGAIQPHGLLLALAADMTIVAGS
       miRFP720      (1)   -----MAEGSVARQPDLLTCDDEPIHIPGAIQPHGLLLALAADMTIVAGS 51                                               100
RpBphP1 (PAS-GAF)   (51)   SANAAEFLNLGSVLG----VPLAEIDGDLLIKILPHLDPTAEGMPVAVRC
    miRFP670v1      (51)   SANAAEFLNLGSVLG----VPLAEIDGDLLIKILPHLDPTAEGMPVAVRC
      miRFP670      (51)   SANAAEFLNLGSVLG----VPLAEIDGDLLIKILPHLDPTAEGMPVAVRC
      miRFP703      (51)   SANAAEFLNLGSVLG----VPLAEIDGDLLIKILPHLDPTAEGMPVAVRC
      miRFP709      (51)   SANAAEFLNLGSVLG----VPLAEIDGDLLIKILPHLDPTAEGMPVAVRC

RpBphP6 (PAS-GAF)   (41)   SENAGAFFGRETPRVGELLADYFGETEAHALRNALAQSSDPKRPALIFGW
     miRFP670-2     (41)   TENAGAFFGRETPRVGELLADYFGETEAHALRNALAQSSDPKRPALIFGW
       miRFP702     (41)   TENAGAFFGRETPRVGELLADYFGETEAHALRNALAQSSDPKRPALIFGW

RpBphP2 (PAS-GAF)   (46)   DNLPELTGLAIGALIGRSAADVFDSETHNRLTIALAEPGAAVGAPIAVGF
       miRFP682     (46)   DNLPELTGLAIGALIGRSAADVFDSETHNRLTIALAEPGAAVGAPITVGF
       miRFP713     (46)   DNLPELTGLAIGALIGRSAADVFDSETHNRLTIALAEPGAAVGAPITVGF
       miRFP720     (46)   DNLPELTGLAIGALIGRSAADVFDSETHNRLTIALAEPGAAVGAPITVGF 101                                              150
RpBphP1 (PAS-GAF)   (97)   RIGNPSTEYDGLMHRPPEGGLIIELER----AGPPIDLSGTLAPALERIR
    miRFP670v1      (97)   RIGNPSTEYCGLMHRPPEGGLIIELER----AGPSIDLSGTLAPALERIR
      miRFP670      (97)   RIGNPSTEYCGLMHRPPEGGLIIELER----AGPSIDLSGTLAPALERIR
      miRFP703      (97)   RIGNPSTEYCGLMHRPPEGGLIIELER----AGPSIDLSGTLAPALERIR
      miRFP709      (97)   RIGNPSTEYCGLMHRPPEGGLIIELER----AGPSIDLSGTLAPALERIR

RpBphP6 (PAS-GAF)   (91)   RDGLTGRTFDISLHRHD-GTSIVEFEP--AAADQADNPLRLTRQIIARTK
     miRFP670-2     (91)   RDGLTGRTFDISLHRHD-GTSIIEFEP--AAAEQADNPLRLTRQIIARTK
       miRFP702     (91)   RDGLTGRTFDISLHRHD-GTSIIEFEP--AAAEQADNPLRLTRQIIARTK

RpBphP2 (PAS-GAF)   (96)   TMRKDAG-FVGSWHRHD-QLVFLELEPPQRDVAEPQAFFRRTNSAIRRLQ
       miRFP682     (96)   TMRKDAG-FIGSWHRHD-QLIFLELEPPQRDVAEPQAFFRRTNSAIRRLQ
       miRFP713     (96)   TMRKDAG-FIGSWHRHD-QLIFLELEPPQRDVAEPQAFFRRTNSAIRRLQ
       miRFP720     (96)   TMRKDAG-FIGSWHRHD-QLIFLELEPPQRDVAEPQAFFRRTNSAIRRLQ 151                                              200
RpBphP1 (PAS-GAF)  (143)   TAGSLRALCDDTALLFQQCTGYDRVMVYRFDEQGHGEVFSERHVPGLESY
    miRFP670v1     (143)   TAGSLRALCDDTVLLFQQCTGYDRVMVYRFDEQGHGLVFSECHVPGLESY
      miRFP670     (143)   TAGSLRALCDDTVLLFQQCTGYDRVMVYRFDEQGHGLVFSECHVPGLESY
      miRFP703     (143)   TAGSLRALCDDTVLLFQQCTGYDRVMVYRFDEQGHGLVFSECHVPGLESY
      miRFP709     (143)   TAGSLRALCDDTVLLFQQCTGYDRVMVYRFDEQGHGLVFSECHVPGLESY
```

Fig. 9A

```
RpBphP6 (PAS-GAF) (138) ELKSLEEMAARVPRYLQAMLGYHRVMMYRFADDGSGKVIGEAKRSDLESF
     miRFP670-2 (138) ELKSLEEMAARVPRYLQAMLGYHRVMLYRFADDGSGMVIGEAKRSDLESF
         miRFP702 (138) ELKSLEEMAARVPRYLQAMLGYHRVMLYRFADDGSGKVIGEAKRSDLESF

RpBphP1 (PAS-GAF) (144) AAETLESACAAAAQEVREITGFDRVMIYRFASDFSGEVIAEDRCAEVESY
         miRFP682 (144) AAETLESACAAAAQEVRKITGFDRVMIYRFASDFSGVVIAEDRCAEVESK
         miRFP713 (144) AAETLESACAAAAQEVRKITGFDRVMIYRFASDFSGEVIAEDRCAEVESK
         miRFP720 (144) AAETLESACAAAAQEVRKITGFDRVMIYRFASDFSGSVIAEDRCAEVESK 201                                              250
RpBphP1 (PAS-GAF) (193) FGNRYPSSDIPQMARRLYERQRVRVLVDVSYQPVPLEPRLSPLTGRDLDM
        miRFP670v1 (193) FGNRYPSSTVPQMARQLYVRQRVRVLVDVTYQPVPLEPRLSPLTGRDLDM
           miRFP670 (193) FGNRYPSSTVPQMARQLYVRQRVRVLVDVTYQPVPLEPRLSPLTGRDLDM
           miRFP703 (193) FGNRYPSSLVPQMARQLYVRQRVRVLVDVTYQPVPLEPRLSPLTGRDLDM
           miRFP709 (193) FGNRYPSSFIPQMARQLYVRQRVRVLVDVTYQPVPLEPRLSPLTGRDLDM

RpBphP6 (PAS-GAF) (188) LGQHFPASDIPQQARLLYLKNAIRVISDSRGISSRIVPERD-ASGAALDL
     miRFP670-2 (188) LGQHFPASLVPQQARLLYLKNAIRVVSDSRGISSRIVPEHD-ASGAALDL
         miRFP702 (188) LGQHFPASLVPQQARLLYLKNAIRVVSDSRGISSRIVPEHD-ASGAALDL

RpBphP2 (PAS-GAF) (194) LGLHFPASDIPAQARRLYTINPVRIIPDINYRPVPVTPDLNPVTGRPIDL
         miRFP682 (194) LGLHYPASAVPAQARRLYTINPVRIIPDINYRPVPVTPDLNPVTGRPIDL
         miRFP713 (194) LGLHYPASTVPAQARRLYTINPVRIIPDINYRPVPVTPDLNPVTGRPIDL
         miRFP720 (194) LGLHYPASFIPAQARRLYTINPVRIIPDINYRPVPVTPDLNPVTGRPIDL 251                                              300
RpBphP1 (PAS-GAF) (243) SGCFLRSMSPIHLQYLKNMGVRATLVVSLVVGGKLWGLVACHHYLPRFMH
        miRFP670v1 (243) SGCFLRSMSPCHLQFLKDMGVRATLAVSLVVGGKLWGLVVCHHYLPRFIR
           miRFP670 (243) SGCFLRSMSPCHLQFLKDMGVRATLAVSLVVGGKLWGLVVCHHYLPRFIR
           miRFP703 (243) SGCFLRSMSPIHLQFLKDMGVRATLAVSLVVGGKLWGLVVCHHYLPRFIR
           miRFP709 (243) SGCFLRSMSPIHLQFLKDMGVRATLAVSLVVGGKLWGLVVCHHYLPRFIR

RpBphP6 (PAS-GAF) (237) SFAHLRSVSPIHLEYLRNMGVSASMSLSIIIDGTLWGLIACHHYEPRAVP
     miRFP670-2 (237) SFAHLRSISPCHLEFLRNMGVSASMSLSIIIDGTLWGLIICHHYEPRAVP
         miRFP702 (237) SFAHLRSISPIHLEFLRNMGVSASMSLSIIIDGTLWGLIICHHYEPRAVP

RpBphP2 (PAS-GAF) (244) SFAILRSVSPVHLEYMRNIGMHGTMSISILRGERLWGLIACHHRKPNYVD
         miRFP682 (244) SFAILRSVSPCHLEFMRNIGMHGTMSISILRGERLWGLIVCHHRTPYYVD
         miRFP713 (244) SFAILRSVSPVHLEFMRNIGMHGTMSISILRGERLWGLIVCHHRTPYYVD
         miRFP720 (244) SFAILRSVSPNHLEFMRNIGMHGTMSISILRGERLWGLIVCHHRTPYYVD
                         301              325
RpBphP1 (PAS-GAF) (293) FELRAICELLAEAIATRITALES--
        miRFP670v1 (293) FELRAICKRLAERIATRITALES--
           miRFP670 (293) FELRAICKRLAERIATRITALES--
           miRFP703 (293) FELRAICKRLAERIATRITALES--
           miRFP709 (293) FELRAICKRLAERIATRITALES--

RpBphP6 (PAS-GAF) (287) MAQRVAAEMFADFFSLHFTAAHHQR
     miRFP670-2 (287) MAQRVAAKRFAERLSTHFTAAHHQR
         miRFP702 (287) MAQRVAAKRFAERLSTHFTAAHHQR

RpBphP2 (PAS-GAF) (294) LDGRQACELVAQVLAWQIGVMEE--
         miRFP682 (294) LDGRQACKRVAERLATQIGVMEE--
         miRFP713 (294) LDGRQACKRVAERLATQIGVMEE--
         miRFP720 (294) LDGRQACKRVAERLATQIGVMEE-
Fig. 9B
``` a

```
                    301                       325
RpBphP1             FELRAICELLAEAIATRITALES
miRFP670            FELRAICRLAERIATRITALES iRFP720             LDGRQACELVAQVLANQIGVMEE
miRFP720            LDGRQACRRVAERLARQIGVMEE iRFP670             MAQRVAAEMFADFLSLHFTAAHHQR
miRFP670-2          MAQRVAARRFAERLSTHFTAAHHQR
``` b

```
DrBphP              PDLRTTLEYLGRLLSLQVQVKEA
IFP1.4              PDLRTTLERLGRRLSQQVQRKEA
IFP2.0              PDLRTTLEYLGRLLSLQVQRKEA
``` c

```
                    143           299                    321
DrBphP              AMFALESAP-    PDLRTTLEYLGRLLSLQVQVKEA
Wi-phy              AMSALESAP-    PDLRTTLEYLGRELSRQVQVKEA
```

Fig. 10A-10C.

BRIGHT MONOMERIC NEAR-INFRARED FLUORESCENT PROTEINS ENGINEERED FROM BACTERIAL PHYTOCHROMES AND METHODS FOR MAKING SAME

CROSS-REFERENCE TO RELATED APPLICATIONS

This application is a divisional of U.S. patent application Ser. No. 15/497,667, filed Apr. 26, 2017, (now U.S. Pat. No. 10,442,839, issued on Oct. 15, 2019), which claims benefit of U.S. Provisional Application No. 62/328,496, filed Apr. 27, 2016, the contents of each of which are incorporated herein by reference into the subject application.

STATEMENT OF GOVERNMENT SUPPORT

This invention was made with government support under grant GM108579 awarded by the US National Institutes of Health. The government has certain rights in the invention.

FIELD OF THE INVENTION

Fluorescent proteins and nucleic acids that encode monomeric fluorescent proteins derived from bacterial phytochromes are provided. Also provided are methods of making and using such fluorescent proteins, including reagents, devices and kits for use in these methods.

BACKGROUND OF THE INVENTION

Throughout this application various publications are referred to in parentheses. Full citations for these references may be found at the end of the specification. The disclosures of these publications, and all patents, patent application publications and books referred to herein, are hereby incorporated by reference in their entirety into the subject application to more fully describe the art to which the subject invention pertains.

Non-invasive in vivo imaging requires near-infrared (NIR) fluorescent probes. Recent development of genetically encoded fluorescent proteins (FPs) from bacterial phytochrome photoreceptors (BphPs) has significantly advanced deep-tissue and whole-body imaging (1). In contrast to far-red GFP-like FPs, BphP-derived FPs are excited and fluoresce close to or within an NIR tissue transparency "optical window" (~650-900 nm) where background autofluorescence is low, light scattering is reduced, and combined absorption of hemoglobin, melanin, and water is minimal (2).

NIR fluorescence of BphP-based FPs results from an incorporation of the most red-shifted natural chromophore, biliverdin IXα (hereafter BV) (1, 3, 4), that is similar to their parental BphPs (5, 6). Fortunately, BV is abundant in eukaryotes, including mammals, as an intermediate of heme degradation pathway to bilirubin (7, 8). In wild-type BphPs, light absorption results in BV isomerization and conformational changes of the protein backbone, leading to activation of an output effector domain. In engineered NIR FPs, the photoisomerization is blocked and the other non-radiative energy dissipation pathways are suppressed by truncation of BphPs to the chromophore-binding PAS-GAF domains and by introducing of amino acid substitutions in the chromophore immediate environment (1, 9).

Although BphP-based NIR FPs are now widely used in many areas of basic and translational research, including cancer studies, stem cell biology, neuroscience, and parasitology, these FPs are mainly serve as passive whole-cell labels for non-invasive in vivo imaging (5). So far these NIR FPs had the limited use in monitoring of active cellular processes in animals, such as activation of signaling cascades and protein-protein interactions (PPIs). A development of active NIR reporters and biosensors, which respond to cellular events and consequently change their fluorescence, has been hampered by a lack of bright monomeric NIR FPs as building blocks for these sensors. The monomeric NIR FPs are also required to label (tag) intracellular proteins. Currently available monomeric far-red GFP-like FPs, including mKate2 (10), TagRFP657 (11), mCardinal and mNeptune2.5 (12), are suboptimal for deep-tissue imaging because their excitation maxima do not exceed 611 nm.

Current BphP-based NIR FPs have limitations and cannot be used to label proteins and to build NIR biosensors. There are three characteristics of NIR FPs, which are crucial to consider for their applications (1). The first one is an effective brightness of NIR FP in mammalian cells, which depends on its molecular brightness, intracellular stability, efficiency of BV incorporation, and cell expression level. In contrast to GFP-like FPs, the effective brightness of BphP-based NIR FPs does not always correlate with their molecular brightness (1). Decreased cellular fluorescence of some NIR FPs results from a low specificity of BV binding and a competition between BV and other heme-derived compounds, including protoporphyrin IX, for binding to NIR FP apoproteins (13, 14). The second characteristic to consider is an oligomeric state of FPs. Only monomeric FPs can be used in protein fusions without interference with functionality of the tagged protein partner (15). The third characteristic is the spectral properties of NIR FPs. Spectrally distinct NIR FPs are required for biosensors and for multicolor NIR labeling.

Among the reported BphP-based FPs, five spectrally distinct NIR FPs, iRFP670, iRFP682, iRFP702, iRFP713 and iRFP720 (1, 4, 16) fully rely on endogenous BV and do not require its external supply or co-expression of heme oxygenase (HO). Therefore, these proteins can be used as easy as GFP-like FP by delivering a single gene to cells. Importantly, possible endogenous BV concentration variability does not influence performance of iRFPs. Indeed, iRFP713 fluorescence was observed in all tissues of two iRFP713-transgenic mouse lines (8). In both mouse lines, the iRFP713 fluorescence intensity was generally uniform in almost all organs and tissues, with slightly higher expression levels in liver, lungs, and pancreas. However, iRFPs are dimers and can mainly serve for labeling of organelles and whole cells.

The first monomeric BphP-based FP, IFP1.4 (3), is dim and do not fluoresce without a BV supply. Moreover, it forms dimers, as was found recently (17). Its brighter version IFP2.0(18) was also found to be dimeric (1, 17). Previously reported monomeric FPs, Wi-Phy (9) and IFP1.4rev (19), were characterized only in vitro (9, 19). Recently reported monomeric mIFP (17), which is the only one monomeric FP tested in cellular fusions, is dimmer than dimeric iRFPs and requires a supply of BV via co-expression of BV-producing enzyme, HO. Also, a lack of spectrally distinct versions of monomeric BphP-based FPs prevents two-color NIR protein labeling and a development of NIR reporters and biosensors.

Previously reported methods of NIR FP monomerization (3, 9, 18) resulted in significant loss of brightness in mammalian cells or were not efficient enough to prevent dimer formation at concentrations above 10 μM (more than 0.35 mg/ml for a typical BphP-based FP) (1, 17)

Thus, there is a need in the art for the development of bright monomeric spectrally distinct NIR FPs that find use in scientific applications without technical limitations due to oligomerization. There exists also a need for methods to produce such FPs.

Here we report a set of three bright spectrally distinct monomeric NIR FPs, called miRFPs, which fully rely on endogenous BV to fluoresce in mammalian cells and mammals. We demonstrate a use of miRFPs in a wide range of NIR protein tags, reporters and biosensors. First, we created a set of miRFP protein fusions and showed that they can be imaged using common diffraction-limited and super-resolution microscopy. Second, using miRFPs as scaffolds, we developed spectrally distinct monomeric bimolecular fluorescence complementation (BiFC) reporters for PPIs and for low-background RNA imaging. Third, we demonstrated a use of miRFPs to develop NIR reporters for signaling cascades and cell fate. Specifically, we designed NIR IkBa and NIR cell cycle reporters and showed that they perform well in applications across scales: from microscopy and flow cytometry to whole-body imaging.

Here we also report a method, which we applied to monomerize existing dimeric NIR FPs, termed iRFPs, without significant decrease in brightness in mammalian cells. The monomerized versions of these iRFPs were also named as miRFPs with the numbers corresponding to the emission maximum. The method can also be applied to monomerize other NIR FPs derived from BphPs.

The present invention satisfies the needs stated above and provides additional advantages. The present invention addresses the need for bright spectrally distinct genetically encoded monomeric near-infrared FPs, uses thereof, and methods to produce these FPs.

The present invention also provides NIR fluorescent reporters based on the engineered monomeric NIR FPs and uses thereof.

SUMMARY OF THE INVENTION

This invention provides mutants of a BphP, RpBphP1, from the bacterium *Rhodopseudomonas palustris*. Being expressed in any cell containing BV, these mutant BphPs spontaneously incorporate BV and become fluorescent in the NIR region. Notably, BV is abundant in mammalian tissues as an intermediate in heme metabolism. The present mutants are monomeric and the brightest variants among currently known monomeric BphP-derived NIR FPs. The mutants vary in their spectral properties that is important for their applications.

This invention provides an isolated protein comprising consecutive amino acid residues having the sequence set forth in miRFP670v1 (SEQ ID NO: 1), miRFP670 (SEQ ID NO:2), miRFP703 (SEQ ID NO:3), or miRFP709 (SEQ ID NO:4), or having 90% or greater identity to one of SEQ ID NO: 1, SEQ ID NO:2, SEQ ID NO:3, or SEQ ID NO:4.

This invention also provides an isolated nucleic acid encoding a protein comprising consecutive amino acid residues having the sequence set forth in miRFP670v1 (SEQ ID NO: 1), miRFP670 (SEQ ID NO:2), miRFP703 (SEQ ID NO:3), or miRFP709 (SEQ ID NO:4). This invention also provides an isolated nucleic acid encoding a protein comprising consecutive amino acid residues having 90% or greater identity to one of SEQ ID NO:1, SEQ ID NO:2, SEQ ID NO:3, or SEQ ID NO:4.

In another embodiment, the invention provides an isolated nucleic acid encoding a protein comprising, wherein the protein comprises at least one amino acid residue selected from the group consisting of S16, H17, C20, S20, H22, H43, C106, S127, V155, L179, C184, D201, T201, L201, F201, A201, I202, V202, C202, Q208, V211, I253, C253, D260, A268, V282, R292, K300, R301, and R305. Preferably, the protein comprises at one amino acid residue selected from the group consisting of D201, T201, L201, F201, A201, I202, V202, C202, I253, C253, K300, R301, and R305 of SEQ ID NOs: 1-4.

This invention also provides split fragments of FPs having the sequence set forth in miRFP670v1 (SEQ ID NO: 1), miRFP670 (SEQ ID NO:2), miRFP703 (SEQ ID NO:3), or miRFP709 (SEQ ID NO:4), or having 90% or greater identity to one of SEQ ID NO: 1, SEQ ID NO:2, SEQ ID NO:3, or SEQ ID NO:4. The two split fragments are not fluorescent individually, but form a functional fluorescent molecule when complemented. The split system for bimolecular fluorescence complementation assay is monomeric and provides lower background and higher complementation contrast than known dimeric NIR split systems. The split system comprises two split fragments that correspond to the PAS and the GAF domains of the FPs. Specifically for miRFP-related proteins, the PAS domain corresponds to the fragment comprising at least amino acid residues with positions at 16-120, preferably 1-125; the GAF domain corresponds to the fragment comprising at least amino acid residues with positions at 130-310, preferably 126-315. The amino acid positions correspond to SEQ ID NOs:1-4.

This invention provides an isolated protein comprising consecutive amino acid residues having the sequences of split parts reconstituting miRFP670v1 (SEQ ID NO: 1): miRFP-PAS1 (SEQ ID NO:6) and miRFP-GAF670 (SEQ ID NO:7), having the sequences of split parts reconstituting miRFP670 (SEQ ID NO:2): miRFP-PAS (SEQ ID NO:5) and miRFP-GAF670 (SEQ ID NO:7), having the sequences of split parts reconstituting miRFP703 (SEQ ID NO:3): miRFP-PAS (SEQ ID NO:5) and miRFP-GAF703 (SEQ ID NO:8), or having the sequences of split parts reconstituting miRFP709 (SEQ ID NO:4): miRFP-PAS (SEQ ID NO:5) and miRFP-GAF709 (SEQ ID NO:9), or having 90% or greater identity to one of SEQ ID NO:5, SEQ ID NO:6, SEQ ID NO:7, SEQ ID NO:8 or SEQ ID NO:9.

This invention also provides an isolated nucleic acid encoding a protein comprising consecutive amino acid residues having the sequence set forth in miRFP-PAS (SEQ ID NO:5), miRFP-PAS1 (SEQ ID NO:6), miRFP-GAF670 (SEQ ID NO:7), miRFP-GAF703 (SEQ ID NO:8), miRFP-GAF709 (SEQ ID NO:9). This invention also provides an isolated nucleic acid encoding a protein comprising consecutive amino acid residues having 90% or greater identity to one of SEQ ID NO:5, SEQ ID NO:6, SEQ ID NO:7, SEQ ID NO:8 or SEQ ID NO:9.

In another embodiment, the invention provides a method for the generation of monomeric variants of a FP derived from a BphP that has propensity to dimerize, comprising the mutagenesis of at least four amino acid residues in the FP to produce a monomeric FP variant.

The mutagenesis used in the present method can be site directed mutagenesis. The results of this mutagenesis can produce protein variants that have a propensity to form monomers.

In some aspects, the invention concerns FPs derived from BphP proteins having a reduced propensity to dimerize, comprising at least four mutations within the C-terminal amino acid sequence that reduces or eliminates the ability of the FP to dimerize. The FPs are preferably variants of dimeric iRFPs and miRFPs of SEQ ID NOs: 1-4, and 11-15, but is by no means so limited. In some embodiments, the invention concerns miRFPs comprising at least four amino acid substitutions at the C-terminus corresponding to amino acid positions 300, 301, 304, 305, 308 (numbering is according to RpBphP1, i.e. SEQ ID NO: 10, the corresponding positions in other FPs are derived from alignment with RpBphP1) that reduces or eliminates the degree of oligomerization of said FPs.

Aspects of this invention specifically include monomeric variants of other FPs in addition variants of iRFPs and miRFPs (SEQ ID NOs: 1-4, and 11-15), such as FPs derived from other BphPs. For example, NIR FPs derived from DrBphP find equal use with the invention. Furthermore, FPs that normally have the propensity to form oligomers find equal use with the invention.

In a particular embodiment, the FPs are variants derived from iRFPs and miRFP having a reduced propensity to oligomerize are prepared by replacing at least four amino acid residues to negatively or positively charged residues (D, E, K, R) in positions corresponding to 300, 301, 304, 305, 308 (numbering is according to RpBphP1, i.e. SEQ ID NO: 10, the corresponding positions in other FPs are derived from alignment with RpBphP1, the example alignment is provided in FIG. 9).

In one aspect, the invention provides example FPs, including but not limited to variants of iRFPs and miRFPs (SEQ ID NOs: 1-4, and 11-15), comprising amino acid substitutions relative to the respective starting sequences, where the substitutions confer the monomeric state. These amino acid positions can reside at positions homologous to 300, 301, 304, 305, 308 (numbering is according to RpBphP1, i.e. SEQ ID NO: 10, the corresponding positions in other FPs are derived from alignment with RpBphP1) and are limited to substitution with positively or negatively charged residues (D, E, K, R).

This invention also provides an isolated protein comprising consecutive amino acid residues having the sequence set forth in miRFP670-2 (SEQ ID NO: 11), miRFP702 (SEQ ID NO:12), miRFP682 (SEQ ID NO:13), miRFP713 (SEQ ID NO:14), miRFP720 (SEQ ID NO: 15), or having 90% or greater identity to one of SEQ ID NO: 11, SEQ ID NO: 12, SEQ ID NO:13, SEQ ID NO:14, or SEQ ID NO:15.

This invention also provides an isolated nucleic acid encoding a protein comprising consecutive amino acid residues having the sequence set forth in miRFP670-2 (SEQ ID NO: 11), miRFP702 (SEQ ID NO:12), miRFP682 (SEQ ID NO:13), miRFP713 (SEQ ID NO:14), miRFP720 (SEQ ID NO:15). This invention also provides an isolated nucleic acid encoding a protein comprising consecutive amino acid residues having 90% or greater identity to one of SEQ ID NO: 11, SEQ ID NO: 12, SEQ ID NO: 13, SEQ ID NO: 14, or SEQ ID NO: 15.

In another embodiment, the invention provides an isolated nucleic acid encoding a protein comprising, wherein the protein comprises at least four amino acid residues selected from the group consisting of D300, E300, K300, R300, D301, E301, K301, R301, D304, E304, K304, R304, D305, E305, K305, R305, T308, S308, G308, and A308, and wherein the amino acid positions correspond to SEQ ID NOs: 1-4.

In another embodiment, the invention provides an isolated nucleic acid encoding a protein comprising, wherein the protein comprises at least four amino acid residues selected from the group consisting of D295, E295, K295, R295, D296, E296, K296, R296, D298, E298, K298, R298, D299, E299, K299, R299, T302, S302, G302, and A302, and wherein the amino acid positions correspond to SEQ ID NOs: 11-12.

In another embodiment, the invention provides an isolated nucleic acid encoding a protein comprising, wherein the protein comprises at least four amino acid residues selected from the group consisting of D301, E301, K301, R301, D302, E302, K302, R302, D305, E305, K305, R305, D306, E306, K306, R306, T309, S309, G309, and A309, and wherein the amino acid positions correspond to SEQ ID NOs: 13-15.

In some instances, functional FPs can include polypeptides having the sequence set forth in miRFP670v1 (SEQ ID NO: 1), miRFP670 (SEQ ID NO:2), miRFP703 (SEQ ID NO:3), or miRFP709 (SEQ ID NO:4), miRFP670-2 (SEQ ID NO: 11), miRFP702 (SEQ ID NO: 12), miRFP682 (SEQ ID NO:13), miRFP713 (SEQ ID NO:14), miRFP720 (SEQ ID NO:15) that are truncated, i.e. 19 or fewer amino-acids are removed from the N-terminus.

Also provided is a nucleic acid construct, said nucleic acid construct comprising at least a portion encoding one of the proteins as described herein.

Also provided is a nucleic acid construct comprising a nucleic acid sequence of interest and a nucleic acid sequence encoding a FP comprising consecutive amino acid residues having the sequence set forth in miRFP670v1 (SEQ ID NO: 1), miRFP670 (SEQ ID NO:2), miRFP703 (SEQ ID NO:3), or miRFP709 (SEQ ID NO:4), miRFP-PAS (SEQ ID NO:5), miRFP-PAS1 (SEQ ID NO:6), miRFP-GAF670 (SEQ ID NO:7), miRFP-GAF703 (SEQ ID NO:8), miRFP-GAF709 (SEQ ID NO:9), miRFP670-2 (SEQ ID NO: 11), miRFP702 (SEQ ID NO:12), miRFP682 (SEQ ID NO:13), miRFP713 (SEQ ID NO:14), miRFP720 (SEQ ID NO:15) or having 90% or greater identity to one of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:11, SEQ ID NO:12, SEQ ID NO:13, SEQ ID NO:14, or SEQ ID NO:15.

Also provided is a composition comprising any one or more of the isolated proteins, isolated nucleic acids, or the nucleic acid constructs described herein.

The invention also provides a host cell comprising any one or more of the isolated proteins, isolated nucleic acids, or the nucleic acid constructs described herein, wherein the host cell is not a cell in a human.

The invention also provides a host cell comprising a nucleic acid construct, said nucleic acid construct comprising at least a portion encoding one of the proteins as described herein, wherein the host cell is not a cell in a human.

The invention provides a kit, said kit comprising a nucleic acid as described herein, or a nucleic acid construct as described herein, and instructions for use thereof.

The invention provides a method of optical imaging, the method comprising the step of expressing in a cell a nucleic acid sequence encoding one of the proteins as described herein and detecting or quantifying fluorescence therefrom.

A method is provided of identifying expression of a nucleic acid sequence of interest in a cell comprising contacting the cell with a nucleic acid construct comprising a nucleic acid sequence of interest and a nucleic acid sequence encoding a protein comprising consecutive amino acid residues having the sequence set forth in miRFP670v1 (SEQ ID NO: 1), miRFP670 (SEQ ID NO:2), miRFP703 (SEQ ID NO:3), miRFP709 (SEQ ID NO:4), miRFP-PAS (SEQ ID NO:5), miRFP-PAS1 (SEQ ID NO:6), miRFP-GAF670 (SEQ ID NO:7), miRFP-GAF703 (SEQ ID NO:8), miRFP-GAF709 (SEQ ID NO:9), miRFP670-2 (SEQ ID NO: 11), miRFP702 (SEQ ID NO:12), miRFP682 (SEQ ID NO:13), miRFP713 (SEQ ID NO:14), miRFP720 (SEQ ID NO: 15)

or a protein with 90% or greater identity to one of SEQ ID NOS:1-9, 11-15, under conditions permitting the construct to enter the cell and express the nucleic acid sequence of interest and the nucleic acid sequence encoding the protein, and detecting fluorescence of the protein in the cell, wherein detection of fluorescence of the protein in the cell indicates that the nucleic acid sequence of interest has been expressed in the cell, and wherein no fluorescence of the protein detected in the cell indicates that the nucleic acid sequence of interest has not been expressed in the cell.

Also provided is a fusion protein comprising (i) consecutive amino acid residues having the sequence set forth in miRFP670v1 (SEQ ID NO: 1), miRFP670 (SEQ ID NO:2), miRFP703 (SEQ ID NO:3), miRFP709 (SEQ ID NO:4), miRFP-PAS (SEQ ID NO:5), miRFP-PAS1 (SEQ ID NO:6), miRFP-GAF670 (SEQ ID NO:7), miRFP-GAF703 (SEQ ID NO:8), miRFP-GAF709 (SEQ ID NO:9), miRFP670-2 (SEQ ID NO: 11), miRFP702 (SEQ ID NO: 12), miRFP682 (SEQ ID NO:13), miRFP713 (SEQ ID NO:14), miRFP720 (SEQ ID NO:15) or a protein with 90% or greater identity to one of SEQ ID NOS:1-9, 11-15, joined at a terminus thereof to a peptide, polypeptide, or protein of interest by a peptide bond.

The invention provides a method of detecting PPIs between a first test polypeptide and a second test polypeptide, where miRFP-PAS (SEQ ID NO:5) or miRFP-PAS1 (SEQ ID NO:6) is fused to the first polypeptide, and miRFP-GAF670 (SEQ ID NO:7), miRFP-GAF703 (SEQ ID NO:8), or miRFP-GAF709 (SEQ ID NO:9) is fused to the second polypeptide. Detecting the fluorescence of this protein complex detects the PPI between the first and the second test polypeptides.

The invention provides a method of producing NIR luminescence signal in a fusion protein comprising (i) consecutive amino acid residues having the sequence set forth in miRFP670v1 (SEQ ID NO: 1), miRFP670 (SEQ ID NO:2), miRFP703 (SEQ ID NO:3), miRFP709 (SEQ ID NO:4), miRFP670-2 (SEQ ID NO: 11), miRFP702 (SEQ ID NO: 12), miRFP682 (SEQ ID NO:13), miRFP713 (SEQ ID NO:14), miRFP720 (SEQ ID NO:15) or a protein with 90% or greater identity to one of SEQ ID NOS:1-4, 11-15, joined at a terminus thereof to Renilla luciferase. The NIR luminescence signal results from bioluminescence resonance energy transfer (BRET) between the disclosed FPs and Renilla luciferase.

The invention provides a method of detecting the changes in the protein level of a polypeptide or a fusion protein as a reporter of a process of interest, including cell signaling and progression through the cell cycle where a fusion protein comprises (i) consecutive amino acid residues having the sequence set forth in miRFP670v1 (SEQ ID NO: 1), miRFP670 (SEQ ID NO:2), miRFP703 (SEQ ID NO:3), miRFP709 (SEQ ID NO:4), miRFP670-2 (SEQ ID NO: 11), miRFP702 (SEQ ID NO:12), miRFP682 (SEQ ID NO:13), miRFP713 (SEQ ID NO:14), miRFP720 (SEQ ID NO: 15) or a protein with 90% or greater identity to one of SEQ ID NOS:1-4, 11-15, joined at a terminus thereof to a functional protein that senses the signal.

The invention provides a method of detecting the changes in the Forster resonance energy transfer (FRET) between the disclosed FPs comprising consecutive amino acid residues having the sequence set forth in miRFP670v1 (SEQ ID NO: 1), miRFP670 (SEQ ID NO:2), miRFP703 (SEQ ID NO:3), miRFP709 (SEQ ID NO:4), miRFP670-2 (SEQ ID NO: 11), miRFP702 (SEQ ID NO:12), miRFP682 (SEQ ID NO:13), miRFP713 (SEQ ID NO:14), miRFP720 (SEQ ID NO: 15) or a protein with 90% or greater identity to one of SEQ ID NOS:1-4, 11-15 and its partner in a variety of FRET-based biosensors, including a caspase sensor.

The present invention relates to a diagnostic composition as well as a kit and to methods of detecting the expression of a gene of interest, detecting the activity of a promoter of interest, detecting the presence of a protein of interest, detecting the localization of a polypeptide or a fusion protein of the invention in a cell or tissue, detecting the changes in the protein level of a polypeptide or a fusion protein as a reporter of a process of interest, including cell signaling and progression through the cell cycle, detecting the changes in the FRET between the disclosed FP and its partner in a variety of FRET-based biosensors, including a caspase sensor, detecting a NIR luminescence as a result of bioluminescence resonance energy transfer (BRET) between the disclosed FPs and Renilla luciferase.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8. Alignment of the amino acid sequences of NIR FPs miRFP670v1 (SEQ ID NO: 1), miRFP670 (SEQ ID NO:2), miRFP703 (SEQ ID NO:3) and miRFP709 (SEQ ID NO:4) with wild-type PAS-GAF domains of parental RpBphP1 (SEQ ID NO:10). The amino acid substitutions in the miRFPs are highlighted in yellow. To create miSplit reporters, the miRFP670 and iRFP709 sequences were cut between the PAS and GAF domains; four amino acid residues present in both the PAS fragment and the GAF fragment of mSplits are highlighted in green.

FIG. 9A-9B. Alignment of the amino acid sequences of NIR FPs miRFP670v1 (SEQ ID NO: 1), miRFP670 (SEQ ID NO:2), miRFP703 (SEQ ID NO:3) and miRFP709 (SEQ ID NO:4) with monomerized NIR FPs miRFP670-2 (SEQ ID NO: 11), miRFP702 (SEQ ID NO: 12), miRFP682 (SEQ ID NO:13), miRFP713 (SEQ ID NO:14), and miRFP720 (SEQ ID NO:15). The amino acid substitutions responsible for the monomeric state are highlighted in yellow. NIR FPs are grouped by their origin. miRFP670v1 (SEQ ID NO:1), miRFP670 (SEQ ID NO:2), miRFP703 (SEQ ID NO:3) and miRFP709 (SEQ ID NO:4) were derived from RpBphP1 (SEQ ID NO: 10). miRFP670-2 (SEQ ID NO: 11), miRFP702 (SEQ ID NO: 12) were derived from RpBphP6 (SEQ ID NO:16). miRFP682 (SEQ ID NO:13), miRFP713 (SEQ ID NO:14), and miRFP720 (SEQ ID NO:15) were derived from RpBphP2 (SEQ ID NO:17).

FIG. 10A-10C. Monomerization strategy described here, compared to monomerization strategies applied previously. (a) Alignment of the C-termini of parental proteins (RpBphP1, iRFP670, and iRFP720) and miRFPs derived from them. (b) Monomerization strategy applied previously to obtain IFP1.4 (3) and IFP2.0 (18). Both IFP1.4 and IFP2.0 later were found to form dimers (1, 17). In addition, strategy applied to obtain IFP1.4 resulted in a substantial decrease of brightness (18). (c) Monomerization strategy applied to obtain Wi-Phy (9), which also did not result in development of monomeric NIR FP suitable for imaging in mammalian cells. (a-c) Targeted positions are in red. Positions that claimed as critical for monomeric state of resulting monomerized NIR FPs are highlighted in yellow.

DETAILED DESCRIPTION OF THE INVENTION

Figures 1A, 1B, 1C, 1D, 1E, 1F:
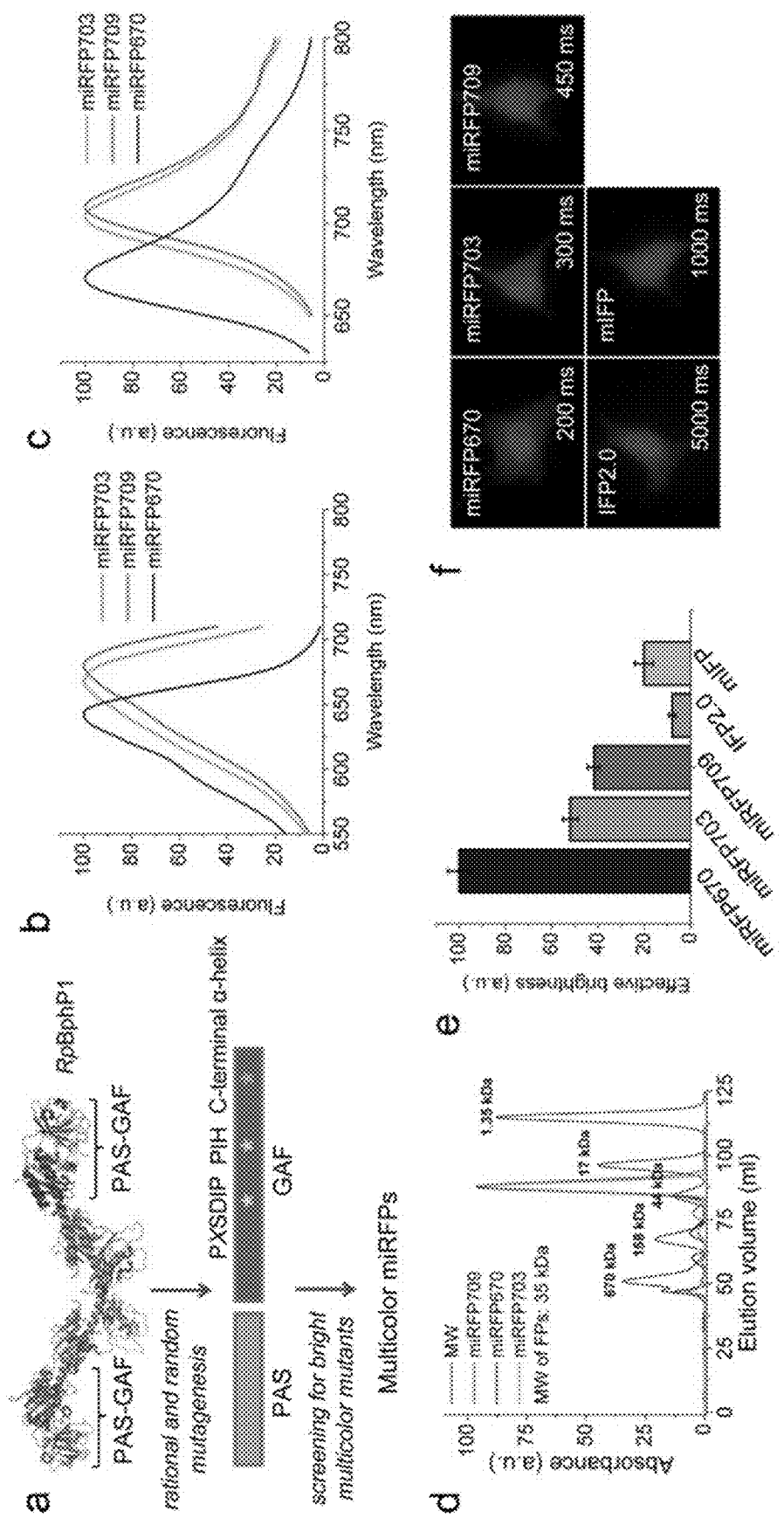
FIG. 1A-1F. Development and characterization of three monomeric miRFPs. (a) Schematics of directed molecular evolution resulted in three monomeric miRFPs. The chromophore-binding PAS-GAF domains, which are not involved in dimerization of RpBphP1, were used as a starting point. To exclude formation of even weak dimers, we mutated residues in the C-terminal α-helix in the GAF domain. To obtain spectrally distinct variants, we mutated residues 201 and 202 in the -PXSDIP- motif and residue 253 in the -PIH- motif in the GAF domain. (b) Fluorescence excitation spectra of engineered miRFP670, miRFP703 and miRFP709. (c) Fluorescence emission spectra of miRFPs. (d) Size exclusion chromatography of miRFPs and indicated molecular weight standards. Apparent molecular weight of all miRFPs was ~35 kDa. (e) Brightness of live HeLa cells transiently transfected with several BphP-based NIR FPs analyzed by flow cytometry. The NIR fluorescence intensity was normalized to transfection efficiency (fluorescence of co-transfected EGFP), to excitation efficiency of each FP with 635 nm laser, and to fluorescence signal of each FP in the emission filter. The NIR effective brightness of miRFP670 was assumed to 100%. Error bars, s.d. (n=3; transfection experiments). (f) Representative fluorescence images of several BphP-based NIR FPs in live HeLa cells. Acquisition time for each image is indicated. Scale bar, 10 μm.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

[It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As summarized above, the subject invention is directed to nucleic acid molecules FPs miRFP670, miRFP670v1, miRFP703, miRFP709, their split fragments, monomerized versions of dimeric iRFPs, i.e. miRFP670-2, miRFP682, miRFP702, miRFP713, miRFP720, variants and derivatives thereof, and proteins and peptides encoded by these nucleic acids. Also provided are vectors and expression cassettes comprising these nucleic acids, and stable cell lines, transgenic animals, and transgenic plants comprising these nucleic acids, vectors or expression cassettes. Also provided are methods of producing these FPs and mutants thereof, and antibodies specifically binding to these FPs and mutants or fragments thereof. Also provided are methods that use a FP of the present invention or the nucleic acid encoding it. Additionally, kits comprising nucleic acids or vectors or expression cassettes harboring the nucleic acids, or proteins of the present invention are provided. Also provided is a method for monomerization that involves introduction of at least four residues at specific positions in the C-terminus of the NIR FP (charged residues at positions 300, 301, 304, 305, and small or polar amino acid residues at position 308; numbering is according to RpBphP1, i.e. SEQ ID NO: 10, the corresponding positions in other FPs are derived from alignment with RpBphP1).

Definitions

Various terms relating to the biological molecules of the present invention are used herein above and also throughout the specifications and claims.

The term "nucleic acid molecule" or "polynucleotide." refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. It will be understood that when a nucleic acid molecule is represented by a DNA sequence, this also includes RNA molecules having the corresponding RNA sequence in which "U" (uridine) replaces "T" (thymidine).

The term "recombinant nucleic acid molecule" refers to a non-naturally occurring nucleic acid molecule containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a FP variant of the invention linked to a polypeptide of interest. The term "recombinant host cell" refers to a cell that contains a recombinant nucleic acid molecule. As such, a recombinant host cell can express a polypeptide from a "gene" that is not found within the native (nonrecombinant) form of the cell.

As used herein the term "FP" means a protein that is fluorescent; e.g., it may exhibit low, medium or intense fluorescence upon irradiation with light of the appropriate excitation wavelength. The fluorescent characteristic of FP is one that arises from the chromophore wherein the chromophore results from autocatalytic cyclization of two or more amino acid residues in the polypeptide backbone. As such, the FPs of the present invention do not include proteins that exhibit fluorescence only from residues that act by themselves as intrinsic fluors, i.e., tryptophan, tyrosine and phenylalanine.

The term "phytochrome" refers to a class of plant- and bacteria-derived proteins. Naturally occurring, non-mutant phytochromes generally absorb in the red portion of the visible spectrum. "Bacteriophytochrome" refers to a phytochrome derived from bacteria.

As used herein the term "isolated" means a molecule or a cell that is an environment different from that in which the molecule or the cell naturally occurs.

As used herein the terms "mutant" or "derivatives" or "variant" refer to protein disclosed in the present invention, in which one or more amino acids are added and/or substituted and/or deleted and/or inserted at the N-terminus, and/or the C-terminus, and/or within the native amino acid sequences of the proteins of the present invention. As used herein the term "mutant" refers to a nucleic acid molecule that encodes a mutant protein. Moreover, the term "mutant" refers to any shorter or longer version of the protein or nucleic acid herein.

As used herein, "homologue or homology" is a term used in the art to describe the relatedness of a nucleotide or peptide sequence to another nucleotide or peptide sequence, which is determined by the degree of identity and/or similarity between said sequences compared.

As used herein, an amino acid sequence or a nucleotide sequence is "substantially the same as" or "substantially similar to" a reference sequence if the amino acid sequence or nucleotide sequence has at least 85% sequence identity with the reference sequence over a given comparison window. Thus, substantially similar sequences include those having, for example, at least 85% sequence identity, at least 90% sequence identity, at least 95% sequence identity or at least 99% sequence identity. Two sequences that are identical to each other are also substantially similar. For purposes of this invention, the length of comparison sequences of FP will generally be at least 160 amino acids, preferably at least 200 amino acids. For nucleic acids, the length of comparison sequences will generally be at least 480 nucleotides, preferably at least 600 nucleotides.

Sequence identity is calculated based on a reference sequence. Algorithms for sequence analysis are known in the art, such as BLAST, described in (20). For purposes of this invention comparisons of nucleic acid or amino acid sequences are performed with Blast software provided by the National Center for Biotechnology Information using a gapped alignment with default parameters, may be used to determine the level of identity and similarity between nucleic acid sequences and amino acid sequences.

As used herein, the term "related FP" refers to a FP that has a substantially same amino acid sequence when compared to a reference FP. In general, a related FP, when compared to the reference FP sequence, has a contiguous sequence of at least about 160 amino acids that shares at least 85% sequence identity with the reference FP.

As used herein the term "miRFP-related protein" refers to the protein of SEQ ID NOS: 1-9, 11-15 and functional mutants thereof. The term "miRFP-related nucleic acid" refers to a nucleic acid that encodes an miRFP-related protein (e.g. SEQ ID NOs: 1-9, 11-15). As used herein miRFP-related protein comprises an amino acid sequence that is substantially the same as or identical to the sequences SEQ ID NOs: 1-9, 11-15). The terms "miRFP-related protein" and "miRFP-related nucleic acid" also refers to shorter or longer variants of miRFPs and their mutants and nucleic acids encoding them.

As used herein, the term "functional" implies that the nucleic or amino acid sequence is functional for the recited assay or purpose. The term "functional" when used to describe FPs means that the protein has useful excitation and emission spectra (i.e., possesses detectable fluorescence).

As used herein, "biochemical property" refers to the protein folding and maturation rate, half-life before degradation, aggregation capacity, oligomerization capacity, pH or temperature stability and optimum, and other like properties.

As used herein, "fluorescent property" or "spectral property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy.

As used herein, the term "effective brightness" in cells refers to the fluorescent signal corresponding to the cell expressing a specific FP. In contrast to molecular brightness, which is well known in the art and that depends solely on extinction coefficient and quantum yield of the FP, effective brightness of a FP in mammalian cells depends on molecular brightness, intracellular stability, efficiency of BV incorporation, and cell expression level. In contrast to GFP-like FPs, the effective brightness of BphP-based NIR FPs does not always correlate with their molecular brightness (1). Decreased cellular fluorescence of some NIR FPs results from a low specificity of BV binding and a competition between BV and other heme-derived compounds, including protoporphyrin IX, for binding to NIR FP apoproteins (13, 14).

As used herein, "aggregation" refers to the tendency or capacity of an expressed protein to form insoluble precipitates (aggregates). "Aggregation" should be distinguished from "oligomerization". In particular, mutations that reduce aggregation, e.g., increase the solubility of the protein, do not necessarily reduce oligomerization (i.e., convert tetramers to dimers or monomers or dimers to monomers).

As used herein, "oligomerization" refers to the tendency or capacity of an expressed protein to form complexes (oligomers) due to specific interaction of two or more polypeptides. Said specific interaction occurs under specified conditions, for example, physiologic conditions and is relatively stable under these conditions. Reference to a "capacity" of proteins to oligomerize indicates that the proteins can form dimers, trimers, tetramers, or the like under specified conditions. Generally, FPs have a capacity to oligomerize under physiologic conditions although, as disclosed herein, FPs also can oligomerize, for example, under pH conditions other than physiologic conditions. The conditions under which FPs oligomerize or have a tendency to oligomerize can be determined using well known methods such as gel-filtration or otherwise known in the art.

As used herein, a molecule that has a "reduced propensity to oligomerize" is a molecule that shows a reduced propensity to form structures with multiple subunits in favor of forming structures with fewer subunits. For example, a molecule that would normally form dimeric structures under physiological conditions shows a reduced propensity to oligomerize if the molecule is changed in such a way that it now has a preference to form monomers.

The term "operatively linked" or "operably linked" or the like, when used to describe chimeric proteins, refer to polypeptide sequences that are placed in a physical and functional relationship to each other. In a most preferred embodiment, the functions of the polypeptide components of the chimeric molecule are unchanged compared to the functional activities of the parts in isolation. For example, a FP of the present invention can be fused to a fusion partner of interest. In this case, the fusion molecule retains its fluorescence, and the polypeptide of interest retains its original biological activity. In some embodiments of the present invention, the activities of either the FP or the protein of interest can be reduced relative to their activities in isolation. Such fusions can also find use with the present invention.

As used herein the term "specifically hybridize" refers to the association between two single-stranded nucleic acid molecules of sufficiently complementary sequence to permit such hybridization under pre-determined conditions generally used in the art (sometimes termed "substantially complementary").

Reference to a nucleotide sequence "encoding" a polypeptide means that the sequence, upon transcription and translation of mRNA, produces the polypeptide. This includes both the coding strand, whose nucleotide sequence is identical to mRNA and whose sequence is usually provided in the sequence listing, as well as its complementary strand, which is used as the template for transcription. As any person skilled in the art recognizes, this also includes all degenerate nucleotide sequences encoding the same amino acid sequence. Nucleotide sequences encoding a polypeptide include sequences containing introns.

The term "polypeptide" or "protein" refers to a polymer of two or more amino acid residues. The terms apply to amino acid polymers in which one or more amino acid residue is an artificial chemical analogue of a corresponding naturally occurring amino acid, as well as to naturally occurring amino acid polymers. The term "recombinant protein" refers to a protein that is produced by expression of a nucleotide sequence encoding the amino acid sequence of the protein from a recombinant DNA molecule.

The term "isolated" or "purified" refers to a material that is substantially or essentially free from components that normally accompany the material in its native state in nature. Purity or homogeneity generally are determined using analytical chemistry techniques such as polyacrylamide gel electrophoresis, high performance liquid chromatography, and the like. A polynucleotide or a polypeptide is considered to be isolated when it is the predominant species present in a preparation. Generally, an isolated protein or nucleic acid molecule represents greater than 80% of the macromolecular species present in a preparation, often represents greater than 90% of all macromolecular species present, usually represents greater than 95%, of the macromolecular species, and, in particular, is a polypeptide or polynucleotide that purified to essential homogeneity such that it is the only species detected when examined using conventional methods for determining purity of such a molecule.

The term "naturally-occurring" is used to refer to a protein, nucleic acid molecule, cell, or other material that occurs in nature. For example, a polypeptide or polynucleotide sequence that is present in an organism, including in a virus. A naturally occurring material can be in its form as it exists in nature, and can be modified by the hand of man such that, for example, is in an isolated form.

The term "conservatively modified variation," when used in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a FP variant also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein. Furthermore, it will be recognized that individual substitutions, deletions or additions that alter, add or delete a single amino acid or a small percentage of amino acids (typically less than 5%, and generally less than 1%) in an encoded sequence can be considered conservatively modified. variations, provided alteration results in the substitution of an amino acid with a chemically similar amino acid. Conservative amino acid substitutions providing functionally similar amino acids are well known in the art, including the following six groups, each of which contains amino acids that are considered conservative substitutes for each another: 1) Alanine (Ala, A), Serine (Ser, S), Threonine (Thr, T); 2) Aspartic acid (Asp, D), Glutamic acid (Glu, E); 3) Asparagine (Asn, N), Glutamine (Gln, Q); 4) Arginine (Arg, R), Lysine (Lys, K); 5) Isoleucine (Ile, I), Leucine (Leu, L), Methionine (Met, M), Valine (Val, V); and 6) Phenylalanine (Phe, F), Tyrosine (Tyr, Y), Tryptophan (Trp, W).

Two or more amino acid sequences or two or more nucleotide sequences are considered to be "substantially identical" or "substantially similar" if the amino acid sequences or the nucleotide sequences share at least 80% sequence identity with each other, or with a reference sequence over a given comparison window. Thus, substantially similar sequences include those having, for example, at least 85% sequence identity, at least 90% sequence identity, at least 95% sequence identity, or at least 99% sequence identity.

Fluorescent molecules are useful in fluorescence resonance energy transfer, FRET, which involves a donor molecule and an acceptor molecule. To optimize the efficiency and detectability of FRET between a donor and acceptor molecule, several factors need to be balanced. The emission spectrum of the donor should overlap as much as possible with the excitation spectrum of the acceptor to maximize the overlap integral. Also, the quantum yield of the donor moiety and the extinction coefficient of the acceptor should be as high as possible to maximize Ro, which represents the distance at which energy transfer efficiency is 50%. However, the excitation spectra of the donor and acceptor should overlap as little as possible so that a wavelength region can be found at which the donor can be excited efficiently without directly exciting the acceptor because fluorescence arising from direct excitation of the acceptor can be difficult to distinguish from fluorescence arising from FRET. Similarly, the emission spectra of the donor and acceptor should overlap as little as possible so that the two emissions can be clearly distinguished. High fluorescence quantum yield of the acceptor moiety is desirable if the emission from the acceptor is to be measured either as the sole readout or as part of an emission ratio. One factor to be considered in choosing the donor and acceptor pair is the efficiency of fluorescence resonance energy transfer between them. Preferably, the efficiency of FRET between the donor and acceptor is at least 10%, more preferably at least 50% and even more preferably at least 80%.

For miRFPs (SEQ ID NOs: 1-4) derived from RpBphP1 (SEQ ID NO: 10), numeration of amino acid residues and substitutions correspond to the numeration of the PAS-GAF domains of the wild-type RpBphP1 sequence (SEQ ID NO: 10). For miRFPs derived dimeric iRFP670, iRFP702 (SEQ ID NOs: 11-12) engineered from RpBphP6 (SEQ ID NO: 16), numeration of amino acid residues and substitutions correspond to the numeration of the PAS-GAF domains of the wild-type RpBphP6 sequence (SEQ ID NO: 16). For miRFPs derived from dimeric iRFP682, iRFP713, iRFP720 (SEQ ID NOs: 13-15) engineered from RpBphP2 (SEQ ID NO: 17), numeration of amino acid residues and substitutions correspond to the numeration of the PAS-GAF domains of the wild-type RpBphP2 sequence (SEQ ID NO: 17). For mutant proteins, the position of the amino acid residue or substitution should be determined using protein alignment (FIG. 8, 9).

The term "Split FP" refers to a protein complex composed of two protein fragments that individually are not fluorescent, but, when formed into a complex, result in a functional (that is, fluorescing) FP complex. The fragments of the FP that reconstitute a FP when brought in close proximity are termed "SFP split fragments" or just "split fragments". Complementing fragments which will spontaneously assemble into a functional FP complex are known as self-complementing, self-assembling, or spontaneously-associating complementing fragments. A complemented split FP complex is a protein complex comprising all the complementing fragments of a SFP necessary for the SFP to be active (i.e., fluorescent). Complementary SFP fragments can be derived from the three dimensional structure of a FP or a homologous wild-type phytochrome (21-24). For the disclosed SFP split fragments correspond to the PAS and the GAF domains of the miRFP-related FP. The PAS and the GAF domain are determined according to the alignment with the homologous phytochromes, whose crystal structures are available (25). Specifically for miRFP-related proteins, the PAS domain corresponds to the fragment comprising at least amino acid residues with positions at 16-120, preferably 1-125; the GAF domain corresponds to the fragment comprising at least amino acid residues with positions at 130-310, preferably 126-315. The amino acid positions correspond to SEQ ID NOs:1-4.

Nucleic Acid Molecules

The present invention provides nucleic acid molecules encoding FPs miRFP670, miRFP670v1, miRFP703, miRFP709, their split fragments miRFP-PAS, miRFP-PAS1, miRFP-GAF670, miRFP-GAF703, miRFP-GAF709, and also monomerized FPs miRFP670-2, miRFP682, miRFP702, miRFP713, miRFP720 (SEQ ID NOs: 1-9, 11-15) and mutants thereof. Nucleic acid molecules encoding shorter or longer variants of the miRFP-related proteins or their mutants are also in the scope of the invention. A nucleic acid molecule as used herein is DNA molecules, such as genomic DNA molecules or cDNA molecules, or RNA molecules, such as mRNA molecules. In particular, the nucleic acid molecule is a cDNA molecule having an open reading frame that encodes a FP of the invention and is capable, under appropriate conditions, of being expressed as a FP according to the invention. The invention also encompasses nucleic acids that are homologous, substantially similar to, identical to, derived from, or mimetics of the nucleic acids encoding proteins of the present invention. The subject nucleic acids are present in an environment other than their natural environment; e.g., they are isolated, present in enriched amounts, or are present or expressed in vitro or in a cell or organism other than their naturally occurring environment.

Specific nucleic acid molecules of interest include nucleic acid molecules that encode the following FPs, and homologs/derivates/mutants thereof: miRFP670v1 (SEQ ID NO: 1), miRFP670 (SEQ ID NO:2), miRFP703 (SEQ ID NO:3), or miRFP709 (SEQ ID NO:4), miRFP-PAS (SEQ ID NO:5), miRFP-PAS1 (SEQ ID NO:6), miRFP-GAF670 (SEQ ID NO:7), miRFP-GAF703 (SEQ ID NO:8), miRFP-GAF709 (SEQ ID NO:9), miRFP670-2 (SEQ ID NO: 11), miRFP702 (SEQ ID NO:12), miRFP682 (SEQ ID NO:13), miRFP713 (SEQ ID NO:14), and miRFP720 (SEQ ID NO:15). Each of these particular types of nucleic acid molecules of interest is discussed below and in the experimental section.

Each of these particular types of nucleic acid molecules of interest is discussed below in more detail in the experimental part.

Nucleic acid molecules encoding the FPs of the invention may be synthesized from appropriate nucleotide triphosphates. The method of enables preparation of isolated nucleic acid molecules of the invention by oligonucleotide synthesis is well-known in the art. In the case of amino acid sequence information, a number of nucleic acids that differ from each other due to degenerate code may be synthesized. The methods to select codon usage variants for desired hosts are well known in the art.

In addition to the above described specific nucleic acid compositions, also of interest are homologues of the above sequences. With respect to homologues of the subject nucleic acids, the source of homologous genes may be any species of plant or animal or the sequence may be wholly or partially synthetic (e.g. genetically engineered). In certain embodiments, sequence similarity between homologues is at least about 20%, sometimes at least about 25%, and may be 30%, 35%, 40%, 50%, 60%, 70% or higher, including 75%, 80%, 85%, 90% and 95% or higher. Sequence similarity is calculated based on a reference sequence, which may be a subset of a larger sequence, such as a conserved motif, coding region, flanking region, etc. A reference sequence will usually be at least about 18 contiguous nucleotides long, more usually at least about 30 contiguous nucleotides long, and may extend to the complete sequence that is being compared. Algorithms for sequence analysis are known in the art, such as BLAST, described in (20) (using default settings, i.e. parameters w=4 and T=17). The sequences provided herein are essential for recognizing related and homologous nucleic acids in database searches. Also of interest are nucleic acids of substantially the same length as the nucleic acid identified as SEQ ID NOS:1-9, 11-15, where by substantially the same length is meant that any difference in length does not exceed about 10%, usually does not exceed about 5%; and have sequence identity to any of these sequences of about 90% or more, usually at least about 95% and more, usually at least about 99% over the entire length of the nucleic acid. In many embodiments, the nucleic acids have a sequence that is substantially similar (i.e. the same as) or identical to the sequences of SEQ ID NOS:1-9, 11-15. By substantially similar is meant that sequence identity will generally be at least about 90%, usually at least about 95% and often at least about 96%, 97%, 98%, or even 99%.

Mutants or derivatives can be generated on a template nucleic acid selected from the described-above nucleic acids by modifying, deleting or adding one or more nucleotides in the template sequence, or a combination thereof, to generate a variant of the template nucleic acid. The modifications, additions or deletions can be introduced by any convenient method, including error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-directed mutagenesis, random mutagenesis, gene reassembly, gene site saturated mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and combinations thereof, e.g., (26-28) and Sambrook et al., Molecular Cloning: A Laboratory Manual, (1989), CSH Press, pp. 15.3-15.108. The FPs encoded by mutant or derived nucleic acids may have the same fluorescent or biochemical properties as the initial FP. Alternatively, the mutant or derived nucleic acids may encode FPs with altered properties, e.g., they can have altered photostability, oligomerization state, excitation and emission spectra, quantum yield, extinction coefficient.

In addition, degenerate variants of the nucleic acids that encode the proteins of the present invention are also provided. Degenerate variants of nucleic acids are nucleic acids in which the amino-acid encoding codons are replaced with other codons encoding the same amino acids. For example, degenerate variants of a nucleic acid are generated to increase its expression in a host cell. In this embodiment, codons of the nucleic acid that are non-preferred or are less preferred in the host cell are replaced with the codons over-represented in coding sequences in genes in the host cell, wherein the replaced codons encodes the same amino acid.

The term "cDNA" as used herein is intended to include nucleic acids that share the arrangement of sequence elements found in native mature mRNA species, where sequence elements are exons and 5' and 3' non-coding regions. Normally mRNA species have contiguous exons, with the intervening introns, when present, being removed by nuclear RNA splicing, to create a continuous open reading frame encoding the protein.

A genomic sequence of interest may comprise the nucleic acid present between the initiation codon and the stop codon, as defined in the listed sequences, including all of the introns that are normally present in a native chromosome. The genomic sequence of interest further may include 5' an 3' non-translated regions found in the mature mRNA, as well as specific transcriptional and translational regulatory sequences, such as promoters, enhancers, etc., including about 1 kb, but possibly more, of flanking genomic DNA at either the 5' or 3' end of the transcribed region.

The nucleic acid molecules of the invention may encode all or a part of the FPs having amino acid sequences represented by SEQ ID NOs: 1-9, 11-15 or mutants thereof. In certain embodiments, the nucleic acid molecules encodes complete or truncated (minimum) of the subject proteins that are capable to be fluorescent when expressed in vitro and\or in vivo.

Double- or single-stranded fragments may be obtained from the DNA sequence by chemically synthesizing oligonucleotides in accordance with conventional methods, by restriction enzyme digestion, by PCR amplification, etc. For the most part, DNA fragments will be at least about 15 nucleotides in length, usually at least about 18 nucleotides in length or about 25 nucleotides in length, and may be at least about 50 nucleotides in length, about 100, about 200, about 300, about 400, about 500, about 600, about 700 contiguous nucleotides or greater in length. The DNA fragment may share 50%, 55%, 60%, 65%, 70%, 75% or more sequence identity with a fragment of the subject nucleic acid, e.g. 80%, 85%, or 90% or more identity, more often 92%, 95%, 96%, 97%, 99% or more, e.g. 100% identity with a fragment of the subject nucleic acid that is about 15 contiguous nucleotides in length, about 18 contiguous nucleotides in length, about 25 contiguous nucleotides in length, about 50 contiguous nucleotides in length, or about 100, about 200, about 300, about 400, about 500, about 600, or about 700 contiguous nucleotides or greater in length.

The subject nucleic acids may encode fragments of the subject proteins or the full-length proteins; e.g., the subject nucleic acids may encode polypeptides of about 25 amino acids, about 50, about 75, about 100, about 125, about 150, about 200 amino acids, 214 amino acids; 215 amino acids; 217 amino acids; 218 amino acids; 219 amino acids; 220 amino acids; up to the full length protein.

The subject nucleic acids may be isolated and obtained in substantially purified form. Substantially purified form means that the nucleic acids are at least about 80% pure, usually at least about 90% pure and are typically "recombinant", i.e., flanked by one or more nucleotides with which they are not normally associated on a naturally-occurring chromosome in a natural host organism.

The nucleic acids of the present invention, e.g. the corresponding cDNAs, full-length genes and constructs can be generated synthetically by a number of different protocols known to those of skill in the art. Appropriate nucleic acid constructs are purified using standard recombinant DNA techniques as described in, for example, and Sambrook et al., Molecular Cloning: A Laboratory Manual, (1989), CSH Press, and under regulations described in, e.g., United States Dept. of HHS, National Institute of Health (NIH) Guidelines for Recombinant DNA Research.

Nucleic acids encoding shorter or longer variants of the SEQ ID Nos 1-9, 11-15 or mutants thereof are also in the scope of the invention. As used herein, these protein variants comprise amino acid sequences of miRFP-related protein with modified C-, N-, or both termini. In longer variants, the C- or N-terminus of the protein may comprise additional amino acid residues. In shorter variants one or more (usually up to 19, more usually up to 14 and preferably up to 13) amino acid residues should be eliminated from the sequence or replaced by any other amino acid residues. Such modifications do not substantially alter fluorescent properties of the proteins, but can facilitate protein folding in host cells, decrease aggregation capacity or modulate other biochemical properties of the proteins, for example, cellular brightness. In some embodiments, these modifications do not modify biochemical properties of the protein. All types of modifications and mutations noted above are performed at the nucleic acid level.

The nucleic acid molecules of the invention may encode all or a part of the subject proteins. Double- or single-stranded fragments may be obtained from the DNA sequence by chemically synthesizing oligonucleotides in accordance with conventional methods, by restriction enzyme digestion, by PCR amplification, etc. For the most part, DNA fragments will be at least about 15 nucleotides in length, usually at least about 18 nucleotides in length or about 25 nucleotides in length, and may be at least about 50 nucleotides in length. In some embodiments, the subject nucleotide acid molecules may be about 100, about 200, about 300, about 400, about 500, about 600, about 700 nucleotides or greater in length. The subject nucleic acids may encode fragments of the subject proteins or the full-length proteins; e.g., the subject nucleic acids may encode polypeptides of about 25 amino acids, about 50, about 75, about 100, about 125, about 150, or about 200 amino acids up to the full length protein.

The subject nucleic acids may be isolated and obtained in substantially purified form. Substantially purified form means that the nucleic acids are at least about 50% pure, usually at least about 90% pure and are typically "recombinant", i.e., flanked by one or more nucleotides with which it is not normally associated on a naturally-occurring chromosome in its natural host organism.

Also provided are nucleic acids that encode fusion proteins comprising a FP of the present invention that are discussed in more details below.

Also provided are vector and other nucleic acid constructs comprising the subject nucleic acids. Suitable vectors include viral and non-viral vectors, plasmids, cosmids, phages, etc., preferably plasmids, and used for cloning, amplifying, expressing, transferring etc. of the nucleic acid sequence of the present invention in the appropriate host. The choice of appropriate vector is well within the skill of the art, and many such vectors are available commercially. To prepare the constructs, the partial or full-length nucleic acid is inserted into a vector typically by means of DNA ligase attachment to a cleaved restriction enzyme site in the vector. Alternatively, the desired nucleotide sequence can be inserted by homologous recombination in vivo, typically by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems used inter alia for the production of the subject chromogenic or FPs or fusion proteins thereof or for replication of the subject nucleic acid molecules. The expression cassette may exist as an extrachromosomal element or may be integrated into the genome of the cell as a result of introduction of said expression cassette into the cell. For expression, the gene product encoded by the nucleic acid of the invention is expressed in any convenient expression system, including, for example, bacterial, yeast, insect, amphibian, or mammalian systems. In the expression vector, a subject nucleic acid is operatively linked to a regulatory sequence that can include promoters, enhancers, terminators, operators, repressors and inducers. Methods for preparing expression cassettes or systems capable of expressing the desired product are known for a person skilled in the art.

Cell lines, which stably express the proteins of present invention, can be selected by the methods known in the art (e.g., co-transfection with a selectable marker such as dhfr, gpt, neomycin, hygromycin allows the identification and isolation of the transfected cells that contain the gene integrated into a genome).

The above-described expression systems may be used in prokaryotic or eukaryotic hosts. Host-cells such as *E. coli, B. subtilis, S. cerevisiae*, insect cells in combination with baculovirus vectors, or cells of a higher organism such as vertebrates, e.g., COS 7 cells, HEK 293, CHO, *Xenopus* oocytes, etc., may be used for production of the protein.

When any of the above-referenced host cells, or other appropriate host cells or organisms are used to replicate and/or express the nucleic acids of the invention, the resulting replicated nucleic acid, expressed protein or polypeptide is within the scope of the invention as a product of the host cell or organism. The product may be recovered by an appropriate means known in the art.

Also provided are small DNA fragments of the subject nucleic acids, that are useful as primers for PCR, hybridization screening probes, etc. Larger DNA fragments are useful for production of the encoded polypeptide, as described previously. However, for use in geometric amplification reactions, such as geometric PCR, a pair of small DNA fragments, i.e., primers, will be used. The exact composition of the primer sequences is not critical for the invention, but for most applications, the primers will hybridize to the subject sequence under stringent conditions, as is known in the art. It is preferable to choose a pair of primers that will generate an amplification product of at least about 50 nucleotides, preferably at least about 100 nucleotides and may extend to the complete sequence of the nucleic acid. Algorithms for the selection of primer sequences are generally known, and are available in commercial software packages. Amplification primers hybridize to complementary strands of DNA and will prime toward each other.

The nucleic acid molecules of the present invention also may be used to identify expression of a gene in a biological specimen. The manner in which one probes cells for the presence of particular nucleotide sequences, such as genomic DNA or RNA, is well established in the art. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g., nitrocellulose, nylon, etc., and then probed with a fragment of the subject DNA as a probe. Other techniques, such as oligonucleotide ligation assays, in situ hybridizations, and hybridization to DNA probes arrayed on a solid chip may also be used. Detection of mRNA hybridizing to the subject sequence is indicative of gene expression in the sample.

Proteins

Also provided by the subject invention are FPs, derivatives, and mutants thereof including full-length proteins, as well as portions or fragments thereof.

As discussed above, specific FPs of interest include the following FPs: miRFP670v1 (SEQ ID NO: 1), miRFP670 (SEQ ID NO:2), miRFP703 (SEQ ID NO:3), or miRFP709 (SEQ ID NO:4) and their split versions: reconstituting miRFP670v1 (SEQ ID NO: 1): miRFP-PAS1 (SEQ ID NO:6) and miRFP-GAF670 (SEQ ID NO:7), reconstituting miRFP670 (SEQ ID NO:2): miRFP-PAS (SEQ ID NO:5) and miRFP-GAF670 (SEQ ID NO:7), reconstituting miRFP703 (SEQ ID NO:3): miRFP-PAS (SEQ ID NO:5) and miRFP-GAF703 (SEQ ID NO:8), reconstituting miRFP709 (SEQ ID NO:4): miRFP-PAS (SEQ ID NO:5) and miRFP-GAF709 (SEQ ID NO:9). Specific FPs of interest also include the following FPs, which are monomerized versions of dimeric FPs, named iRFPs: miRFP670-2 (SEQ ID NO: 11), miRFP702 (SEQ ID NO: 12), miRFP682 (SEQ ID NO: 13), miRFP713 (SEQ ID NO: 14), and miRFP720 (SEQ ID NO: 15). Also of interest are mutants and fragments thereof.

Homologs that vary in sequence from the above provided specific amino acid sequences of the subject invention, i.e., SEQ ID NOs: 1-9, 11-15 are also provided. By homolog is meant a protein having 50% or more, usually 55% or more and more usually 60% or more amino acid sequence identity to amino acid sequences of referred protein as determined using MegAlign, DNAstar clustal algorithm as described in (29) (using parameters ktuple 1, gap penalty 3, window 5 and diagonals saved 5). In many embodiments, homologs of interest have much higher sequence identity e.g., 70% or more, 75% or more, 80% or more, 85% or more, 90% or more (e.g., 92% or more, 93% or more, 94% or more), e.g., 95% or more, 96% or more, 97% or more, 98% or more, 99% or more, or 99.5%, particularly for the amino acid sequence that provides the functional regions of the protein.

Also provided are proteins that are substantially identical to the proteins of SEQ ID NOs: 1-9, 11-15, where by substantially identical is meant that the full-length protein or fragment thereof has an amino acid sequence identity to the sequence of reference protein or fragment of 90% or more, in some instances, 92% or more, or 95% or more, where in some instances the identity may be much higher, e.g., at least 96%, at least 97%, at least 98%, at least 99% or higher.

As used herein, "90% or greater identity" with regard to a sequence (e.g. of amino acid residues) means a 90.0%-

99.9% identity of sequence with the referenced SEQ ID NO. One skilled in the art is aware of the most conservative amino acid residue changes that can be made with an expectation of retention of function in the sequence having the 90% or greater identity, and these are encompassed by the present invention. The function retained is retained qualitatively (e.g. fluorescence under the same conditions) even though quantitatively the function may be less than, or in excess of, the level of that function in the referenced sequence. In addition, 90.0%-99.9% identity is understood to encompass every sub-range in between these two values to the first tenth of a percent, for example 91.0%-91.5%; 90.0%-97.2% etc., as well as every single value identity, for example, 95%, 96%, 97%, 98% or 99% or greater identity. Specifically excluded from this definition are sequences which possess a 90% or greater identity but which also are naturally occurring sequences, such as the bacterial phytochrome RpBphP1 (SEQ ID NO: 10) on which miRFP670v1, miRFP670, miRFP703 and miRFP709 and their split fragments, comprising miRFP-PAS, miRFP-PAS), miRFP-GAF670, miRFP-GAF703, miRFP-GAF709, are based.

In aspects of the invention, subject proteins and mutants thereof range in length from about 100 to 350 amino acids, more usually from about 111 to 350 amino acid residues. In aspects of the invention, the subject proteins and mutants thereof have a molecular weight ranging from about 11 to 38.5 kDa, more usually from about 12.2 to 38.5 kDa, where the molecular weight is the average molecular weight, i.e. the calculated molecular weight based upon the average weight for amino acids of 0.11 kDa per amino acid.

In aspects of the invention, the subject proteins are bright, where by bright is meant that they exhibit fluorescence that can be detected by common methods (e.g., visual screening, spectrophotometry, spectrofluorometry, fluorescence microscopy, by FACS machines, etc.) Fluorescence brightness of particular FPs is determined by its quantum yield multiplied by maximal extinction coefficient.

FPs that are mutants and derivatives of the above-described proteins, that is, mutants or derivatives that fluoresce, i.e. emit fluorescence, are also provided. Mutations contemplated include, without limitation, substitutions, deletions or insertions of one or more amino acids. It is well known in the art that, barring substitution of the amino acid residues that are strictly conserved across members of the phytochrome-based FPs, e.g. some residues of the chromophore and chromophore environment preferentially in the GAF domain, a high degree of mutation may be tolerated. Other examples of residues that may be substituted may be readily identified by cross-referencing alignments made between known members of the family of phytochrome-based FPs that identify strictly conserved residues, e.g. as provided in (16).

Additional mutations contemplated include N-terminal truncations or extensions, and/or C-terminal truncations or extensions. In an embodiment, the proteins comprising consecutive amino acid residues having 90% or greater identity to one of SEQ ID NO: 1, SEQ ID NO:2, SEQ ID NO:3, SEQ ID NO:4, SEQ ID NO: 11, SEQ ID NO:12, SEQ ID NO:13, SEQ ID NO:14, SEQ ID NO: 15, comprises a truncated variants of these protein sequences without the first 19 amino acids or less from the N-terminus (in non-limiting examples, proteins starting from position 10-20).

Aspects of the invention include mutants and variants which retain biological properties of the initial proteins (e.g., proteins subjected for mutagenesis). In other aspects of the invention, mutants and variants have biological properties which differ from the initial proteins. The term "biological property" of the proteins of the present invention refers to, without limitation, spectral properties, such as absorbance maximum, emission maximum, maximum extinction coefficient, brightness (e.g., as compared to the reference protein such miRFP703 protein), effective brightness in cells, and the like; and biochemical properties, such as in vivo and/or in vitro stability (e.g., half-life), aggregation/oligomerization tendency, and other such properties.

Aspects of the invention include proteins that comprise one or more mutations that reduces the oligomerization capacity of the subject proteins, e.g. a reduced tendency to dimerize as compared with the RpBphP1 SEQ ID NO:10, RpBphP2 SEQ ID NO: 17, RpBphP6 SEQ ID NO:16, or dimeric versions of iRFPs, derived from these BphPs, including iRFP670, iRFP702, iRFP682, iRFP713, iRFP720. The difference in dimerization can be monitored in vitro for the purified protein samples, using sensitive techniques, such as fast protein liquid chromatography (FPLC), light scattering, or analytical ultracentrifugation, all performed at high concentrations of the protein (above 20 µM). The difference can not be monitored accurately using the low pressure liquid chromatography (LPLC). In some embodiments, the mutations include at least four or more substitutions at positions corresponding to 300, 301, 304, 305, 308; numbering is according to RpBphP1, i.e. SEQ ID NO: 10, the corresponding positions in other FPs are derived from alignment with RpBphP1. Specifically, the positions numbers are 295, 296, 298, 299, 302 as numbered according to RpBphP6; and are 301, 302, 305, 306, 309 as numbered according to RpBphP2 (alignment is presented in FIG. 9).

Also provided are proteins that comprise one or more substitutions that shifts the fluorescence of the protein spectrally, i.e. it has an absorbance maximum ranging from about 630 nm to 710 nm, usually from about 635 nm to 690 nm, while the maximum of emission spectra of the subject proteins typically ranges from about 660 nm to 750 nm, usually from about 665 nm to 720 nm and more usually from about 670 to 710 nm while in many embodiments the maximum of emission spectra ranges from about 670 to 709 nm. In some embodiments, the substitution is at a position corresponding to residues 201 and/or 202, and/or 253 comparing to SEQ ID NO: 10 (in non-limiting examples, D201T, D201L, D201F, D201A, 1202, 1202C, 1202V, 1253C).

Also provided are proteins that comprise one or more substitutions that enhance brightness of fluorescent properties and their effective cellular brightness. In some embodiments, the substitution is Y257F, as numbered according to RpBphP1, i.e. SEQ ID NO: 10.

Also provided are proteins that are substantially the same as the above provided specific proteins, whereby substantially the same means that the protein has an amino acid sequence identity to the sequence of wild type protein of at least about 85% sequence identity, usually at least about 90% and more usually at least about 95%, (e.g. 95%; 96%, 97%; 98%: 99% or 100% sequence identity).

Mutants and derivates can be generated using standard techniques of molecular biology as described in details in the section "Nucleic acid molecules" above. Several mutants are described herein. Given the guidance provided in the Examples, and using standard techniques, those skilled in the art can readily generate a wide variety of additional mutants and test whether a biological (e.g., biochemical, spectral, etc.) property has been altered. For example, mutations that reduce oligomerization of a FP can be combined with mutations that improve protein folding and/or alter protein photostability, excitation/emission spectra and/or pH-stability, capability of photoactivation, etc.

For screening of mutant variants, nucleic acids encoding these variants are cloned into suitable expression vector (for example, pQE30 vector, Qiagen) and expressed in host cells (for example, in *E. coli* XL1 Blue strain, Invitrogen). Depending on the complexity of library, from 100 to 100,000 individual clones each expressing individual FP variant are screened using a fluorescence stereomicroscope equipped with the appropriate filter set (excitation filter 630-680 nm, emission filter 700 nm long-pass). Fluorescence intensity can be also measured using a spectrophotometer at various excitation wavelengths.

Proteins of interest can be also modified using standard techniques that includes RNA-editing, chemical modifications, posttranslational and posttranscriptional modifications and the like. For instance, derivatives of the proteins of interest can be generated by processes such as altered phosphorylation, or glycosylation, or acetylation, or lipidation, or by different types of maturation cleavage and the like.

The proteins of the subject invention are separated from their naturally-occurring environment. For example, purified protein is provided, where "purified" means that the protein is present in a mixture that is substantially free of non-chromogenic or FPs of interest, where "substantially free" means that less than 90%, usually less than 60% and more usually less than 50% of the mixture content is non-chromogenic or FPs or mutants thereof. The proteins of the present invention also may be present in the isolated form, by which is meant that the protein is substantially free of other proteins and other naturally-occurring biological molecules, such as oligosaccharides, nucleic acids and fragments thereof, and the like, where the term "substantially free" in this instance means that less than 70%, usually less than 60% and more usually less than 50% of the composition containing the isolated protein is some other natural occurring biological molecule. In some embodiments, the proteins are present in substantially purified form, where by "substantially purified form" means at least 95%, usually at least 97% and more usually at least 99% pure.

The subject proteins and polypeptides may be synthetically produced. For example, wild type proteins may be derived from biological sources which express the proteins. The subject proteins may be derived from synthetic means, e.g. by expressing a recombinant nucleic acid coding sequence encoding the protein of interest in a suitable host, as described above. Any convenient protein purification procedures may be employed, where suitable protein purification methodologies are described in Guide to Protein Purification, M. P. Deutscher, ed., Academic Press, 1990, 894 pp. For example, a lysate may be prepared from the original source and purified using HPLC, exclusion chromatography, gel electrophoresis, affinity chromatography, and the like.

Also provided are fusion proteins comprising a protein of the present invention, fused, for example, to a degradation sequence, a sequence of subcellular localization (e.g. nuclear localization signal, peroximal targeting signal, Golgi apparatus targeting sequence, mitochondrial targeting sequence, protein with known subcellular localization, etc.), a signal peptide, or any protein or polypeptide of interest. Fusion proteins may include for example, a FP of the subject invention or mutant thereof and a second polypeptide ("the fusion partner") fused in-frame at the N-terminus and/or C-terminus of the FP. Fusion partners include, but are not limited to, polypeptides that can bind antibodies specific to the fusion partner (e.g., epitope tags), antibodies or binding fragments thereof, polypeptides that provide a catalytic function or induce a cellular response, ligands or receptors or mimetics thereof, and the like. In such fusion proteins, the fusion partner is generally not naturally associated with the FP portion of the fusion protein.

Fusion proteins can be produced using recombinant technologies well known in the art. To generate fusion proteins, a nucleic acid encoding a subject protein is operatively linked with the nucleic acid encoding "fusion partner". In the resulted nucleic acid coding sequence of the FP and coding sequence of the "fusion partner" are covalently linked so that no frameshifts and stop codons are present between these coding sequences.

For split phytochrome-based FPs, complementing sets of two fragments, are also correspond to the PAS and the GAF domains of phytochromes, and typically include fragments corresponding to the PAS and the GAF domains of phytochromes.

Construction of a test protein fused to one of the two split fragments, i.e. a fragment corresponding to the PAS domain or a fragment corresponding to the GAF domain, is typically accomplished via cloning of the nucleic acid encoding the test protein into a nucleic acid construct encoding the split fragment.

Polypeptides comprising split phytochrome-based protein fragments are known to the skilled artisan and further described herein. E.g., see (21-24). In some embodiments, miRFP-PAS (SEQ ID NO:5) or miRFP-PAS1 (SEQ ID NO:6) may be used as a fragment corresponding to the GAF domain. miRFP-GAF670 (SEQ ID NO:7), miRFP-GAF703 (SEQ ID NO:8), miRFP-GAF709 (SEQ ID NO:9) may be used as fragments corresponding to the GAF-domain. Different combinations of the PAS and the GAF domains are possible. Split fragments disclosed herein will form a functional miRFP molecules when complemented. Specifically, miRFP-PAS1 (SEQ ID NO:6) and miRFP-GAF670 (SEQ ID NO:7) will reconstitute miRFP670v1 (SEQ ID NO: 1); miRFP-PAS (SEQ ID NO:5) and miRFP-GAF670 (SEQ ID NO:7) will reconstitute miRFP670 (SEQ ID NO:2); miRFP-PAS (SEQ ID NO:5) and miRFP-GAF703 (SEQ ID NO:8) will reconstitute miRFP703; miRFP-PAS (SEQ ID NO:5) and miRFP-GAF709 (SEQ ID NO:9) will reconstitute miRFP709 (SEQ ID NO:4).

In some examples, the split fragments are fused to another protein of interest.

It will be understood that the split fragment can be joined to an unrelated polypeptide, for example in methods of detecting protein localization or detecting PPI. The split fragment can be joined to a polypeptide of interest by means known to the person of ordinary skill in the art, for example, by joining the split fragment and the polypeptide of interest by a peptide linker. Suitable peptide linkers are known to the person of ordinary skill in the art and further disclosed herein.

In an embodiment, the sequence description for the full length miRFP-related proteins applied to the split FPs based on FPs having the sequence set forth in miRFP670v1 (SEQ ID NO: 1), miRFP670 (SEQ ID NO:2), miRFP703 (SEQ ID NO:3), or miRFP709 (SEQ ID NO:4). Specifically, having the sequences of split parts reconstituting miRFP670v1 (SEQ ID NO: 1): miRFP-PAS1 (SEQ ID NO:6) and miRFP-GAF670 (SEQ ID NO:7), having the sequences of split parts reconstituting miRFP670 (SEQ ID NO:2): miRFP-PAS (SEQ ID NO:5) and miRFP-GAF670 (SEQ ID NO:7), having the sequences of split parts reconstituting miRFP703 (SEQ ID NO:3): miRFP-PAS (SEQ ID NO:5) and miRFP- GAF703 (SEQ ID NO:8), or having the sequences of split parts reconstituting miRFP709 (SEQ ID NO:4): miRFP-PAS (SEQ ID NO:5) and miRFP-GAF709 (SEQ ID NO:9)), or having 90% or greater identity to one of SEQ ID NO:5, SEQ ID NO:6, SEQ ID NO:7, SEQ ID NO:8 or SEQ ID NO:9.

Transformants

The nucleic acids of the present invention can be used to generate transformants including transgenic organisms or site-specific gene modifications in cell lines. Transgenic cells of the subject invention include one or more nucleic acids according to the subject invention present as a transgene. For the purposes of the invention any suitable host cell may be used including prokaryotic (e.g., *Escherichia coli, Streptomyces* sp., *Bacillus subtilis, Lactobacillus acidophilus*, etc) or eukaryotic host-cells. Transgenic organisms of the subject invention can be prokaryotic or a eukaryotic organism including bacteria, cyanobacteria, fungi, plants and animals, in which one or more of the cells of the organism contains heterologous nucleic acid of subject invention introduced by way of human intervention, such as by transgenic techniques well known in the art.

The isolated nucleic acid of the present invention can be introduced into the host by methods known in the art, for example infection, transfection, transformation or transconjugation. Techniques for transferring the nucleic acid molecules (i.e., DNA) into such organisms are widely known and provided in references such as Sambrook et al., Molecular Cloning: A Laboratory Manual, 3rd edition (2001) CSH Press, Cold Spring Harbor, N.Y.

In one embodiment, the transgenic organism can be a prokaryotic organism. Methods on the transformation of prokaryotic hosts are well documented in the art (for example see Sambrook et al. Molecular Cloning: A Laboratory Manual, 2nd edition (1989) CSH Press, Cold Spring Harbor, N.Y.; and Ausubel et al., Current Protocols in Molecular Biology (1995) John Wiley & Sons.

In another embodiment, the transgenic organism can be a fungus, for example yeast. Yeast is widely used as a vehicle for heterologous gene expression (e.g., see Goodey et al., Yeast biotechnology, D R Berry et al., eds, (1987) Allen and Unwin, London, pp 401-429; and King et al., Molecular and Cell Biology of Yeasts, E. F. Walton and G. T. Yarronton, eds, Blackie, Glasgow (1989) pp 107-133). Several types of yeast vectors are available, including integrative vectors, which require recombination with the host genome for their maintenance, and autonomously replicating plasmid vectors.

Another host organism is an animal. Transgenic animals can be obtained by transgenic techniques well known in the art and provided in references such as Pinkert, Transgenic Animal Technology: a Laboratory Handbook, 2nd edition (2003), Academic Press, San Diego; Gersenstein & Vintersten, Manipulating the Mouse Embryo: A Laboratory Manual, 3rd edition (2002), Nagy A. (Ed), Cold Spring Harbor; Blau et al., Laboratory Animal Medicine, 2nd edition (2002), Fox J. G., Anderson L. C., Loew F. M. & Quimby F. W. (Eds), American Medical Association, American Psychological Association; and Gene Targeting: A Practical Approach. 2nd edition (2000), Alexandra L. Joyner (Ed.) Oxford University Press. For example, transgenic animals can be obtained through homologous recombination, wherein the endogenous locus is altered. Alternatively, a nucleic acid construct is randomly integrated into the genome. Vectors for stable integration include plasmids, retroviruses and other animal viruses, YACs, and the like.

The nucleic acid can be introduced into the cell, directly or indirectly by introduction into a precursor of the cell, by way of deliberate genetic manipulation, such as by microinjection or by infection with a recombinant virus or with a recombinant viral vector and the like. The term genetic manipulation does not include classical cross-breeding, or in vitro fertilization, but rather is directed to the introduction of a recombinant nucleic acid molecule. This nucleic acid molecule may be integrated within a chromosome, or it may be extrachromosomally replicating DNA.

DNA constructs for homologous recombination will comprise at least a portion of a nucleic acid of the present invention, wherein the gene has the desired genetic modification(s), and includes regions of homology to the target locus. DNA constructs for random integration need not include regions of homology to mediate recombination. Conveniently, markers for positive and negative selection may be included. Methods for generating cells having targeted gene modifications through homologous recombination are known in the art. For various techniques for transfecting mammalian cells, see (30).

For embryonic stem (ES) cells, an ES cell line may be employed, or embryonic cells may be obtained freshly from a host, such as a mouse, rat, guinea pig, etc. Such cells are grown on an appropriate fibroblast-feeder layer or grown in the presence of leukemia inhibiting factor (LIF). Transformed ES or embryonic cells may be used to produce transgenic animals using the appropriate technique described in the art.

The transgenic animals may be any non-human animals including non-human mammal (e.g. mouse, rat), a bird or an amphibian, etc., and used in functional studies, drug screening and the like. Representative examples of the use of transgenic animals include those described infra.

Transgenic plants also may be produced. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896; 5,576,198; 5,538,879; 5,484,956; the disclosures of which are herein incorporated by reference. Methods of producing transgenic plants also are reviewed in Plant Biochemistry and Molecular Biology, Lea and Leegood (Eds.), John Wiley & Sons) (1993), pp. 275-295 and in Plant Biotechnology and Transgenic Plants, Oksman-Caldentey and Barz (Eds.), (2002), 719 p.

For example, embryogenic explants comprising somatic cells may be used for preparation of the transgenic host. Following cell or tissue harvesting, exogenous DNA of interest is introduced into the plant cells, where a variety of different techniques is available for such introduction. With isolated protoplasts, the opportunity arises for introduction via DNA-mediated gene transfer protocols, including incubation of the protoplasts with naked DNA, such as plasmids comprising the exogenous coding sequence of interest in the presence of polyvalent cations (for example, PEG or PLO); or electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, such as auxins and cytokinins.

Other suitable methods for producing plants may be used such as "gene-gun" approach or *Agrobacterium*-mediated transformation available for those skilled in the art.

Methods of Use

The FPs of the present invention (as well as other components of the subject invention described herein) find use in a variety of different applications. For example, they may be used in the methods for labeling, analyzing or detecting a biological molecule, cell or cell organelle. Representative uses for each of these types of proteins will be described below, where the uses described herein are merely exemplary and are in no way meant to limit the use of the proteins of the present invention to those described.

In a preferred embodiment relating to the method for labeling a biological molecule, cell or cell organelle, the subject proteins find use as in vivo labels (or reporter molecules) in cell and molecular biology assays. The assays of interest include but not limited to assays for gene expression, protein localization and co-localization, PPIs, protein-nucleic acid interactions, nucleic acid-nucleic acid interactions, cell and cell organelle localization and interactions, etc. The FPs of the present invention find use as a biomolecule labels, or cell organelle labels in living and fixed cells; as a markers in cell or organelle fusion, as a cell or organelle integrity markers, as a transfection markers (e.g., as labels for selection of transfected cells containing an expression vector encoding at least one FP of the invention), as real-time probes working at near physiological concentrations, etc.

Furthermore, the subject proteins may be used in a method for analyzing gene expression (e.g., promoter activity). In the other words, they find use for identifying and/or measuring the expression of a protein or polypeptide of interest in biological material. This method comprises: i) introducing into a cell a nucleic acid molecule comprising a nucleotide sequence encoding a FP according to the present invention wherein said nucleic acid molecule is operatively linked to and under the control of an expression control sequence which moderates expression of said protein or polypeptide of interest; ii) expression of said nucleic acid under suitable conditions; and iii) detecting the fluorescence emission of the FP as a means of measuring the expression of the protein of interest.

In particular, the subject proteins find use for identifying and/or measuring the expression of protein or polypeptide of interest in the biological material (e.g. host cells). This method comprises: i) introducing into a cell a nucleic acid molecule comprising a nucleotide sequence encoding a FP according to the present invention wherein the nucleic acid molecule is operably linked to and under the control of an expression control sequence which moderates expression of the protein or polypeptide of interest; ii) culturing the cell under conditions suitable for the expression of the protein of interest; and iii) detecting the fluorescence emission of the FP as a means of measuring the expression/localization of the protein of interest.

The invention provides a method of detecting the changes in the protein level of a polypeptide or a fusion protein as a reporter of a process of interest, including but not limiting to cell signaling and progression through the cell cycle where a fusion protein comprises (i) consecutive amino acid residues having the sequence set forth in miRFP670v1 (SEQ ID NO: 1), miRFP670 (SEQ ID NO:2), miRFP703 (SEQ ID NO:3), miRFP709 (SEQ ID NO:4) or a protein with 90% or greater identity to one of SEQ ID NOS: 1-4, joined at a terminus thereof to a functional protein that senses the signal. Specific examples are provided. They include NIR reporter for canonical NF-κB pathway (FIG. 4). This reporter was designed as IκBα-miRFP703 fusion. The NIR IκBα reporter is an example of a biosensor based on the post-translational changes in protein levels. Analogous reporters for other signaling pathways can be created with bright miRFPs by using the same approach. The second specific example of a method of detecting the changes in the protein level of a fusion protein as a reporter of a cellular process is a NIR cell cycle reporter (FIG. 5). This reporter is based on Fucci reporter (31, 32). The NIR cell cycle reporter relies on two spectrally resolvable miRFPs, specifically miRFP670v1 and miRFP709, whose fusions accumulate reciprocally during the cell cycle. The ratio between signals of two miRFPs serves as an indicator of proliferation status of the cell population in vivo. In contrast to green-red GFP-based Fucci indicator, NIR cell cycle reporter is suitable for non-invasive in vivo studies. Furthermore, monomerized FPs miRFP670-2 (SEQ ID NO: 11), miRFP702 (SEQ ID NO:12), miRFP682 (SEQ ID NO:13), miRFP713 (SEQ ID NO:14), and miRFP720 (SEQ ID NO:15) can also be applied in the method described.

In particular, the subject proteins find use for identifying and/or localization of protein or polypeptide of interest in biological material. This method comprises: i) introducing into a cell a nucleic acid molecule comprising a nucleotide sequence encoding a FP according to the present invention wherein the nucleic acid molecule is operably linked with sequence encoding protein or polypeptide of interest and under the control of an promoter sequence; ii) culturing the cell under conditions suitable for the expression of the protein of interest; and iii) detecting the fluorescence emission of the FP as a means of measuring the expression/localization of the protein of interest.

The applications of interest include the use of the subject proteins in FRET methods. In these methods, the subject proteins serve as donor and/or acceptors in combination with a second FP or dye, e.g., a FP as described in (33); a mutants of green FP from Aequorea victoria, e.g., as described in U.S. Pat. Nos. 6,066,476; 6,020,192; 5,985,577; 5,976,796; 5,968,750; 5,968,738; 5,958,713; 5,919,445; 5,874,304, the disclosures of which are herein incorporated by reference; other fluorescent dyes such as coumarin and its derivatives, 7-amino-4-methylcoumarin and aminocoumarin; bodipy dyes; cascade blue; or fluorescein and its derivatives, such as fluorescein isothiocyanate and Oregon green; rhodamine dyes such as Texas red, tetramethylrhodamine, eosins and erythrosins; cyanine dyes such as Cy3 and Cy5; macrocyclic chealates of lenthaninde ions, such as quantum dye; and chemilumescent dyes such as luciferases, including those described in U.S. Pat. Nos. 5,843,746; 5,700,673; 5,674,713; 5,618,722; 5,418,155; 5,330,906; 5,229,285; 5,221,623; 5,182,202; the disclosures of which are herein incorporated by reference; or a monomeric FP provided by this invention (miRFP670v1 (SEQ ID NO: 1), miRFP670 (SEQ ID NO:2), miRFP703 (SEQ ID NO:3) and miRFP709 (SEQ ID NO:4), miRFP670-2 (SEQ ID NO: 11), miRFP702 (SEQ ID NO: 12), miRFP682 (SEQ ID NO:13), miRFP713 (SEQ ID NO:14), and miRFP720 (SEQ ID NO:15)), or other NIR FPs provided by U.S. Pat. No. US20150353609A1 and U.S. Pat. No. 8,653,037B2.

The FPs of the present invention can advantageously be used in FRET experiments. This will produce a far-red or NIR FRET pairs suitable for imaging with the common FRET pairs based on GFP-like proteins and suitable for imaging in vivo. Consequently, the polypeptides of the present invention can be employed in studies, such as e.g. FRET, in which multiple, different FPs are used simultaneously. Although such simultaneous studies are already available in the art, the FPs employed so far belong to the GFP-like FPs with excitation below 630 nm. The only reported FRET pair between NIR FP of bacteriophytochrome origin iRFP and mKate2 (34) is inferior to the FRET pair between the disclosed FPs with mKate2 in terms of FRET efficiency and it contains dimeric protein iRFP that is suboptimal for a design of several FRET-based biosensors.

Figures 6A, 6B, 6C, 6D, 6E:
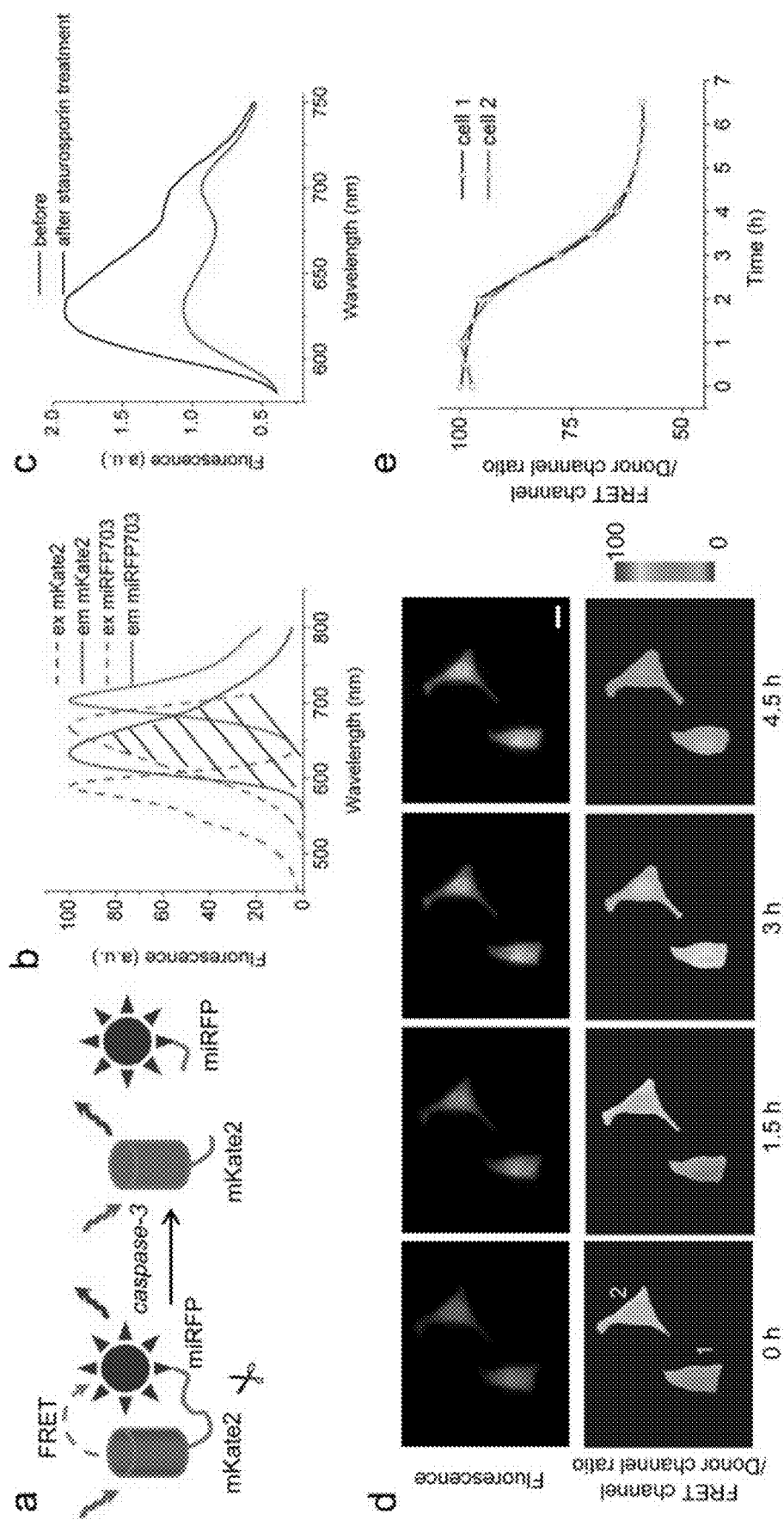
FIG. 6A-6E Characterization of mKate2-miRFP703 FRET sensor. (a) Schematic representation of a mKate2-miRFP703 caspase-3 sensor is shown. miRFP703 (also miRFP670 and miRFP709) can serve as a FRET acceptor for mKate2. Upon cleavage with caspase-3, mKate2 donor and miRFP acceptor become separated and, consequently, FRET does not occur. (b) Overlay of the normalized excitation (dashed lines) and emission (solid lines) spectra of the mKate2 donor and miRFP703 acceptor. (c) Emission spectra of the mKate2-miRFP703 sensor before and 6 h after staurosporine treatment (resulting in reporter proteolysis) measured in a suspension of the transiently transfected HeLa cells. The spectra were acquired with 540 nm excitation and normalized to fluorescence intensity of the acceptor (excited at 650 nm) in the same samples. To improve the ratio between donor and acceptor, we added BV to the cell culture to increase the number of miRFP703 molecules. (d) Microscopy time-lapse images of representative HeLa cells expressing the mKate2-miRFP703 sensor. Fluorescence images in the upper panels are shown as overlays of two pseudocolor channels, a FRET channel (570/30 nm excitation and 720/60 nm emission) in red and a mKate2 donor channel (570/30 nm excitation and 630/30 nm emission) in green. Lower panels represent pseudocolor images of the ratio between the FRET and donor channels. Scale bar, 10 μm. (e) Time-course of the ratio between the FRET and donor channels for the cells shown in (d).
Figures 7A, 7B, 7C, 7D, 7E, 7F, 7G, 7H, 7I:
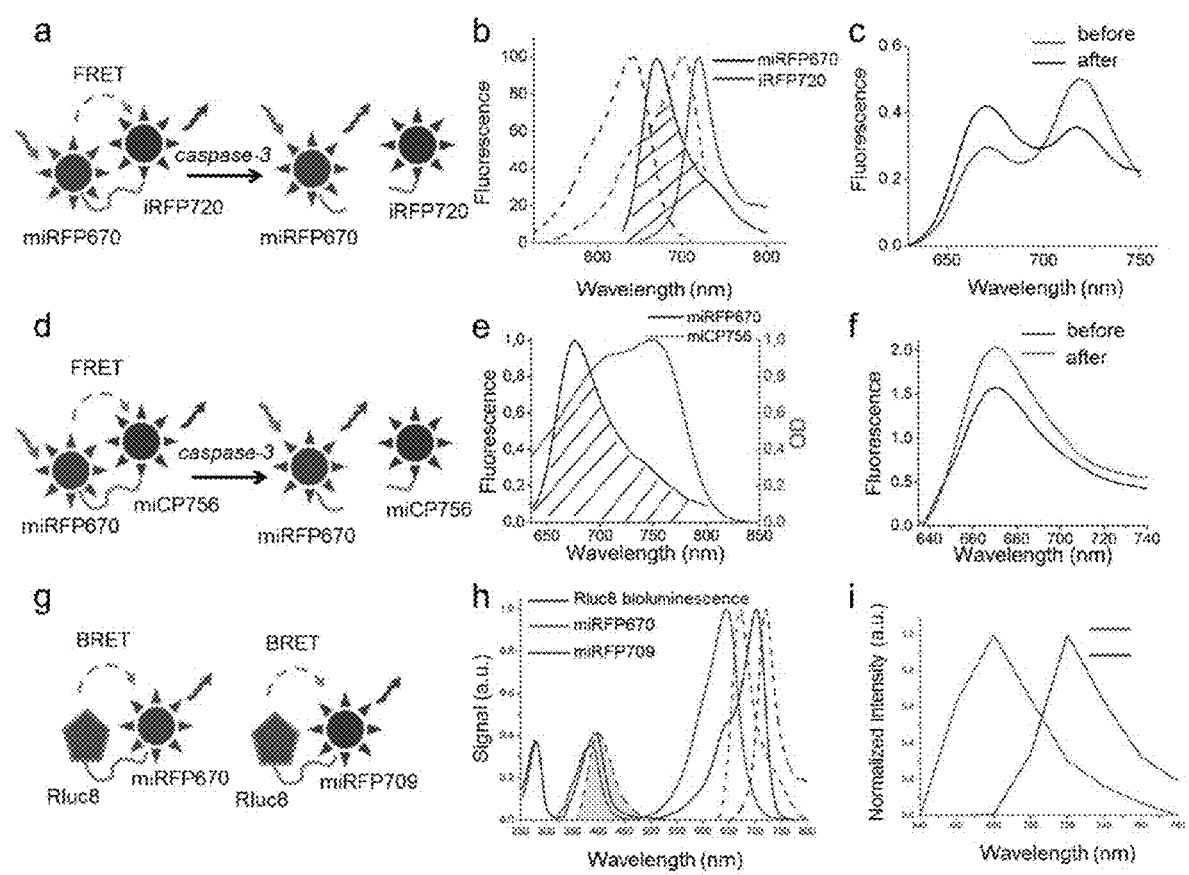
FIG. 7A-7I. Characterization of miRFP fusions with iRFP720, NIR absorbing chromoprotein miCP756, and Renilla luciferase as examples of miRFP-based NIR FRET sensors and NIR BRET reporter. (a,d) Schematic representation of a NIR caspase-3 sensor is shown. miRFP670 (also miRFP703 and miRFP709) can serve as a FRET donor for iRFP720 (a) miCP756. Upon cleavage with caspase-3, miRFP670 donor and the acceptor become separated and, consequently, FRET does not occur. (b) Overlay of the normalized excitation (dashed lines) and emission (solid lines) spectra of the miRFP670 donor and miRFP703 acceptor. (c,f) Emission spectra of the miRFP703-iRFP720 (c) sensor or miRFP670-miCP756 sensor (f) before and 6 h after staurosporine treatment (resulting in reporter proteolysis) measured in a suspension of the transiently transfected HeLa cells. The spectra were acquired with 600 nm excitation and normalized to fluorescence intensity of the acceptor (excited at 650 nm) in the same samples. (e) Overlay of the normalized absorbance spectrum of miCP756 (red line) and emission spectrum of miRFP670 (black line). (g) Schematic representation of a NIR BRET-based luminescent reporter. BRET from RLuc8 to one of miRFPs results in NIR bioluminescence of the chimeras with emission spectra corresponding to miRFPs. (h) An overlay of the bioluminescence spectrum of RLuc8 with Prolum Purple I substrate and absorbance spectra of miRFP670 and miRFP720. (i) Bioluminescence spectra of the miRFP670-Rluc8 and miRFP709-Rluc8 fusion constructs with Prolum Purple I substrate.

Specific examples of the FRET pairs for miRFP-related FPs are provided in FIG. 6-7, 11. The FRET pairs were tested in sensors of protease activity. As one example a sensor for protease activity is provided that is based on the FRET pair between previously known mKate2 and miRFP703 disclosed herein (FIG. 6). The two proteins are connected with a linker containing the protease cleavage site. Cleavage at the protease site separates the two proteins and eliminates FRET between them. Thereby the protease activity is detected. In several embodiments the protease site is a caspase-3 protease site, for example, including the amino acid sequence set forth as DEVD. In some examples the protease sensor is a caspase-3 protease sensor. Another example of a sensor for caspase activity is provided that is based on the FRET pair between previously known iRFP720 and miRFP670 disclosed herein (FIG. 7a-c). One more example is provided that is based on the FRET pair between the NIR absorbing chromoprotein miCP756 and miRFP670 disclosed herein (FIG. 7d-e).

Figures 14A, 14B, 14C, 14D, 14E:
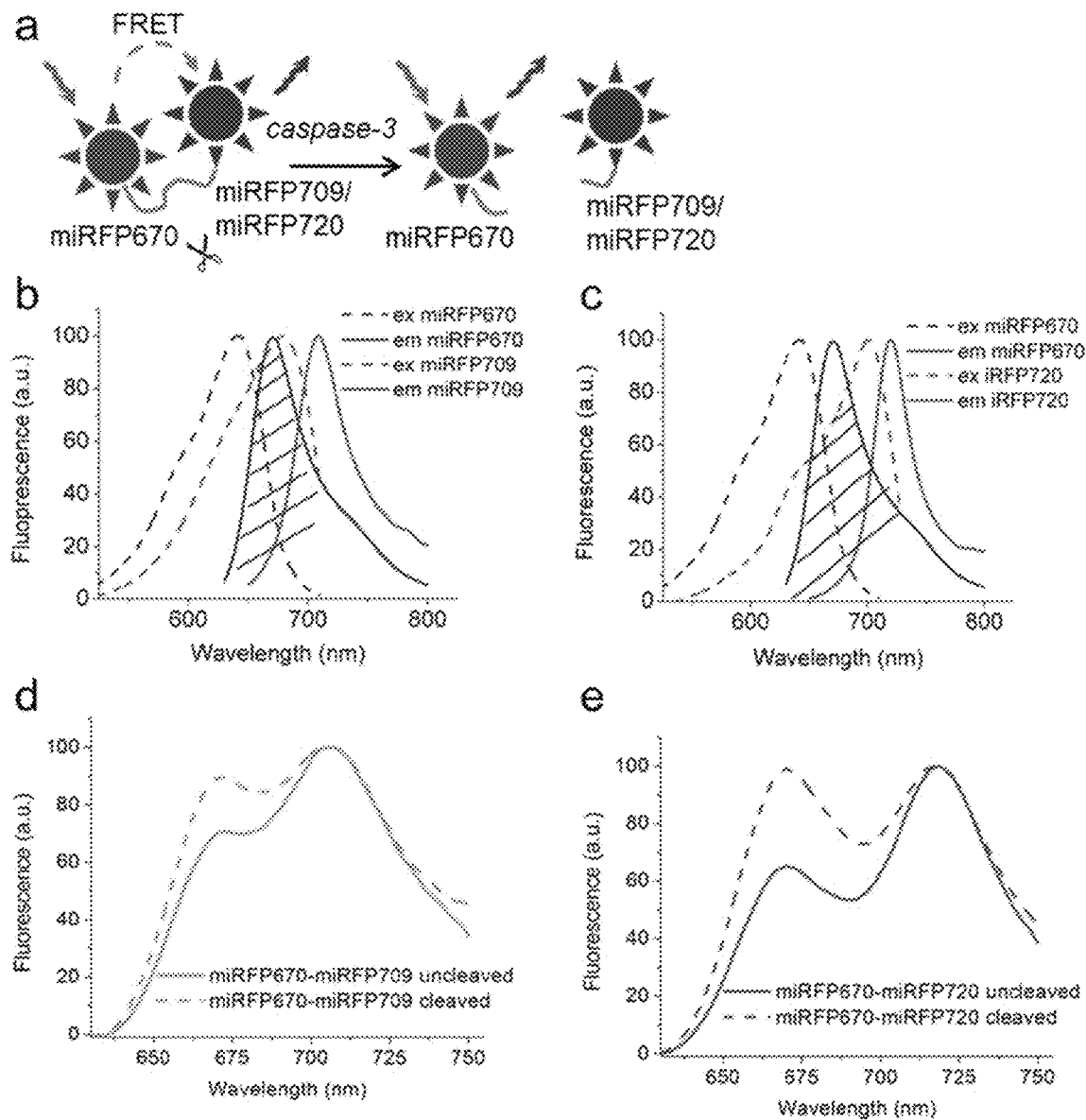
FIG. 14A-14E. Characterization of miRFPs in NIR FRET pairs. (a) Schematics showing characterization of NIR FRET pairs as caspase-3 sensors. The fusion between two miRFPs contains a caspase-3 cleavage site. In an uncleaved fusion, there is FRET from miRFP670 donor to either miRFP709 or miRFP720 acceptor. Upon cleavage, two NIR FPs become separated and FRET does not occur. (b,c) Overlay of the normalized excitation (dashed lines) and emission (solid lines) spectra of the miRFP670 donor and miRFP709 acceptor (b) or miRFP720 acceptor (c). The arrow indicate excitation wavelengths. The shaded areas show overlaps between emission spectra of the donor and excitation spectra of the acceptor. (c,d) Emission spectra of the miRFP670-miRFP709 (c) and miRFP670-miRFP720 (d) sensors before and after cleavage. For cleavage, cells were treated by staurosporine for 6 h after treatment resulting in reporter proteolysis. Fluorescence spectra were measured in a suspension of the transiently transfected HeLa cells. The spectra were acquired with 610 nm excitation and normalized to fluorescence intensity of the FRET channel (fluorescence of acceptor at 709 nm (d) or 720 nm (e)). miRFP670-miRFP720 FRET pair demonstrated 34% changes in the ratio donor-to-FRET after cleavage, comparing to 18% for miRFP670-miRFP709 FRET pair.

Specific examples of the near-infrared FRET pairs comprised of two monomeric FPs of these inventions are provided in FIG. 14. The FRET pairs were tested in sensors of protease activity. As one example a sensor for protease activity is provided that is based on the FRET pair between miRFP670 and miRFP709 disclosed herein (FIG. 14). The two proteins are connected with a linker containing the protease cleavage site. Cleavage at the protease site separates the two proteins and eliminates FRET between them. Thereby the protease activity is detected. In several embodiments the protease site is a caspase-3 protease site, for example, including the amino acid sequence set forth as DEVD. In some examples the protease sensor is a caspase-3 protease sensor. Another example of a sensor for caspase activity is provided that is based on the FRET pair between miRFP670 and miRFP720 disclosed herein (FIG. 14).

Specific examples of where FRET assays employing the subject FPs may be used include, but are not limited to, the detection of PPIs, such as in a mammalian two-hybrid system, transcription factor dimerization, membrane protein multimerization, multiprotein complex formation; as a biosensor for a number of different events, where a peptide or protein covalently links a FRET fluorescent combination including the subject FPs and the linking peptide or protein is, for example, a protease-specific substrate for caspase-mediated cleavage, a peptide that undergoes conformational change upon receiving a signal which increases or decreases FRET, such as a PKA regulatory domain (cAMP-sensor), a phosphorylation site (for example, where there is a phosphorylation site in the peptide or the peptide has binding specificity to phosphorylated/dephosphorylated domain of another protein), or the peptide has Ca2+ binding domain. In addition, fluorescence resonance energy transfer or FRET applications in which the proteins of the present invention find use include, but are not limited to, those described in: U.S. Pat. Nos. 6,008,373; 5,998,146; 5,981,200; 5,945,526; 5,945,283; 5,911,952; 5,869,255; 5,866,336; 5,863,727; 5,728,528; 5,707,804; 5,688,648; 5,439,797; the disclosures of which are herein incorporated by reference.

The FPs of the present invention can advantageously be used in BRET (bioluminescence resonance energy transfer) experiments. In an embodiment, The invention provides a method of producing NIR luminescence signal in a fusion protein comprising (i) consecutive amino acid residues having the sequence set forth in miRFP670v1 (SEQ ID NO: 1), miRFP670 (SEQ ID NO:2), miRFP703 (SEQ ID NO:3), miRFP709 (SEQ ID NO:4), miRFP670-2 (SEQ ID NO: 11), miRFP702 (SEQ ID NO: 12), miRFP682 (SEQ ID NO: 13), miRFP713 (SEQ ID NO:14), or miRFP720 (SEQ ID NO:15) or a protein with 90% or greater identity to one of SEQ ID NOS: 1-4, 11-15, joined at a terminus thereof to Renilla luciferase (RLuc8). Specific examples of the BRET assay for miRFP-related FPs are provided in FIG. 7g-i. Using commercially available Prolum Purple I substrate, which bioluminesces around 400 nm, it is possible to induce bioluminescence resonance energy transfer (BRET) from RLuc8 to miRFPs. Indeed, the emission of Rluc supplemented with Prolum Purple I overlaps with the shorter wavelength Soret band absorbance peak of BphP-based NIR FP containing BV as chromophore (FIG. 7h). Due to BRET from RLuc8 to miRFPs, the resulting NIR bioluminescence of the chimeras has maxima corresponding to the emission maxima of a miRFP-related FPs. This constructs can be used as a protein fusion for multimodality in vivo imaging and as a template for development of sensors of various designs, including Ca2+-sensor and monitoring of PPIs. Specific examples of where BRET assays employing the subject FPs may be used include, but are not limited to the specific examples of the FRET assay describes above.

Methods of using the disclosed FP split fragments and FPs are also provided. For example, the disclosed split fragments are useful in methods of detecting PPIs between a first test polypeptide and a second test polypeptide. For example, as disclosed in Experimental Details, the disclosed miSplit670 and miSplit709 exhibit minimal self-assembly, unless these tags are brought into relatively close proximity with one another, for example by linkage to the N- and C-terminus of the same protein, or by linkage to interacting protein pairs.

The invention provides a method of detecting PPIs between a first test polypeptide and a second test polypeptide, where miRFP-PAS (SEQ ID NO:5) or miRFP-PAS1 (SEQ ID NO:6) is fused to the first polypeptide, and miRFP-GAF670 (SEQ ID NO:7), miRFP-GAF703 (SEQ ID NO:8), or miRFP-GAF709 (SEQ ID NO:9) is fused to the second polypeptide. Detecting the fluorescence of this protein complex detects the PPI between the first and the second test polypeptides.

In some embodiments, a method of detecting a PPI between a first test polypeptide and a second test polypeptide is provided. The method comprises providing a fragment corresponding to the PAS domain of miRFP-related protein or a circular permutant thereof can complement with a fragment corresponding to the GAF domain of miRFP-related protein. A first test polypeptide fused to a fragment corresponding to the PAS domain; and a second test polypeptide fused to a fragment corresponding to the GAF domain. If the first test polypeptide binds to the second polypeptide, then the two fragments will complement to form a FP complex. Complementation of these FP fragments is facilitated by the binding of the first test polypeptide to the second test polypeptide, which brings the SFP split fragments within close proximity to one another. The provided proteins are assayed for fluorescence, and detection of fluorescence detects the PPI.

In an additional embodiment, the first and second test proteins do not interact directly with each other, but instead form a tertiary complex with a third, untagged protein or a nucleic acid molecule. In this embodiment, complementation of the FP split fragments is facilitated by the binding of the first test polypeptide and the second test polypeptide to the third protein or the nucleic acid molecule, which brings the FP split fragments with close proximity to one another.

The proximity of these two tags enhances complementation. In this embodiment, detecting the fluorescence of the complemented split-miRFP-related protein complex detects the protein interaction between the first, second, and third polypeptide or the first, second polypeptides with the nucleic acid molecule.

The FPs of the present invention find use in a method for detecting the effects of a test substance on the regulation of expression and/or translocation of one or more proteins of interest in a cell. Alternatively, they find use in a method for detecting the expression of a protein of interest and the simultaneous activity of an expression control sequence in response to a test substance. The FPs find also use in a method to compare the activity of two or more expression control sequences in a cell in response to a test substance. Such methods may be performed in the presence and in the absence of a test substance whose effect on the process is to be measured.

The FPs of the present invention also find use in applications involving the automated screening of arrays of cells expressing fluorescent reporting groups by using microscopic imaging and electronic analysis. Screening can be used for drug discovery and in the field of functional genomics where the subject proteins are used as markers of whole cells to detect changes in multicellular reorganization and migration, for example in the formation of multicellular tubules (blood vessel formation) by endothelial cells, migration of cells through the Fluoroblok Insert system (Becton Dickinson), wound healing, or neurite outgrowth. Screening can also be employed where the proteins of the present invention are used as markers fused to peptides (such as targeting sequences) or proteins that detect changes in intracellular location as an indicator for cellular activity, for example in signal transduction, such as kinase and transcription factor translocation upon stimuli. Examples include protein kinase C, protein kinase A, transcription factor NFkB, and NFAT; cell cycle proteins, such as cyclin A, cyclin B1 and cyclin E; protease cleavage with subsequent movement of cleaved substrate; phospholipids, with markers for intracellular structures such as the endoplasmic reticulum, Golgi apparatus, mitochondria, peroxisomes, nucleus, nucleoli, plasma membrane, histones, endosomes, lysosomes, or microtubules.

The proteins of the present invention also can be used in high content screening to detect co-localization of other fluorescent fusion proteins with localization markers as indicators of movements of intracellular FPs/peptides or as markers alone. Examples of applications involving the automated screening of arrays of cells in which the subject FPs find use include U.S. Pat. No. 5,989,835; as well as WO 0017624; WO 00/26408; WO 00/17643; and WO 00/03246; the disclosures of which are herein incorporated by reference.

The FPs of the present invention also find use in high throughput screening assays. The subject FPs are stable proteins with half-lives of more than 24 hours. Also provided are destabilized versions of the subject FPs with decreased half-lives that can be used as transcription reporters for drug discovery. For example, a protein according to the subject invention can be fused with a putative proteolytic signal sequence derived from a protein with shorter half-life, such as a PEST sequence from the mouse ornithine decarboxylase gene, a mouse cyclin B1 destruction box or ubiquitin, etc. For a description of destabilized proteins and vectors that can be employed to produce the same, see e.g., U.S. Pat. No. 6,130,313; the disclosure of which is herein incorporated by reference. Promoters in signal transduction pathways can be detected using destabilized versions of the subject FPs for drug screening such as, for example, AP1, NFAT, NFkB, Smad, STAT, p53, E2F, Rb, myc, CRE, ER, GR and TRE, and the like.

The subject proteins can be used as second messenger detectors by fusing the subject proteins to specific domains such as the PKCgamma Ca-binding domain, PKCgamma DAG binding domain, SH2 domain or SH3 domain, etc.

Secreted forms of the subject proteins, which in turn can be used in a variety of different applications can be prepared by fusing secreted leading sequences to the subject proteins.

The subject proteins also find use in fluorescence activated cell sorting (FACS) applications. In such applications, the subject FP is used as a label to mark a population of cells and the resulting labeled population of cells is then sorted with a fluorescence activated cell sorting device, as is known in the art. FACS methods are described in U.S. Pat. Nos. 5,968,738 and 5,804,387; the disclosures of which are herein incorporated by reference.

The subject proteins also find use as in vivo labels in transgenic animals. For example, expression of the subject protein can be driven by tissue-specific promoters, where such methods find use in research for gene therapy, such as testing efficiency of transgenic expression, among other applications. A representative application of FPs in transgenic animals that illustrates such applications is found in WO 00/02997, the disclosure of which is herein incorporated by reference.

Additional applications of the proteins of the present invention include use as markers following injection into cells or animals and in calibration for quantitative measurements; as markers or reporters in oxygen biosensor devices for monitoring cell viability; as markers or labels for animals, pets, toys, food, and the like.

The subject FPs also find use in protease cleavage assays. For example, cleavage-inactivated fluorescence assays can be developed using the subject proteins, where the subject proteins are engineered to include a protease-specific cleavage sequence without destroying the fluorescent character of the protein. Upon cleavage of the FP by an activated protease, fluorescence would sharply decrease due to the destruction of the functional chromophore. Alternatively, cleavage-activated fluorescence can be developed using the proteins of the present invention where the proteins are engineered to contain an additional spacer sequence in close proximity/or inside the chromophore. This variant is significantly decreased in its fluorescence activity, because parts of the functional chromophore are divided by the spacer. The spacer is framed by two identical protease-specific cleavage sites. Upon cleavage via the activated protease, the spacer would be cut out and the two residual "subunits" of the FP would be able to reassemble to generate a functional FP. Both of the above applications could be developed in assays for a variety of different types of proteases, such as caspases and others.

The subject proteins also can be used in assays to determine the phospholipid composition in biological membranes. For example, fusion proteins of the subject proteins (or any other kind of covalent or non-covalent modification of the subject proteins) that allows binding to specific phospholipids to localize/visualize patterns of phospholipid distribution in biological membranes, while allowing co-localization of membrane proteins in specific phospholipid rafts, can be accomplished with the subject proteins.

The subject FPs also find use as biosensors in prokaryotic and eukaryotic cells, such as a $Ca^{2+}$ ion indicator; a pH indicator; a phosphorylation indicator; or as an indicator of other ions, such as magnesium, sodium, potassium, chloride and halides. Methods of using FPs as biosensors also include those described in U.S. Pat. Nos. 5,972,638; 5,824,485 and 5,650,135 (as well as the references cited therein) the disclosures of which are herein incorporated by reference.

The subject FPs also find use as biosensors, sources of circularly permuted FPs and biosensors thereof. Methods of preparation and use of circularly permuted FPs are described in (35-37) and U.S. Pat. Nos. 6,469,154 and 6,699,687, the disclosures of which are herein incorporated by reference. The biosensors can be used in prokaryotic and eukaryotic cells, such as a Ca2+ ion indicators, a pH indicator, a phosphorylation indicator, other enzyme activity indicators, or as an indicator of ions, such as magnesium, sodium, potassium, chloride, halides, etc. Methods of using FPs as biosensors also include those described in U.S. Pat. Nos. 5,972,638, 5,824,485, and 5,650,135 (as well as the references cited therein) the disclosures of which are herein incorporated by reference.

The subject FPs also find use as labels for photoacoustic imaging. Upon provision of the light stimulus, the FPs of the invention are either excited and subsequently emit a fluorescence signal as described above, or they absorb the energy provided by the stimulus, which may be measured by detecting the temperature change associated with this absorption. Detecting the temperature change of the polypeptide or fusion protein upon absorption of the light stimulus is also known in the art under the term "photoacoustic or optoacoustic methods", and is based on absorption of the stimulus, which leads to a local heating and accompanying local expansion. This local expansion leads to ultrasonic pressure waves that can be recorded using high frequency pressure sensors (38-40).

Kits

Also provided by the present invention are kits for use in practicing one or more of the above-described applications. Kits typically include the protein of the invention as such, or a nucleic acid encoding the same preferably with the elements for expressing the subject proteins, for example, a construct such as a vector comprising a nucleic acid encoding the subject protein. In preferred embodiments kits may be used for monitoring of inflammation, cell cycle, apoptosis within living cells, subcellular structures or protein around. In other embodiments kits may be used for labeling of cells, subcellular structures or proteins.

The kit components are typically present in a suitable storage medium, such as a buffered solution, typically in a suitable container. Also present in the kits may be antibodies specific to the provided protein. In certain embodiments, the kit comprises a plurality of different vectors each encoding the subject protein, where the vectors are designed for expression in different environments and/or under different conditions, for example, constitutive expression where the vector includes a strong promoter for expression in mammalian cells or a promoterless vector with a multiple cloning site for custom insertion of a promoter and tailored expression, etc.

In addition to the above components, the subject kits will further include instructions for practicing the subject methods. These instructions may be present in the subject kits in a variety of forms, one or more of which may be present in the kit.

The following examples are offered by way of illustration and not by way of limitation.

Method of Monomerization of BphP-Derived FPs

The present invention provides variant FPs that have a reduced propensity to oligomerize due to the presence of at least four mutations in the C-terminus of the FP (FIG. 11). As disclosed herein, the positions of the mutations were found from the evolution of RpBphP1 and development of miRFP670v1 (SEQ ID NO:1), miRFP670 (SEQ ID NO:2), miRFP703 (SEQ ID NO:3), or miRFP709 (SEQ ID NO:4). The position numbers are 300, 301, 304, 305, 308, as numbered according to RpBphP1, i.e. SEQ ID NO: 10. The corresponding positions in other FPs are derived from alignment with RpBphP1. This strategy for producing monomeric FPs from various BphPs and NIR FPs involved introduction of charged residues (D, E, K, or R) at the positions 300, 301, 304, 305 and residues T, S, G, A at position 308 to prevent dimer formation (FIG. 9,10).

Figures 13A, 13B:
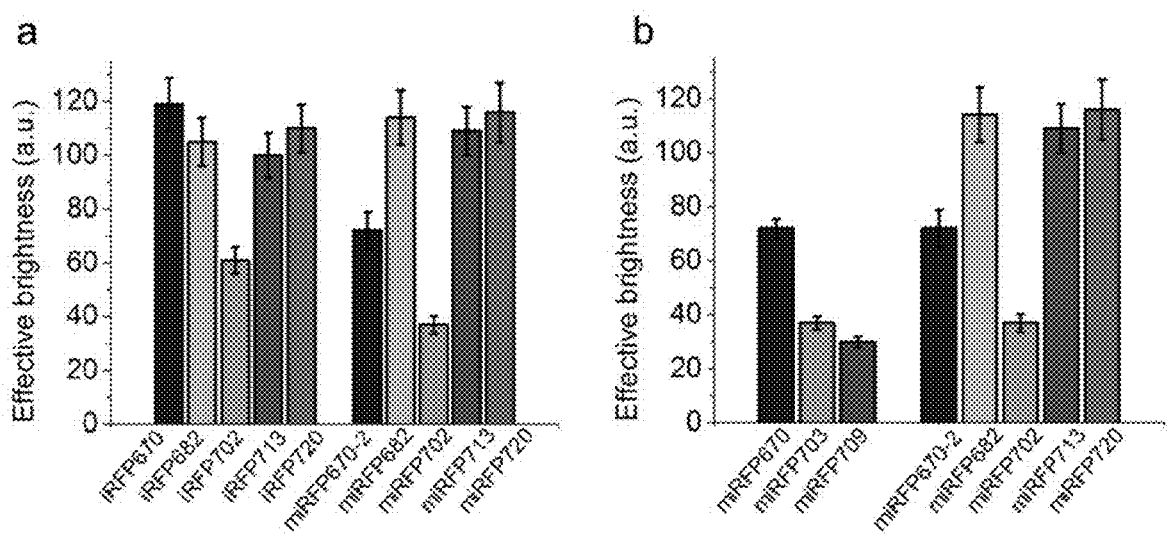
FIG. 13A-13B. Brightness of miRFPs in mammalian cells. (a) Brightness of live HeLa cells transiently transfected with monomerized iRFPs comparing to dimeric iRFPs (b) Brightness of all miRFPs provided in this invention. (a,b) Live HeLa cells transiently transfected with FPs were analyzed by flow cytometry. The NIR fluorescence intensity was normalized to transfection efficiency (fluorescence of co-transfected EGFP), to excitation efficiency of each FP with 635 nm laser, and to fluorescence signal of each FP in the emission filter. It was also normalized to brightness of cells expressing dimeric iRFP713 that is assumed to be 100%. Error bars, s.d. (n=3; transfection experiments).

The presented strategy is unique comparing to the other strategies reported before (3, 9) (FIG. 10), since it results in no loss of brightness or loss of brightness by no more than 50% of the resulting monomeric FP, compared with the corresponding dimeric FP (FIG. 13a). The basic strategy for decreasing the oligomeric state is similar to reported before and incudes a replacement of residues participating in dimeric interface with the charged (D, E, K, R) or small residues (G, S). However, the specific positions are different. The previous attempts to break the dimeric interface by introducing charged residues in positions 301, 305, 312 and small neutral residue at 308 (3), charged residue at 312 (18), or small residue at position 139 and two charged residues at positions 305 and 308 (9) resulted either in FPs that have low brightness in mammalian cells (3, 9) or that still behaved as dimers (17, 18). Amino acid numbering is given according to alignment with RpBphP1.

The method of the present invention is supported by the illustrative examples of the monomerized iRFP NIR FPs, which were obtained by the introducing of the charged residues (D, E, K, or R) at the positions 300, 301, 304, 305 and residues T, S, G at position 308, as numbered according to RpBphP1, i.e. SEQ ID NO: 10. According to the alignment in FIG. 9, the specific mutations in iRFPs developed from RpBphP6 (miRFP670 and miRFP702, SEQ ID NOs: 11-12) were K295, R296, E298, R299, T302. Furthermore, the invention also provides a possibility to introduce other charged and small amino acid residues in these positions, i.e. D295, E295, K295, R295, D296, E296, K296, R296, D298, E298, K298, R298, D299, E299, K299, R299, T302, S302, G302, and A302, and wherein the amino acid positions correspond to SEQ ID NOs: 11-12. According to the alignment in FIG. 9, the specific mutations in iRFPs developed from RpBphP2 (miRFP682, miRFP713, miRFP720, SEQ ID NOs:13-15) were K301, R302, E305, R306, T309. Furthermore, the invention also provides a possibility to introduce other charged and small amino acid residues in these positions, i.e. D301, E301, K301, R301, D302, E302, K302, R302, D305, E305, K305, R305, D306, E306, K306, R306, T309, S309, G309, and A309, and wherein the amino acid positions correspond to SEQ ID NOs:13-15.

It is contemplated that the monomerization method provided by the present invention can be used to generate NIR FPs that have reduced propensity to oligomerize from other dimeric NIR FPs and during evolution from other BphP templates. It is known in the art that RpBphP1, RpBphP2, and RpBphP6 used as templates for development of miRFPs are members of the a family of related BphP homologous proteins sharing high degree of protein structure at the C-terminus, including the C-terminus responsible for dimerization. If monomeric versions of these proteins are additionally advantageous since they have the ability to fluoresce at different wavelengths then the reported miRFPs. These potential monomeric NIR FPs will find use as fluorescent markers and in applications disclosed in this invention, similar to miRFPs. BphPs that can be used to develop bright monomeric NIR FPs include DrBphP, BrBphP, and RpBphP1-6 and others.

EXPERIMENTAL DETAILS AND EXAMPLES

Introduction

Current BphP-based NIR FPs have limitations and cannot be used to label proteins and to build NIR biosensors. There are three characteristics of NIR FPs, which are crucial to consider for their applications (1). The first one is an effective brightness of NIR FP in mammalian cells, which depends on its molecular brightness, intracellular stability, efficiency of BV incorporation, and cell expression level. In contrast to GFP-like FPs, the effective brightness of BphP-based NIR FPs does not always correlate with their molecular brightness (1). Decreased cellular fluorescence of some NIR FPs results from a low specificity of BV binding and a competition between BV and other heme-derived compounds, including protoporphyrin IX, for binding to NIR FP apoproteins (13, 14). The second characteristic to consider is an oligomeric state of FPs. Only monomeric FPs can be used in protein fusions without interference with functionality of the tagged protein partner (15). The third characteristic is the spectral properties of NIR FPs. Spectrally distinct NIR FPs are required for biosensors and for multicolor NIR labeling.

Among the reported BphP-based FPs, five spectrally distinct NIR FPs, iRFP670, iRFP682, iRFP702, iRFP713 and iRFP720 (1, 4, 16) fully rely on endogenous BV and do not require its external supply or co-expression of heme oxygenase (HO). Therefore, these proteins can be used as easy as GFP-like FP by delivering a single gene to cells. Importantly, possible endogenous BV concentration variability does not influence performance of iRFPs. Indeed, iRFP713 fluorescence was observed in all tissues of two iRFP713-transgenic mouse lines (8). In both mouse lines, the iRFP713 fluorescence intensity was generally uniform in almost all organs and tissues, with slightly higher expression levels in liver, lungs, and pancreas. However, iRFPs are dimers and can mainly serve for labeling of organelles and whole cells.

The first monomeric BphP-based FP, IFP1.4 (3), is dim and do not fluoresce without a BV supply. Moreover, it forms dimers, as was found recently (17). Its brighter version IFP2.0 (18) was also found to be dimeric (1, 17). Previously reported monomeric FPs, Wi-Phy (9) and IFP1.4rev (19), were characterized only in vitro (9, 19). Recently reported monomeric mIFP (17), which is the only one monomeric FP tested in cellular fusions, is dimmer than dimeric iRFPs and requires a supply of BV via co-expression of BV-producing enzyme, HO. Also, a lack of spectrally distinct versions of monomeric BphP-based FPs prevents two-color NIR protein labeling and a development of NIR reporters and biosensors.

Here a set of bright spectrally distinct monomeric NIR FPs are disclosed termed miRFP670v1, miRFP670, miRFP703, miRFP709, which fully rely on endogenous BV to fluoresce in mammalian cells and mammals, are disclosed. We disclose the use of these miRFPs in a wide range of NIR protein tags, reporters and biosensors.

Based on the success in development of bright monomeric NIR FPs from RpBphP1 template by introducing mutations in specific positions at the C-terminus, we decided to explore the mutation of these residues as a general method of monomerization of BphP-derived NIR FPs. By introduction of specific mutations on C-termini of dimeric iRFPs, we were able to convert these FPs into monomeric versions with no or minimum decrease in effective brightness in mammalian cells. Since previous approaches for NIR FP monomerization led to either considerable decease in brightness or FPs that still behave like dimers at higher concentrations, the present work provides a general approach to monomerization of NIR FPs developed from BphPs. It also reports a set of new bright monomeric iRFPs, developed from dimeric iRFPs, termed miRFP670-2, miRFP682, miRFP702, miRFP713, and miRFP720.

Together with miRFPs developed from RpBphP1, miRFPs obtained by monomerization of dimeric iRFPs developed from RpBphP2 and RpBphP6 provide a useful tools as NIR FP tags and components of NIR reporters and biosensors for applications across spatial scales: from microscopy and flow cytometry to whole-body imaging.

Results

Molecular evolution and screening for miRFPs. To engineer miRFPs, we chose the chromophore-binding PAS-GAF domains of RpBphP1 as a starting point for molecular evolution. Structure of the full-length dimeric RpBphP1 (41) indicates that the PAS-GAF domains do not participate in a dimer interaction (FIG. 1a). We first randomly mutated Asp201 and Ile202 residues, which were shown to stabilize BV chromophore and to increase fluorescence quantum yield (9, 16). Then, we subjected the PAS-GAF domains to random mutagenesis with screening in E. coli bacteria co-expressing HO for BV production, as described (16).

Since NIR FP brightness in the HO overexpressing bacteria does not always correlate with the brightness of the proteins in mammalian cells where BV concentration is lower, we tested effective brightness of protein mutants, found during each round of molecular evolution in bacteria, in mammalian cells and discarded the NIR FP variants with the low brightness.

To develop truly monomeric FPs, we specifically focused on residues in the C-terminal α-helix of the GAF domain, which formed dimerization interface in other NIR FPs (9). To exclude formation of even weak dimers, we additionally mutated residues in the C-terminal α-helix of the mutants obtained after the fourth round. Then, to select the monomeric variants, we tested the bright variants using a size exclusion chromatography and further verified their performance in α-tubulin fusions in mammalian cells.

To develop spectrally distinct FPs, we applied the reported rational design strategy (25). It has been shown that blue-shifted BphP-based NIR FPs can be obtained by substituting the Ile residue with Cys in the -PIH- motif in the GAF domain (25). This Cys residue is able to form a covalent bond with BV, resulting in ~40 nm spectral blue-shift. By replacing this Cys with original Ile, the blue-shifted NIR FP can be converted to standard red-shifted NIR FP with BV bound to a conserved Cys residue in the PAS domain. Earlier we also found that residues in positions 201 and 202 in -PXSDIP- motif are not only involved in stabilization of BV chromophore but additionally influence spectral properties of FPs (16).

As a result, we have obtained miRFP670 (excitation/emission at 642 nm/670 nm) having Cys in the GAF domain and its dimmer version miRFP670v1 (Table 1). By changing Cys back to Ile and mutating residues 201 and 202, we found two red-shifted variants, miRFP703 (excitation/emission at 673 nm/703 nm) and miRFP709 (excitation/emission at 686 nm/709 nm) (Table 1). These three miRFPs exhibit excitation and emission maxima covering the spectral ranges of 642-683 nm and 670-709 nm, respectively (FIG. 1b,c). Absorbance of miRFPs was characterized by small side peaks at 280 nm (protein absorbance) and 390 nm (so called Soret band common to all tetrapyrrole compounds) and by large main peaks at 644 nm, 676 nm and 685 nm, indicative of the efficient BV incorporation. Monomeric states of miRFPs was confirmed by a size exclusion chromatography at 1 mg/ml as well as at concentrations as high as 30 mg/ml (FIG. 1d).

Detailed characterization of miRFPs. Molecular brightness (the product of a molar extinction coefficient and quantum yield) of miRFP670 and miRFP703 was higher than and of miRFP709 was close to the molecular brightness of dimeric iRFP713 (Table 1). Interestingly, miRFP670 exhibited a fluorescence quantum yield of 14%, which is the highest for available BphP-based FPs with BV chromophore. miRFPs were brightest at pH values between 5 and 8, and all had pKa of 4.5. All miRFPs exhibited several-fold higher photostability than mIFP in mammalian cells (Table 1).

We further studied an effective brightness of miRFPs in live mammalian cells. Although less bright than dimeric iRFPs (Table 1), all miRFPs considerably outperformed IFP2.0 and mIFP. The dimmest miRFP709 was >2-fold brighter and the brightest miRFP670 was >5-fold brighter than mIFP in HeLa cells (FIG. 1e,f). Cell images indicate homogenous distribution of miRFPs and absence of intracellular aggregates. miRFPs require less exposure time than mIFP or IFP2.0 to reach comparative cellular brightness (FIG. 1f). The effective brightness of miRFP703 was also higher than mIFP in other mammalian cells including HEK293, U87, U2OS, Cos-1. Thus, possible variability of BV levels in different cell lines does not influence the performance of miRFPs.

To study maturation of miRFP proteins, which includes protein synthesis, protein folding and BV chromophore binding, we monitored the NIR fluorescence growth in *E. coli* bacteria upon a pulse-chase induction of the protein expression. The half-times of this process were ~200 min for all three miRFPs. Next, we separately studied kinetics of BV binding and its dependence on BV concentration. For this, we measured the kinetics of assembly of purified miRFP670 apoprotein with different concentrations of free BV in vitro. The binding half-times for 15 µM apoprotein and 0.1 µM, 1 µM and 10 µM of BV were 3.5 min, 1.8 min, and 1.2 min, respectively. At all BV concentrations, the miRF670 holoprotein was fully assembled in 20 min. We concluded that miRFPs mature relatively fast, with the protein folding being the slowest step.

TABLE 1

Selected NIR FPs engineered from BphPs with the demonstrated in vivo applications.

| NIR FP | Ex, nm | Em, nm | Extinction coefficient, $M^{-1}cm^{-1}$ | Quantum yield, % | Molecular brightness vs. iRFP713, % | Oligomeric state | Photostability in mammalian cells, $t_{1/2}$, s | pKa | Brightness in HeLa cells vs. iRFP713, %[a] | Ref |
|---|---|---|---|---|---|---|---|---|---|---|
| miRFP670v1 | 644 | 670 | 71,300 | 11.6 | 134 | monomer | 490 (155) | 4.5 | 30 | (42) |
| miRFP670 | 642 | 670 | 87,400 | 14.0 | 198 | | 490 (155) | 4.5 | 72 | |
| miRFP703 | 674 | 703 | 90,900 | 8.6 | 127 | | 650 (394) | 4.5 | 37 | |
| miRFP709 | 683 | 709 | 78,400 | 5.4 | 69 | | 500 (192) | 4.5 | 30 | |
| mIFP[b] | 683 (683) | 705 (704) | 65,900 (82,000) | 6.9 (8.4) | 74 | monomer | 90 (54) | 4.5 | 15 | (17) |
| IFP2.0[b,c] | 688 (690) | 709 (711) | 72,900 (98,000) | 6.8 (8.1) | 80 | dimer[d] | 150 (108) | 4.5 | 8 | (18) |
| iRFP670 | 643 | 670 | 114,000 | 12.2 | 225 | dimer | 290 | 4.5 (4.0) | 119 | (16) |
| iRFP682 | 663 | 682 | 90,000 | 11.1 | 162 | | 490 | 4.5 | 105 | |
| iRFP702 | 673 | 702 | 93,000 | 8.2 | 124 | | 630 | 4.5 | 61 | |
| iRFP713 (aka iRFP) | 690 | 713 | 98,000 | 6.3 | 100 | | 960 | 4.5 | 100 | (4) |
| iRFP720 | 702 | 720 | 96,000 | 6.0 | 93 | | 490 | 4.5 | 110 | (16) |
| miRFP670-2 | 643 | 670 | 103,000 | 13.6 | 227 | monomer | 310 | 4.5 | 72 | here |
| miRFP682 | 663 | 682 | 91,000 | 11.2 | 165 | | 500 | 4.5 | 117 | |
| miRFP702 | 673 | 702 | 88,000 | 8.1 | 115 | | 640 | 4.5 | 37 | |
| miRFP713 | 690 | 713 | 99,000 | 7.0 | 112 | | 980 | 4.5 | 109 | |
| miRFP720 | 702 | 720 | 98,000 | 6.1 | 97 | | 510 | 4.5 | 121 | |

[a]Determined as effective NIR fluorescence in transiently transfected live HeLa cells with no supply of exogenous BV and after normalization to fluorescence of co-transfected EGFP.
[b]Characteristics of NIR FPs shown in original publications are in parentheses. Parameters determined in this work are shown without parentheses.
[c]Only IFP2.0 is presented as the latest version in a series of the IFP proteins (18).
[d]Although IFP2.0 was originally reported as a monomer (18), later it was found to be a dimer (1), which was also confirmed by its developers (17).

To test for cytotoxicity, we monitored stability of miRFP fluorescence over cell generations (43). This characteristic is crucial for long-term FP applications in vivo. Cell labeling typically employs strong promoters, and consequently cells containing high levels of FPs may show growth defects or instability of FP expression (43, 44). Preclonal mixtures of HEK293 cells stably expressing miRFPs under CMV promoter were analyzed before and after three weeks of culturing. The cells retained more than 75% of their initial fluorescence intensity that is comparable to dimeric iRFPs (16) and to the least cytotoxic far-red GFP-like protein, E2-Crimson (4, 45).

Figures 2A, 2B, 2C, 2D:
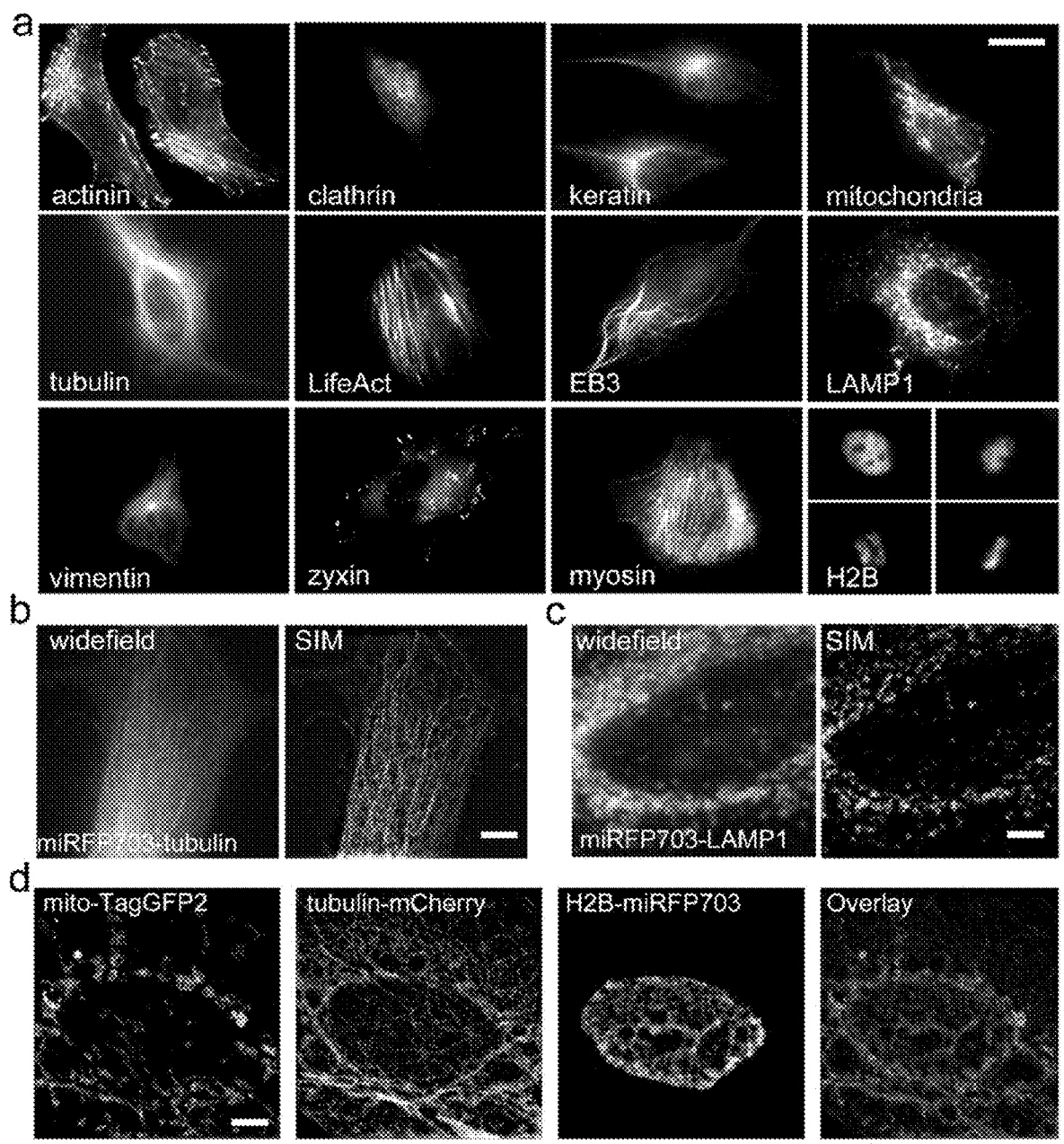
FIG. 2A-2D. miRFP fusions visualized by widefield and super-resolution microscopy. (a) Live HeLa cells transiently transfected with the miRFP703 N- and C-terminal fusion constructs. The N-terminal fusions are α-actinin, keratin, vimentin and tubulin-binding EB3, mitochondrial, focal adhesion protein zyxin, lysosomal membrane glycoprotein LAMP1, vesicular protein clathrin, actin-binding LifeAct and histone H2B. The C-terminal fusions are α-tubulin and myosin. (b, c) Widefield and structured illumination microscopy (SIM) imaging of fixed HeLa cells expressing α-tubulin (b) and LAMP1 (c) labeled with miRFP703. (d) Three-color SIM of fixed HeLa cells expressing mitochondria labeled with TagGFP2, α-tubulin labeled with mCherry, and H2B labeled with miRFP703. Scale bars, 5 am.

We found that miRFPs also can be imaged in primary cell cultures such as neurons. Rat hippocampal neurons transfected with miRFPs exhibited bright homogenous fluorescence without HO co-expression or supplying of exogenous BV, in contrast to IFP2.0 and mIFP, which required the co-expression of HO in neuronal cells (17, 18).

miRFPs as protein tags for conventional and super-resolution microscopy. To test performance of miRFPs as protein tags, we expressed several miRFP fusions in mammalian cells. Both N- and C-terminal fusions localized properly, including those associated with or forming filaments, such as keratin, α-tubulin, α-actinin, LifeAct, EB3, myosin, vimentin, as well as the fusions targeted to various compartments such as clathrin, lysosome-associated membrane protein LAMP1, zyxin (focal adhesions) and mitochondrial signal. (FIG. 2a). The miRFP fusion with histone 2B localized properly in all phases of mitosis and did not affect cell division. Moreover, two spectrally distinct miRFP fusions can be distinguished in the same cell by using two common filter sets.

Next we studied if miRFP fusions can be imaged beyond the diffraction limit. For this, we applied structured illumination microscopy (SIM) to image miRFP703-tagged α-tubulin and LAMP1 (FIG. 2b,c). SIM technique has allowed a better resolution of α-tubulin filaments than widefield microscopy (FIG. 2b). Almost twice more filaments were detected in a cross-section of the SIM image compared to those visible in the wide-field image. The fine circle-like structure of the LAMP1-labelled lysosomes was also visible with SIM (FIG. 2c). miRFPs are good candidates for a crosstalk-free super-resolution imaging with green and red FPs. The three-color SIM enabled simultaneous visualization of TagGFP2-labeled mitochondria, mCherry-labeled α-tubulin and miRFP703-labeled histone 2B in a cell (FIG. 2d).

Monomeric spectrally distinct reporters for PPIs. To explore miRFPs in NIR biosensors design, we first applied them to development of the first monomeric NIR BphP-based BiFC reporters for PPIs. Previous BphP-based complementation reporters were engineered either from dimeric iRFP713 (21, 24) or from weakly dimeric dim IFP1.4 (22, 23). These reporters consist of the PAS domain and the GAF domain fragments fused to two proteins of interest. If the proteins interact, they bring together the PAS and GAF domains, which reconstitute fluorescence.

Figures 3A, 3B, 3C, 3D, 3E, 3F, 3G:
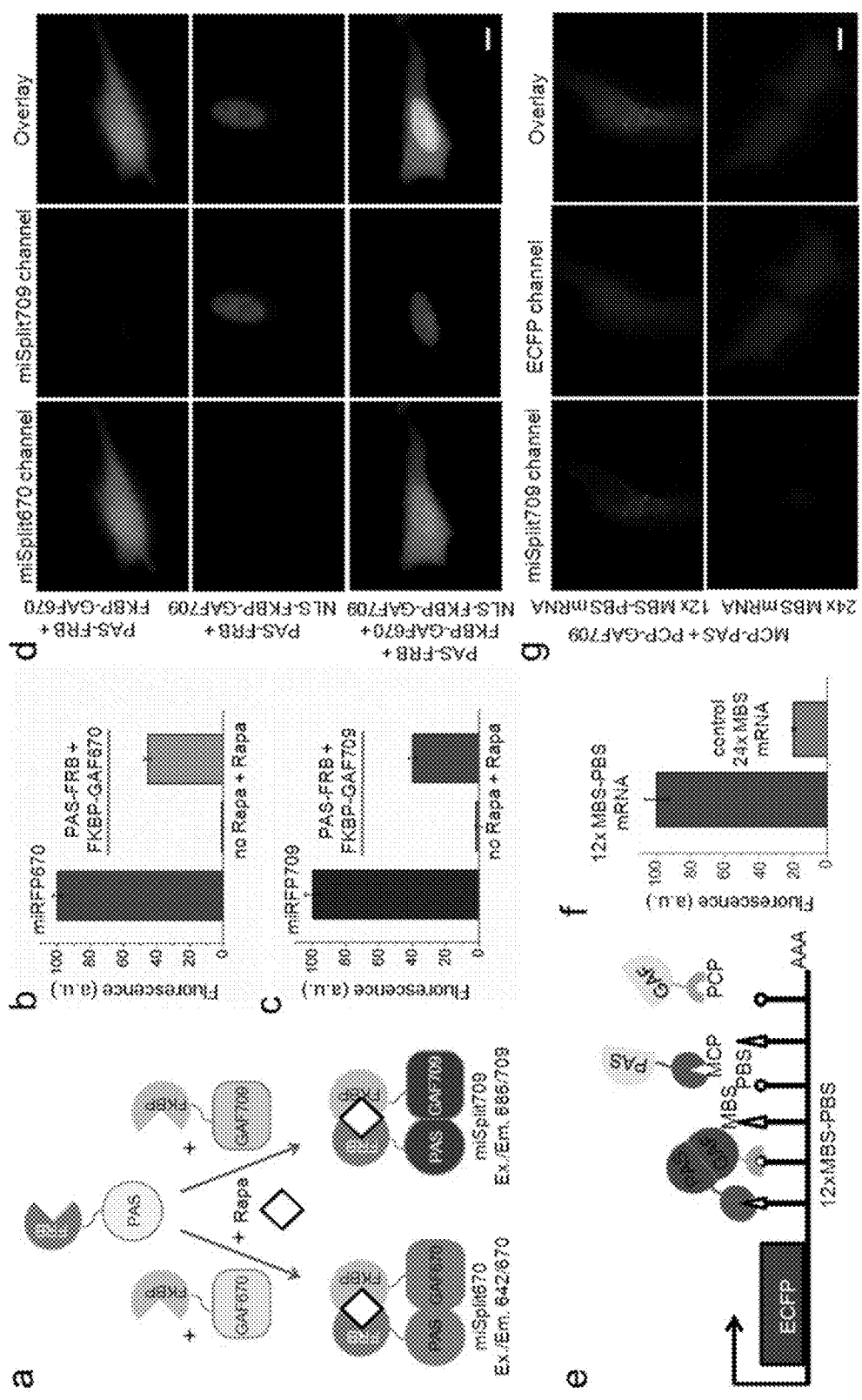
FIG. 3A-3G. Two bimolecular fluorescence complementation (BiFC) monomeric miSplit reporters. (a) Schematics of design and application of miSplit670 and miSplit709 reporters for protein-protein interaction (PPI). The two mSplits share the same miRFP-PAS fragment that can interact with either miRFP-GAF670 or miRFP-GAF709 fragments producing the fluorescence signal corresponding to complemented miSplit670 or miSplit709, respectively. (b, c) Brightness and complementation contrast of miSplit670 (b) and miSplit709 (c) in live HeLa cells. HeLa cells were transiently transfected with the plasmids encoding the indicated proteins. Rapamycin (Rapa) was added where indicated. The mean fluorescence intensities of cells were analyzed by flow cytometry. Error bars, s.d. (n=3; transfection experiments). (d) Two-color imaging of two alternative PPIs in one cell. Transiently transfected HeLa cells expressed cytoplasmic FRB fused to miRFP-PAS together with either cytoplasmic FKBP fused to miRFP-GAF670 (top) or nuclear FKBP fused to miRFP-GAF709 (middle), or both (bottom) of FKBP-fusions. Pseudocolor images (miSplit670 channel in green and miSplit709 channel in red) and the overlays are shown. (e) Schematics of the approach for NIR low-background RNA imaging. RNA (here mRNA encoding ECFP) is tagged with pairs of RNA-binding motifs, MBS and PBS, which bind bacteriophage coat proteins MS2 (MCP) and PP7 (PCP), respectively. MCP and PCP are fused with two fragments of miSplit reporter. mRNA serves as a scaffold to bring two split fragments together and reconstitute fluorescence. (f) mRNA detection with miSplit709. Live HeLa cells co-expressed MCP fused to miRFP-PAS and PCP fused to miRFP-GAF709 together with ECFP mRNA tagged with 12×MBS-PBS binding sites. ECFP mRNA tagged with 24×MBS binding sites served as a control. The mean fluorescence intensities of cells were analyzed by flow cytometry. Error bars, s.d. (n=3; transfection experiments). (g) Representative images of live HeLa cells analyzed in (f). Pseudocolor images (miSplit709 channel in red and ECFP channel in blue) and the overlay are shown for ECFP mRNA with 12×MBS-PBS (top) and ECFP mRNA with 24×MBS (bottom). Scale bars, 10 m.

Starting from miRFPs, we engineered two monomeric miSplit reporters (FIG. 3). For this, we cut mRFP670 and miRFP709 between their PAS and GAF domains. The unique feature of the resulting two miSplits, miSplit670 and miSplt709, is that they share the same PAS domain, whereas the GAF domains differ (FIG. 3a). The miRFP670-PAS domain can interact with either miRFP-GAF670 or miRFP-GAF709, resulting in the miRFP670 or miRFP709 reconstitution, respectively.

We first characterized mi Splits using a rapamycin-induced PPI of FRB and FKBP proteins. We fused FRB to the miRFP-PAS domain and FKBP to either miRFP-GAF670 or miRFP-GAF709 domains and tested their effective brightness and BiFC contrast (the ratio between a stimulus-induced fluorescence signal and a fluorescence signal originated from non-specific complementation) in mammalian cells. Both miSplits retained the >40% of effective brightness of parental full-length miRFPs (FIG. 3b,c) and demonstrated the high complementation contrast of >20-fold (FIG. 3b,c). We next studied the BiFC contrast increase in cells upon induction of rapamycin-dependent FRB-FKBP interaction. We found that the BiFC contrast of 2-fold was achieved as early as 0.5 h after rapamycin addition. Similar to the iRFP713-based BiFC reporters including dimeric iSplit (21) the complementation of miSplits was irreversible. However, compared to iSplit, both miSplits produced the >4-fold lower background and the substantially higher BiFC contrast in the same conditions. The effective brightness of miSplit670 and miSplit709 was 60% and 170% of the brightness of dimeric iSplit, respectively.

Since the PAS domain is the same for both miSplits we next studied whether both miSplits can be used in the same cell. We added a nuclear localization signal (NLS) to FKBP fused with miRFP-GAF670 and co-expressed FRB fused with miRFP-PAS with either FKBP fused to miRFP-GAF670 or NLS-FKBP fused to miRFP709, or with both FKBP fusions (FIG. 3d). We found that similarly to parental miRFP670 and miRFP709, miSplit670 and miSplit709 can be separately imaged in a cell. Thus, miSplits can be applied to discriminate between interaction of one protein fused to the miRFP-PAS domain with two different proteins fused to the miRFP-GAF670 and miRFP-GAF709 domains, respectively.

As a method of RNA detection, BiFC provides lower background of RNA imaging than RNA detection with full-length FPs fused to RNA-binding proteins (46, 47). NIR spectra of miSplits should further increase signal-to-background ratio and provide an additional color for simultaneous imaging of several types of molecules or processes in a cell. To test miSplits for RNA labeling, we chose a system that uses two high affinity RNA-protein interactions, MS2 bacteriophage coat protein (MCP) and its MS2 RNA-binding site (MBS) and PP7 bacteriophage coat protein (PCP) and its PP7 RNA-binding site (PBS) (46). We fused the MCP and PCP proteins with two fragments of miSplit709 and tagged mRNA encoding an ECFP protein with 12 pairs of MBS-PBS sites (FIG. 3e). As a control, we used ECFP mRNA tagged with 24 copies of MBS only. miSplit709 allowed to specifically visualize the mRNA-12×MBS-PBS molecules n live HeLa cells. The fluorescence signal was >5-fold higher than for mRNA-24×MBS control (FIG. 3f,g). Similar to miSplit709, miSplit670 also enabled the mRNA detection.

Figures 4A, 4B, 4C, 4D, 4E, 4F, 4G:
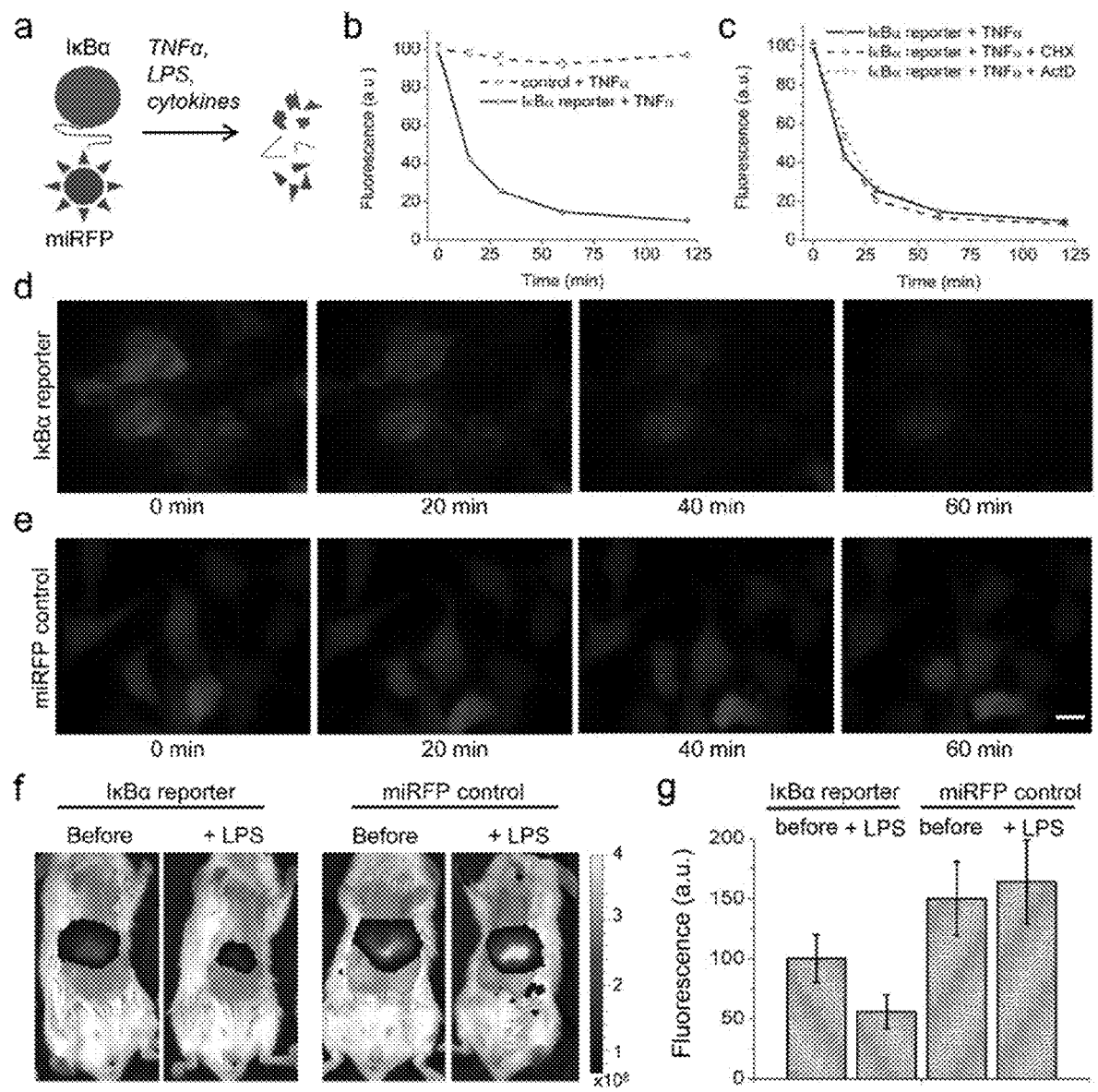
FIG. 4A-4G. NIR IκBα reporter for canonical NF-κB pathway. (a) Schematics showing stimulus-induced degradation of the NIR IκBα reporter. Stimuli inducing IKK activation, such as TNFα, lipopolysaccharide (LPS) and cytokines, lead to IκBα phosphorylation by IKK and degradation of the fusion. (b) The response of the NIR IκBα reporter to treatment with TNFα. Live HEK293 cells stably expressing the reporter or untagged miRFP703 control were treated with TNFα. The fluorescence intensity of cells were analyzed by flow cytometry at different time points. Error bars, s.d. (n=3). (c) Effect of pretreatment with translation inhibitor cycloheximide (CHX) or transcription inhibitor actinomycin D (ActD) on the TNFα-induced reporter degradation kinetics studied as in (b). Error bars, s.d. (n=3). (d, e) Microscopy time-lapse images of live HEK293 cells stably expressing either the NIR IκBα-miRFP703 reporter (d) or untagged miRFP703 control (e) upon treatment with TNFα. Scale bar, 10 μm. (f) Representative images of a mouse expressing the NIR IκBα reporter in liver and a control mouse expressing untagged miRFP703 before and 2 h after injection with LPS. The color bar indicates the total fluorescence radiant efficiency (photons s$^{-1}$ cm$^{-2}$ steradian$^{-1}$ per μW cm$^{-2}$). (g) Quantification of the fluorescence changes for the data in (f). Total radiant efficiencies of the areas corresponding to livers were quantified. Error bars, s.d. (n=3).

NIR IκBα reporter for imaging of IKK activation. We next applied miRFPs to design biosensors based on changes in protein levels in response to activation of specific cellular pathways. By fusing miRFP703 to IκBα, we created a NIR reporter for canonical activation of NF-κB. IκBα is a predominant IκB family member of proteins that inhibit the NF-κB transcription factor, which is a key regulator of immune response, cellular activation, proliferation, and apoptosis (48). Canonical activation of NF-κB depends on induced phosphorylation-dependent IκBa degradation. In resting cells, IκBα sequesters NF-κB dimers in a cytoplasm by masking their nuclear localization signals (NLS). Various stimuli, such as cytokines, TNFα and lipopolysaccharide (LPS), activate IKK kinase, which phosphorylates IκBα marking it as a substrate for polyubiquitination and subsequent degradation by proteasome (FIG. 4a). As a result, NF-κB is released to the nucleus.

To test NIR IκBα reporter in cells, we obtained HEK293 cells stably expressing IκBα-miRFP703. Treatment of these cells with TNFα resulted in a rapid decrease in fluorescence, as expected (49). In contrast, no changes were observed in control cells expressing unfused miRFP703 (FIG. 4b). An inhibition of the translation and transcription did not affect IκBα-miRFP703 reporter degradation (FIG. 4c). Microscopy of cells stably expressing IκBα-miRFP703 reporter and miRFP703 control (FIG. 4d,e) confirmed the results obtained with flow cytometry and allowed to visualize the cytoplasmic localization of IκBα. If miRFP670 or miRFP709 are fused to IκBα, it is possible to image a second, spectrally resolvable NIR FP (miRFP709 or miRFP670, respectively) simultaneously with the IκBα reporter. We demonstrated this in cells co-expressing IκBα-miRFP670 and nuclear H2B-miRFP709.

To study IκBα-miRFP reporter in vivo, we used an established model of the acute liver inflammation (49). The gene coding for IκBα-miRFP703 was delivered to a mouse liver by a hydrodynamic gene transfer (50). We observed that a treatment with lipopolysaccharide (LPS) induced the 3-fold decrease of the fluorescence signal from liver (FIG. 4f). In control experiment with unfused miRFP703, there was no decrease in the fluorescence signal (FIG. 4f).

Figures 5A, 5B, 5C, 5D, 5E:
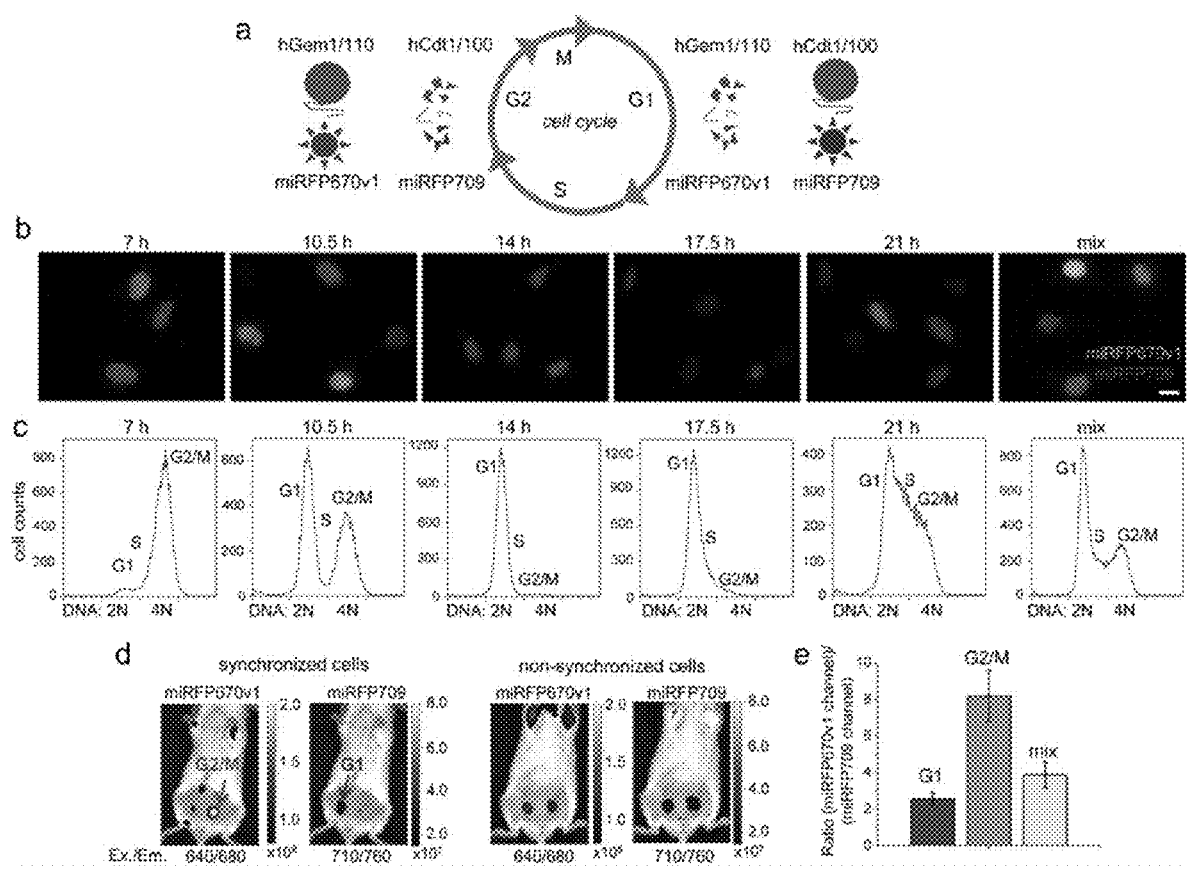
FIG. 5A-5E. NIR cell cycle reporter based on two spectrally distinct miRFPs. (a) Schematics of cell cycle dependent fluorescence changes in NIR cell cycle reporter, which consists of a combination of miRFP670v1-hGem1/100 and miRFP709-hCdt1/110 fusions. These fusions are degraded reciprocally during the cell cycle. The miRFP670v1-hGem1/100 fusion accumulates in S/G2/M phases, whereas the miRFP709-hCdt1/110 fusion accumulates in G1 phase. (b) Microscopy images of NIR cell cycle reporter in cells at different time points during cell cycle progression. HeLa cells stably expressing NIR cell cycle reporter were released after the synchronization by double thymidine block and analyzed at indicated time points. The overlays of two pseudocolor images (miRFP670v1 channel in green and miRFP709 channel in red) are shown. Unsynchronized cells are shown in the most right panel (mix). Scale bar, 10 m. (c) Flow cytometry histograms of Hoechst33342 fluorescence distribution representing the cell cycle progression for the cells shown in (b). Cells in (b) and (c) were prepared and analyzed in parallel. (d) Representative images of mice with implanted cells expressing the NIR cell cycle reporter. A mouse on the left was injected with cells synchronized as in (b, c). The cells in G2/M and G1 phases were injected in the left and right sides of the mouse, respectively. A mouse on the right was injected with the non-synchronized cells into both sides. The two channels for miRFP670v1 and miRFP709 imaging are shown. The color bars indicate the total fluorescence radiant efficiency (photons s$^{-1}$ cm$^{-2}$ steradian$^{-1}$ per μW cm$^{-2}$). (e) The ratios between the fluorescence intensities of the implanted cells in the miRFP670v1 and miRFP709 channels for the data in (d). Total radiant efficiencies of the areas corresponding to the implanted cells were quantified for each channel and the ratios were calculated. Error bars, s.d. (n=6).

NIR cell cycle reporters. We further engineered a cell cycle reporter based on spectrally distinct miRFPs. Available Fucci (fluorescence ubiquitination-based cell cycle indicator) cell cycle reporters are based on green and red GFP-like FPs fused to cell cycle regulated proteins, Geminin and Cdt1, which are involved in licensing of replication origins (31, 32). Fucci reporter offers an accurate and versatile visualization of the cell cycle progression and facilitates studies of developmental processes, such as pattern formation, morphogenesis, cell differentiation, growth, cell migration and cell death (51). To design a NIR cell cycle reporter, which will allow non-invasive monitoring of cell cycle in both cells and whole organisms, we used the same approach but applied miRFP670v1 and miRFP709 (FIG. 5a). Two specific E3 ligase activities mark Geminin and Cdt1 with ubiquitin for proteosomal degradation in a cell-cycle dependent manner. As a result, protein levels of Geminin and Cdt1 oscillate in antiphase. The Cdt1 level is the highest during G1 phase, and then it degrades in S/G2/M phases, whereas the Geminin level is the highest during S/G2/M phases, and it degrades in G1 phase. Thus, the levels of the fused FPs also undergo reciprocal changes, resulting in the dynamic color change during cell cycle progression.

To find an optimal reporter, we created miRFP670v1 and miRFP709 fusions with different deletion mutants of Cdt1 and Geminin: hCdt(30-120) (31), hCdt(1/100) (52), hGem (1/110) (31), and hGem(1/60) (32). The truncated Cdt1 and Geminin variants are used to not perturb the normal cell cycle (31). We tested their combinations for specificity to cell cycle phases and possible interference with the cell cycle. We selected a combination of miRFP670v1-hGem(1/110) and miRFP709-hCdt(1/100). HeLa cells stably expressing these two fusions, which we call NIR cell cycle reporter, divided normally for many generations.

To test performance of NIR cell cycle reporter, we synchronized division of HeLa cells stably expressing this reporter using the double thymidine block procedure (53). We analyzed the cells by flow cytometry and fluorescence microscopy at different time points after release from the block. To analyze the cell cycle phase, cells were labeled with Hoechst33342, whose fluorescence signal is proportional to the DNA content and enables to reveal the various phases of the cell cycle. For microscopy imaging of the reporter, we used two filter sets allowed to distinguish miRFP670 and miRFP709 as above. The two miRFPs are also distinguishable by flow cytometry. Thus, NIR cell cycle reporter can be studied by both microscopy and flow cytometry. As expected, the changes in Hoechst33342 fluorescence corresponded to the reciprocal changes in the levels of the miRFP670v1 and miRFP709 fusions during the cell cycle (FIG. 5b,c). Indeed, in the G2/M phase (7 h after a release from the cell cycle arrest) the cells predominantly expressed miRFP670v1 as can be seen by microscopy (FIG. 5b,c) and flow cytometry. In contrast, in G1 phase (14 h after a release from the cell cycle block), the cells expressed miRFP709 (FIG. 5b,c). As expected, the non-synchronized cells expressed either miRFP670v1, or miRFP709, or both. We also tested and found that NIR cell cycle reporter works in HEK293 cells, similar to HeLa cells.

To test if NIR cell cycle reporter can be used to discriminate between cells in G1 phase and in G2/M phase in vivo, we synchronized cells as above. Then we injected the cells in G1 phase in the left mammary gland and the cells in the G2/M phase in the right mammary gland of mice (FIG. 5d). Imaging of mice in two different channels allowed distinguishing between cells in G1 and G2/M phases. A ratio between the fluorescence signals in these channels reflected the proliferation status of cells (FIG. 5e). For injected non-synchronized cells, this ratio lied between the two ratios obtained for cells synchronized in G1 and G2/M phases (FIG. 5d,e). We also found that this ratio remained approximately the same when the injected cells grown into tumors.

Far-red FRET-based ratiometric sensor. By combining monomeric miRFPs with monomeric far-red GFP-like FPs as FRET (Forster resonance energy transfer) donors, effective FRET pairs can be created (FIG. 6a). Among currently available monomeric far-red FPs, mKate2 exhibits the highest quantum yield of 0.40 (10), which makes it one of the best FRET donors. An advantage of miRFPs as FRET acceptors are their high extinction coefficients. The mKate2-miRFP FRET pairs are also characterized by substantial overlap of the donor emission and the acceptor excitation spectra (FIG. 6b).

Using miRFP703 as a FRET acceptor, we designed a ratiometric far-red caspase-3 sensor. We tested its performance in live HeLa cells. The emission spectra were measured in the cell suspension before and after treatment with 1 µM staurosporine (FIG. 6c). The FRET efficiency measured as an increase in mKate2 donor fluorescence after cleavage of the caspase-3 sensor reached 45%. For comparison, the experimentally observed FRET efficiencies of the ECFP-EYFP pair in similar apoptosis sensor was 48% (54).

Then we monitored FRET changes caused by apoptosis in cells by microscopy. For this, we utilized a ratiometric approach used in cases with well-defined donor-to-acceptor stoichiometry (55) in which the signal in FRET channel is normalized by the signal in the donor channel on a pixel-by-pixel basis (FIG. 6d). The staurosporine treatment caused a gradual decrease of the FRET/donor signal ratio with time, reaching 41% after few hours in imaged cells (FIG. 6e). In future studies, the far-red detection (above 600 nm) of mKate2-miRFP FRET-based sensors should allow combining them with several spectrally distinct FRET-pairs in a single cell.

Spectral properties of miRFPs allow a design of a fully NIR FRET pair. miRFP670 has the highest quantum yield (14%) among BphP-based FPs and the most blue-shifted spectra, making it a good FRET donor for red-shifted NIR FPs. We combined it with iRFP720, which is the most red-shifted NIR FP, and tested performance of miRFP670-iRFP720 FRET pair in HeLa cells. The FRET efficiency measured as an increase in the donor fluorescence after cleavage reached 30% (FIG. 7a-c).

We also tested a FRET pair of miRFP670 with a new monomeric non-fluorescent chromoprotein, called miCP756, having an absorbance maximum at 756 nm and extinction coefficient of 78,300 M-1 cm-1 (unpublished). Similarly to miRFPs, miCP756 is designed from a natural BphP, and efficiently binds endogenous BV in cells. Owning to the rather wide absorption spectrum, miCP756 can serve as a FRET acceptor for either miRFP670 or miRFP703 (quantum yield 9%) donors. Although miRFP670-miCP756 is a functional FRET pair, it also acts as a monochromatic fully NIR sensor: only miRFP donor emits fluorescence. The FRET efficiency measured as an increase in miRFP670 donor fluorescence after the cleavage was 25% (FIG. 7d-f).

We further explored the possibilities of the function miRFP fusions and tested their fusions with *Renilla* luciferase (RLuc8) (FIG. 7g). Using commercially available Prolum Purple I (PPI) substrate, which bioluminesces around 400 nm, it is possible to induce BRET from RLuc8 to miRFPs. Indeed, the emission of RLuc supplemented with Prolum Purple I overlaps with the Soret band of BphP-based NIR FP containing BV as chromophore (FIG. 7h). We expressed this fusions in mammalian HeLa cells and measured the NIR bioluminescence spetra of the resulting constructs (FIG. 7i). Due to BRET from RLuc8 to miRFPs, the resulting NIR bioluminescence of the chimeras has maxima at 670 nm or 709 nm, respectively. This constructs can be used as a protein fusion for multimodality in vivo imaging and as a template for development of sensors of various designs, including Ca2+-sensor and monitoring of PPIs.

Monomerization of dimeric NIR FPs iRFPs and characterization of the monomerized variants. We hypothesized that monomerization mutations that work in RpBphP1-derived miRFPs can be applied to other BphP-derived FPs to obtain monomeric variants without significant loss in brightness. We selected dimeric iRFPs as starting points for monomerization since these dimeric FPs are currently the brightest in mammalian cells and include FPs with highest spectral variability [Our rev]. To precisely identify target residues to mutate in iRFPs, we created an alignment of miRFPs derived from RpBphP1 with iRFPs and their parental BphPs (FIG. 9). Based on this alignment, we selected the following positions in RpBphP1-derived miRFPs that can be transferred to other BphP-based NIR FPs for their monomerization: 300, 301, 304, 305, 308 as numbered according to RpBphP1, i.e. SEQ ID NO: 10. In RpBphP2-derived iRFP682, iRFP713, and iRFP720 these positions correspond to 301, 302, 305, 306, 309 as numbered according to RpBphP2 (SEQ ID NO: 17). In RpBphP6-derived iRFP670 and iRFP702, these positions corresponded to 295, 296, 298, 299, 302 as numbered according to RpBphP6 (SEQ ID NO: 16). To create monomerized iRFPs, we introduced the same residues as in BphP1-based miRFPs in the selected positions. However, it is no doubt that other charged or small residues introduced in the specific positions will also result in dimerization by disrupting the dimeric interface at the C-terminus of FPs. Specifically, RpBphP1-derived FPs can be monomerized by introducing at least four amino acids selected from the group consisting of D300, E300, K300, R300, D301, E301, K301, R301, D304, E304, K304, R304, D305, E305, K305, R305, T308, S308, G308, and A308. RpBphP2-derived FPs can be monomerized by introducing at least four amino acid residues selected from the group consisting of D301, E301, K301, R301, D302, E302, K302, R302, D305, E305, K305, R305, D306, E306, K306, R306, T309, S309, G309, and A309. RpBphP6-derived FPs can be monomerized by introducing at least four amino acid residues selected from the group consisting of D295, E295, K295, R295, D296, E296, K296, R296, D298, E298, K298, R298, D299, E299, K299, R299, T302, S302, G302, and A302. Further other BphP-based NIR FPs can be also monomerized using the same strategy. The exact positions to introduce mutations can be found by creating an alignment of BphP-based FPs of interest with miRFPs, similar to that shown in FIG. 9.

Characterization of the monomerized iRFPs. The characterization demonstrates that iRFPs monomerized by the approach described in this invention maintain relatively high brightness (no more than 50% loss relative to dimeric variants), excitation and emission spectral characteristics and other beneficial properties of dimeric variants (Table 1), but do not oligomerize.

Figures 11A, 11B:
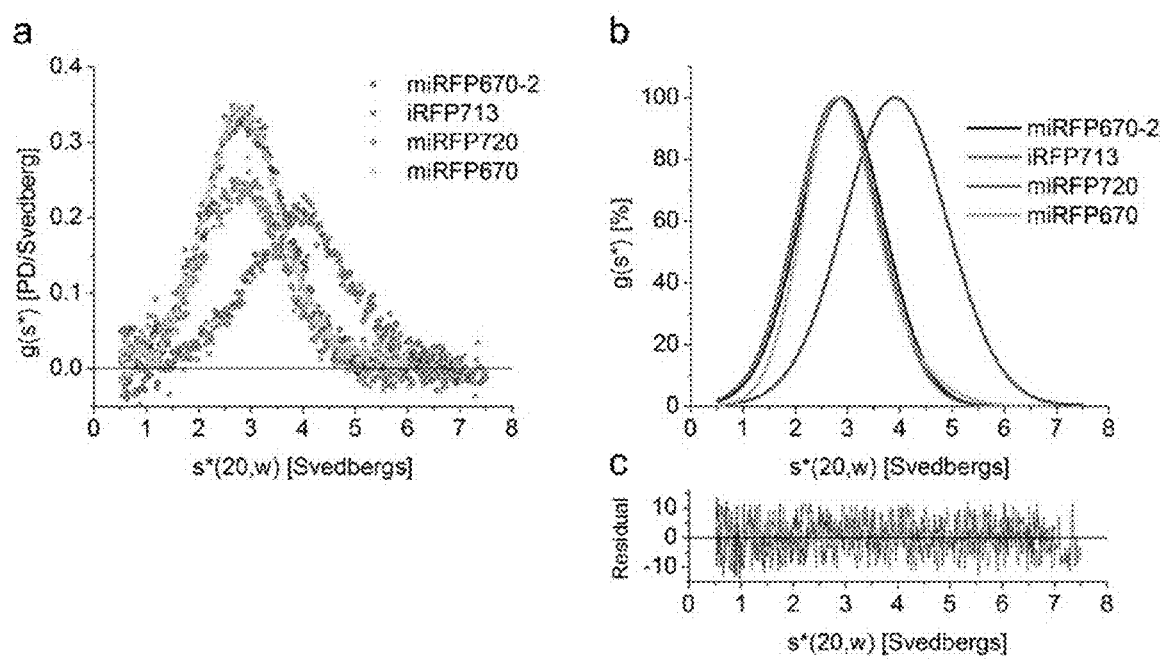
FIG. 11A-11B. Monomeric state of miRFPs confirmed by analytical ultracentrifugation analysis. miRFPs from each family of miRFPs were analyzed by sedimentation velocity analytical ultracentrifugation. miRFP670 represents miRFP proteins derived from RpBphP1; miRFP670-2 represents monomerized iRFP670 and iRFP702 derived from RpBphP6; miRFP720 represents monomerized iRFP682, iRFP713, and iRFP720 derived from RpBphP2. The proteins were analyzed at concentrations of 15 µM in PBS buffer at 20° C., the time-derivative method was used. (a) Overlay of the sedimentation coefficient distributions for iRFP670-2 (blue), iRFP713 (red), miRFP720 (magenta), and miRFP670 (cyan). (b) Overlay of the normalized best-fit sedimentation coefficient distributions. (c) The residuals corresponding to the resolved fits shown in (b). All monomeric NIR FPs showed peaks centered at a sedimentation coefficient of ~2.8-2.85 S that corresponds to the protein monomer (Mw=35±3 kDa). The dimeric iRFP713 control showed the peak at ~4.0 S that corresponds to the dimer.
Figure 12:
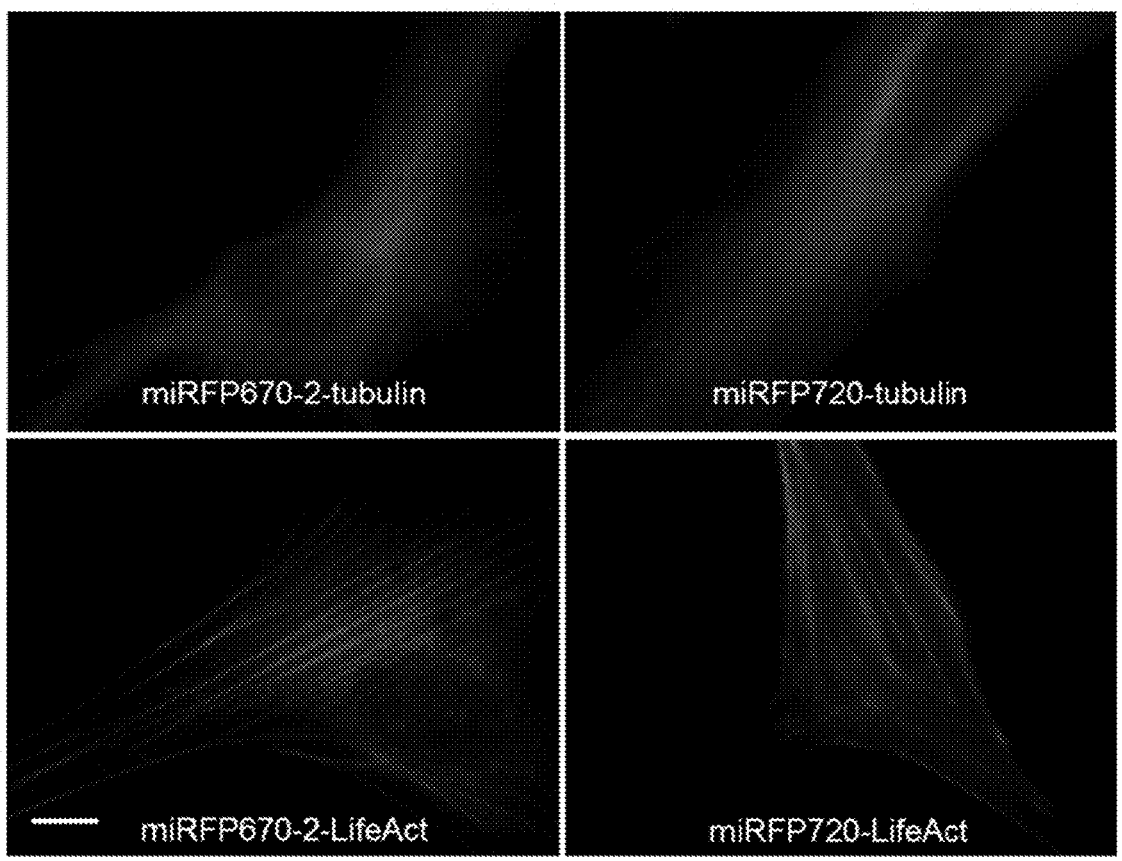
FIG. 12. Monomeric state of monomerized iRFPs confirmed by correct localization of protein fusions. Live HeLa cells transiently transfected with the miRFP670-2 and miRFP720 fusion constructs with α-tubulin (C-terminal) and actin-binding LifeAct (N-terminal) were visualized by widefield microscopy. miRFP670-2 represents monomerized iRFP670 and iRFP702 derived from RpBphP6; miRFP720 represents monomerized iRFP682, iRFP713, and iRFP720 derived from RpBphP2. Scale bar, 10 µM.

First, we tested the oligomeric state of monomerized iRFPs (miRFP670-2, miRFP682, miRFP702, miRFP713, and miRFP720) (FIG. 11). iRFPs include NIR FPs of two groups: developed from RpBphP2 (miRFP682, miRFP713, and miRFP720) and developed from RpBphP6 (miRFP670-2 and miRFP702) (FIG. 9). FPs within each group differ only by internal mutations that influence spectral properties. Thus, for oligomeric state characterization, we selected on FP from each group: miRFP670-2 (RpBphP6-based) and miRFP720 (RpBphP2-based). We also included miRFP670 as a representative of monomeric miRFPs derived from RpBphP1. We confirmed the monomeric state of each family of NIR FPs by analytical ultracentrifugation (FIG. 11a-c) at concentrations as high as 15 µM. Further, we tested monomeric state of monomerized iRFPs in live cells by imaging localization of protein fusions (FIG. 12 and FIG. 2).

Further, we tested effective brightness of monomerized iRFPs in mammalian cells as one the most important parameter for their applications and important feature of the monomerization approach described in this invention (FIG. 13). Importantly, we observed almost no loss of brightness of RpBphP2-derived NIR FPs miRFP682, miRFP713, and miRFP720 comparing to their dimeric variants (FIG. 13a). For RpBphP6-derived NIR FPs miRFP670-2 and miRFP702 the brightness decreased no more than 50% comparing to their dimeric variants.

Further, we characterized spectral properties, molecular brightness (the product of a molar extinction coefficient and quantum yield), photostability, and pKa of monomerized iRFPs (Table 1). We found that monomerized iRFPs retained the properties of dimeric iRFPs. Thus, we confirmed that the monomerization method described here results in monomeric NIR FPs with similar properties of their parental dimeric variants with no significant loss in effective brightness in mammalian cells.

Monomerized iRFPs (miRFP670-2, miRFP682, miRFP702, miRFP713, and miRFP720) can be used in the same applications as miRFPs derived from RpBphP1 described above. The unique advantage of having a monomeric iRFPs is a possibility to create efficient fully NIR FRET pairs consisting solely of monomeric FPs using the red-shifted miRFP713 and miRFP720. miRFP720 is the best choice for a combination with miRFP670 (and also miRFP670-2) as the most NIR-shifted FP with the longest excitation and emission peaks available. Here we tested an advantage of using miRFP720 as an acceptor in the FRET pair with miRFP670, comparing to miRFP709 (FIG. 14). Importantly, miRFP670-miRFP720 FRET pair demonstrated 34% changes in the ratio donor-to-FRET after cleavage, comparing to 18% for miRFP670-miRFP709 FRET pair (FIG. 14).

DISCUSSION

Monomeric state of three miRFPs and their high effective brightness in mammalian cells without supply of external BV or co-expression of BV-producing HO make them advanced NIR protein tags (Table 1). Their protein fusions exhibit proper localization in cellular filaments and intracellular compartments (FIG. 2a), while the most spectrally distant miRFP670 and miRFP709 enable two-color protein labeling. Super-resolution SIM imaging with miRFP fusions allows visualization of the finer details of organelles and filaments than conventional wide-field microscopy (FIG. 2b,c). miRFPs enabled crosstalk-free three-color microscopy together with conventional green and red FPs, as we demonstrated in three-color SIM (FIG. 2d).

Importantly, miRFPs substantially outperform the only other monomeric NIR FP, mIFP, in terms of the effective brightness and the photostability in mammalian cells. Yet another advantage of mRFPs is availability of spectrally resolvable variants, which can be combined for multicolor NIR imaging.

Moreover, bright multicolor miRFPs now enable development of a wide range of NIR reporters and biosensors for various intracellular processes involving interaction of proteins, signaling cascades and cell fate, among others. Here we applied miRFPs to design just few of them, such as reporters for PPI, for RNA, for NF-κB pathway, and for cell cycle progression.

miSplit670 and miSplit709 are the first NIR BiFC reporters that are based on truly monomeric NIR FPs. Both miSplits are comparable in brightness to dimeric iSplit (1) but have much lower non-specific BiFC background and substantially higher BiFC contrast. In contrast to dimeric iSplit, miSplits can be applied for screening of novel PPIs because the monomeric state of miSplit parts will not interfere with PPIs themselves. Furthermore, the combination of spectrally distinct miSplits enables to distinguish PPIs of one protein with two alternative partners (FIG. 3a,c).

The monomeric nature and low complementation background of miSplits allow NIR RNA imaging (FIG. 3e-g). Since miSplits are monomeric, all individual mRNA molecules are detected separately in a cell. The fluorescence level of the miSplit BiFC reports on the amount of transcribed mRNA, while the fluorescence pattern reports on the mRNA intracellular localization. In contrast to other RNA labels, the NIR miSplit labeling is suitable for RNA imaging both in cells and in vivo.

Similar to GFP-based BiFC split reporters, miSplits are irreversible. The BiFC irreversibility enables integration, accumulation and subsequent detection of transient PPIs and low affinity complexes (56, 57). In contrast to reversible luciferase split reporters, BiFC reporters (i) allow subcellular localization of a PPI by microscopy, (ii) can be applied for PPI screening, (iii) can be applied in multicolor detection of several PPIs, and (iv) do not require supply of substrate (58). Similarly to GFP-based BiFC split pairs, miSplits should enable monitoring of activities of drug targets, such as GPCR and RTK receptors (57), identifying of potential off-target effects of drug candidates by detection of downstream PPIs associated with specific signaling pathways (57), and genome-wide PPI studies (59). NIR fluorescence of miSplit reporters enable their use for non-invasive in vivo imaging and as additional colors for detection of several PPIs.

The NIR IκBα reporter allows non-invasive studies of canonical activation of NF-κB pathway in cells and in animal tissues (FIG. 4). Compared to luciferase-based IκBα reporter (49), NIR IκBα reporter is suitable for longitudinal quantitative microscopy in live cells and in vivo imaging without substrate injection. Our data show that a fluorescence biosensor, such as IκBα reporter, does not always require a second reference color, since its signal is stable over time without stimuli (FIG. 4d,e). In contrast, a reference signal is necessary for luciferase-based reporters, since bioluminescence changes over time as the result of time-dependent substrate delivery, substrate consumption and degradation. The NIR IκBα reporter could be applied to study pharmacodynamics of ligands and drugs, which target NF-κB signaling. IKK-dependent activation of NF-kB pathway is a promising target for drug development since it is involved in chronic inflammation conditions, such as inflammatory bowel disease, asthma, rheumatoid arthritis (60, 61) and cancer (62). The NIR IκBα reporter is an example of a biosensor based on the post-translational changes in protein levels. Analogous reporters for other signaling pathways can be created with bright miRFPs by using the same approach.

The NIR cell cycle reporter relies on two spectrally resolvable miRFPs, whose fusions accumulate reciprocally during the cell cycle. We demonstrated that this reporter can be applied in cells with analysis by microscopy or by flow cytometry and also in non-invasive whole-body studies by spectral imaging (FIG. 5). The ratio between signals of two miRFPs serves as an indicator of proliferation status of the cell population in vivo. In contrast to green-red GFP-based Fucci indicator, NIR cell cycle reporter is suitable for non-invasive in vivo studies.

miRFP703 makes the effective FRET pair with far-red GFP-like FP mKate2 (FIG. 6). We found that the FRET efficiency between mKate2 and miRFP703 is comparable to that of commonly used ECFP-EYFP pair. The designed mKate2-miRFP703 caspase-3 sensor for apoptosis should be a valuable probe for multicolor imaging. The mKate2-miRFP703 pair can be used to re-design a variety of existing FRET biosensors, including those for calcium, for activity of small GTPases and voltage sensors, for their in vivo applications.

miRFPs make the efficient FRET pairs with NIR FPs and chromoproteins (FIG. 7). We demonstrated this using caspase-3 FRET sensors based on miRFP670-iRFP720 and miRFP670-miCP756 FRET pairs. These FRET pairs are unique as they are fully based on NIR FPs. miRFP670-iRFP720 and miRFP670-miCP756 FRET pairs, similar to mKate2-miRFP703 pair, can be used to re-design a variety of existing FRET biosensors, including those for calcium, for activity of small GTPases and voltage sensors, for their in vivo applications.

In fusions with *Renilla* luciferase (RLuc8), miRFPs become a fusion tags for multimodality in vivo imaging allowing a detection of both NIR luminescence and NIR fluorescence at the same time. These fusions should become a starting points for development of sensors of various designs, including Ca2+-sensor and monitoring of PPIs.

Here we disclosed a method for monomerization of BphP-based FPs that involves introduction of at least four residues at specific positions in the C-terminus of the FP (charged at positions 300, 301, 304, 305, and small or polar amino acid residues at position 308; numbering is according to RpBphP1, i.e. SEQ ID NO: 10 (FIG. 10). The corresponding positions in other FPs are derived from alignment with RpBphP1, as shown in FIG. 9. Using this method, we monomerized bright dimeric spectrally distinct iRFPs. The obtained proteins named miRFP670-2, miRFP682, miRFP702, miRFP713, and miRFP720 behaved as monomers at high concentrations, as tested by analytical ultracentrifugation (FIG. 11a-c). Monomerized iRFPs also correctly localized in filamentous protein fusions in live mammalian cells (FIG. 12). The key feature of the described method for monomerization is that this approach allows to obtain monomeric versions of BphP-based derived FPs without significant (no more than 50%) loss of effective brightness in mammalian cells. We demonstrated this by comparing brightness of monomerized iRFPs with their parental dimeric versions (FIG. 13).

Although monomerized iRFPs (miRFP670-2, miRFP682, miRFP702, miRFP713, and miRFP720) can be utilized in the same applications as described for RpBphP1-derived miRFPs, the most red-shifted of them miRFP713 and miRFP720 are particularly advantageous for applications in FRET biosensors. We demonstrated the advantage of using miRFP720 as a FRET acceptor for miRFP670, comparing to miRFP709. In the same conditions, Monomerized iRFPs (miRFP670-2, miRFP682, miRFP702, miRFP713, and miRFP720) can be used in the same applications as miRFPs derived from RpBphP1 described above. The unique advantage of having a monomeric iRFPs is a possibility to create efficient fully NIR FRET pairs consisting solely of monomeric FPs using the red-shifted miRFP713 and miRFP720. miRFP720 is the best choice for a combination with miRFP670 (and also miRFP670-2) as the most NIR-shifted FP with the longest excitation and emission peaks available. Here we demonstrated an advantage of miRFP670-miRFP720 FRET pair comparing to miRFP670-miRFP709 FRET pair. Whereas the first one showed 34% changes in the ratio donor-to-FRET after cleavage, the later had only 18% changes (FIG. 14). Thus, miRFP720 as well as miRFP713 is a perfect FRET acceptor for blue-shifted monomeric donors miRFP670 and miRFP670-2. The NIR FRET pair miRFP670-miRFP720 is currently the best NIR FRET pair that consists of monomeric NIR FPs. It can be used to re-design a variety of existing FRET biosensors, including those for calcium, for activity of small GTPases and voltage sensors, for their in vivo applications.

In conclusion, the developed spectrally distinct miRFPs and miRFP-based biosensors allow non-invasive multicolor visualization of biological processes across scales, from super-resolution microscopy to tissue and whole-body animal imaging. The ability to use the same probe at the cellular and organismal levels will advance studies of cancer, neuroscience, immunology, developmental and stem cell biology, as well as will make preclinical drug screening significantly faster and more efficient.

Materials and Methods

The DNA corresponding to PAS-GAF domains (first 315 amino acids) of RpBphP1 from *Rhodopseudomonas palustris* was PCR-amplified and cloned as the BglII/EcoRI fragment into a pBAD/His-B vector (Life Technologies/Invitrogen). The DNA corresponding to iRFPs were cloned into pBAD/His-B vector for expression in bacteria or pEGFP-N1 plasmid (Clontech) for expression in mammalian cells as described in (16). Site-specific mutagenesis was performed using a QuikChange mutagensis kit (Stratagene). Random mutagenesis was performed with a GeneMorph II random mutagenesis kit (Stratagene) using conditions that resulted in the mutation frequency of up to 16 mutations per 103 base pairs. A mixture of mutated genes was electroporated into LMG194 host cells (Invitrogen) containing the pWA23h plasmid encoding HO from *Bradyrhizobium* ORS278 (hmuO) under the rhamnose promoter (16, 63). Typical libraries consisted of more than 106 independent clones. The LMG194 cells were grown overnight at 37° C. in RM minimal medium supplemented with ampicillin and kanamycin.

Protein expression was induced with 0.002% arabinose and 0.02% rhamnose. The cells were grown for 6-8 h at 37° C. and then at 18° C. for 24 h. For flow cytometry screening, bacterial cells were washed with phosphate-buffered saline (PBS) and diluted with PBS to an optical density of 0.03 at 600 nm. The libraries were screened using MoFlo XDP (Beckman Coulter) fluorescence-activated cell sorter equipped with 647 nm laser lines for excitation and a 700 nm LP emission filter for positive selection. The brightest collected infrared bacterial cells were rescued in SOC medium at 37° C. for 1 h and then grown on LB/ampicillin/kanamycin Petri dishes supplemented with 0.02% arabinose and 0.2% rhamnose overnight at 37° C. and then incubated at 18° C. Screening for spectrally distinct mutants on Petri dishes was performed with IVIS Spectrum imager (PerkinElmer/Caliper). Data analysis was performed using the LivingImage v.4.3.1 software (PerkinElmer/Caliper).

The mutants selected in bacteria were tested for the oligomeric state by size exclusion chromatography as described below. We also tested their brightness in HeLa cells transfected with plasmids obtained after the FP genes were swapped with a gene encoding EGFP in the pEGFP-N1 plasmid (Clontech). A mixture of several selected mutants was then used as a template for the next round of mutagenesis.

For expression of proteins in bacteria producing BV, the genes coding for the proteins in a pBAD/His-B vector were expressed either in LMG194 or TOP10 bacterial cells (Life Technologies/Invitrogen) bearing the pWA23h. Bacterial cells were grown in RM medium supplemented with ampicillin and kanamycin. First, HO was expressed with addition of 0.02% rhamnose for 5 h at 37° C. Then 0.002% arabinose was added and bacterial culture was incubated for additional 12 h at 37° C. following by 24 h at 18° C. Proteins were purified using Ni-NTA agarose (Qiagen). In the elution buffer, imidazole was substituted for 100 mM EDTA. The elution buffer was replaced with PBS buffer using PD-10 desalting columns (GE Healthcare).

Fluorescence spectra were recorded using a FluoroMax-3 spectrofluorometer (Jobin Yvon). A Hitachi U-2000 spectrophotometer was used for absorbance measurements. The extinction coefficient was calculated from a comparison of absorbance values at the main peak at Q band with the absorbance value at Soret band, assuming that single pyrrole ring absorbs with extinction coefficient of 39,900 M−1 cm−1 (3, 4). To determine quantum yield, we compared the fluorescence signal of a purified protein to that of an equally absorbing Nile blue dye (quantum yield is 0.27 in an acidic ethanol (64)). pH titrations were done using a series of buffers (100 mM sodium acetate, 300 mM NaCl for pH 2.5-5.0 and 100 mM NaH2PO4, 300 mM NaCl for pH 4.5-9.0).

To perform size exclusion liquid chromatography a 2 ml volume of purified miRFPs was applied on the HiLoad 16/600 Superdex 200 column (GE Healthcare) equilibrated with 10 mM Hepes buffer pH 7.4 containing 50 μM EDTA, 10% glycerol, 150 mM NaCl, 1 mM DTT, 0.2 mM PMSF, 0.01% EP-40 and 0.2 mM benzodiazepin. A 1 ml/min flow rate was used. The column was calibrated using the gel filtration standards (Bio-Rad Laboratories).

Analytical ultracentrifugation was conducted at 20° C. and 58,000 r.p.m. with an Optima XL-I centrifuge (Beckman Coulter) using the AN-60Ti rotor and the absorption optics set to 645 nm. Sednterp v.20120828beta software was used to calculate the partial specific volume of the proteins from their sequence and the density and viscosity of the buffers. The sedimentation parameters were corrected to standard conditions (20,w) using these values. For sedimentation velocity (SV) experiments, 350 ml of protein sample and an equal volume of PBS buffer were loaded into two-sector cell assemblies with the protein concentration corresponding to A645 E0.9. Fifty scans were collected over the course of a centrifuge run. A subset of scans, beginning with those where a clear plateau was evident between the meniscus and the boundary, was selected for time-derivative analysis using DCDTþ v.2.4.2 software {Philo, 2006 #19781}.

To construct mammalian expression plasmids, the respective genes of FPs were PCR-amplified as AgeI-NotI fragments and swapped with a gene encoding EGFP in a pEGFP-N1 plasmid (Clontech). IFP2.0-N1 and mIFP-N1 plasmids were acquired from Addgene (#54785 and #54620, respectively).

For protein tagging and labeling of intracellular structures study, miRFPs were amplified, digested with restriction enzymes and then swapped with mTagBFP2 either as C- (for α-tubulin and clathrin) or N-terminal fusions (for keratin, α-actinin, LifeAct, EB3, myosin, vimentin, clathrin, LAMP1, zyxin, H2B and mitochondrial signal) as previously described (65). C-terminal fusions (SGGGG)n linker was increased to 30 amino acids. N-terminal fusions linker length was left unchanged.

To create an IκBα reporter plasmid (CMV-IκBα-miRFP703), we used a CMV-IκBα-FLuc plasmid kindly provided by S. Achilefu and D. Piwnica-Worms. A FLuc gene was replaced with one of the miRFP genes. Kozak sequence was deleted in the CMV-IκBα-miRFP703 and CMV-miRFP control plasmids.

miSplit670 and miSplit709 reporter plasmids, which are pC4-RHE-PAS, pC4EN-F1-GAF670 and pC4EN-F1-GAF709, were constructed from an iSplit plasmids (21) by swapping either PAS or GAF domains. A linker -ggggsggggs- (SEQ ID NO: 18) was left unchanged. Where appropriate, an NLS sequence in the pC4EN-F1 plasmid was deleted by site-directed mutagenesis.

For mRNA labeling, a CMV-PAS-MCP plasmid was constructed as follows. PAS-ggggsggggs-without STOP codon was amplified as a single fragment and inserted into the —C1 vector backbone using AgeI and KpnI sites, MCP was amplified from an ubc-nls-ha-MCP-VenusN-nls-ha-PCP-VenusC plasmid (Addgene, #52985) and inserted at KpnI and BamHI sites. The cmv-PCP-GAF670 and cmv-PCP-GAF709 plasmids were constructed as follows. A PCP without STOP codon was amplified from an ubc-nls-ha-MCP-VenusN-nls-ha-PCP-VenusC plasmid and then inserted into the —C1 vector backbone using AgeI and EcoRI restriction sites. A -ggggsggggs-miGAF was amplified as a single fragment and inserted using EcoRI and KpnI sites. A phage-cmv-cfp-12×MBS-PBS was obtained by swapping a 12×MBS-PBS fragment from a Pcr4-12×MBS-PBS (Addgene, #52984) with 24×MS2 in a phage-cmv-cfp-24×ms2 plasmid (Addgene, #40651). An ubc-nls-ha-MCP-VenusN-nls-ha-PCP-VenusC, a phage-cmv-cfp-24×MS2, and a Pcr4-12×MBS-PBS plasmids were gifts from B. Wu and R. Singer.

Plasmids encoding several green-red Fucci cell cycle reporters were provided by A. Miyawaki. The mKO2 and mAG genes fused with hCdt(30-120), hCdt(1/100), hGem(1/110) and hGem(1/60) sequences in the pCSII-EF-MCS plasmids were swapped with the miRFP709 or miRFP670v1 genes.

Mammalian HeLa cells were grown in a DMEM medium supplemented with 10% FBS, 0.5% penicillin-streptomycin and 2 mM glutamine (Life Technologies/Invitrogen). HEK293, U87, U20S and Cos-1 cells were grown in the same medium as the HeLa cells. For microscopy, cells were cultured in 35 mm glass-bottom Petri dishes with no. 1 coverglass (MatTek). Plasmid transfections were performed using an Effectene reagent (Qiagen). Stably expressing cells were selected with 700 mg/ml G418 antibiotic. Sorting of positive cells was performed using a FACSAria sorter (Beckman Coulter) equipped with a 635 nm laser and a 680 nm LP emission filter.

NIR cell cycle reporter was delivered by cotransduction with lentiviruses. Replication-defective self-inactivating lentivirus vectors were used. Fusions miRFP709 with hCdt(1/100) or hCdt(30-120) and miRFP670v1 with hGem(1/110) or hGem(1/60) were cloned into pCSII-EF-MCS vector (66). Lentiviral particles were packaged as described in (67) using a plasmid set pCMV-GagPol, pCMV-REV, and pVSV-g kindly provided by P. Chumakov and pCSII-EF-MCS plasmids containing fusions co-transfected in HEK293T cells. For infection of target cells, viral preparations were diluted in complete growth media supplemented with 4 μg/ml Polybrene. Primary cultures of hippocampal neurons were isolated as described (68). Cells were transfected with a Lipofectamine 2000 (Life Technologies/Invitrogen) and imaged 72 h after the transfection Epifluorescence microscopy of live HeLa cells was performed 48 h after the transfection. HeLa cells were imaged using an Olympus IX81 inverted epifluorescence microscope equipped with a 200 W Me-Ha arc lamp (Lumen220 Pro; Prior), 100×1.4 NA oil immersion objective lens (UPlanSApo; Olympus). The two filter sets (605/40 nm exciter and 667/30 nm emitter, and 682/12 nm exciter and 721/42 nm emitter) (Chroma) were used to separately image miRFP670 and miRFP709 in one cell. A cy5.5. filter set (665/45 nm exciter and 725/50 nm emitter) was used for imaging of one NIR FP. A SlideBook v.4.1 software (Intelligent Imaging Innovations) was used to operate the microscope. Photobleaching experiments were performed in HeLa cells transiently expressing FPs with the Olympus IX81 microscope described above. Raw data were normalized to absorbance spectra and extinction coefficients of the proteins, the spectrum of 200 W Me-Ha arc lamp and the transmission of 665/45 nm photobleaching filter.

For super-resolution SIM imaging, cells were fixed with 2% (w/v) paraformaldehyde for 15 min and mounted in Prolong Gold. Multichannel structured illumination microscopy (SIM) images were acquired using a Nikon Structured Illumination system on an inverted Nikon ECLIPSE Ti-E equipped with a 100×1.49 NA oil immersion objective lens. Multicolor fluorescence was generated using diode lasers (405 nm, 488 nm and 647 nm). Acquisition was performed with electron-multiplying CCD cameras (Andor iXon3 DU897) of 512×512 pixel frame size. Three reconstruction parameters (illumination modulation contrast, high resolution noise suppression and out of focus blur suppression) were extensively tested to generate consistent images across experiments without abnormal features or artifacts and producing the best Fourier transforms. The images were processed using Nikon Elements software.

Flow cytometry analysis was performed using a BD LSRII flow cytometer equipped with the 355 nm, 488 nm, 561 nm, and 640 nm lasers and a set of emission filters. 20,000-50,000 events for each cell type were analyzed. To quantify cell fluorescence, a mean fluorescence intensity of the double-positive population in the NIR channel was divided by a mean fluorescence intensity of the same population in the green channel, thus normalizing NIR signal to transfection efficiency.

All the observations for miSplit reporters were performed in HeLa cells 46-48 h after transfection. Where needed, 50 nM rapamycin was added 24 h before observation. Fluorescence was quantified using flow cytometry or fluorescence microscopy.

For IκBα reporter studies, preclonal mixtures of HEK293 cells stably expressing IκBα-miRFP or miRFP control were treated with TNFα (20 ng/ml; Sigma-Aldrich) at indicated time points before flow cytometry. Cycloheximide (100 mg/ml; Sigma-Aldrich) or actinomycin D (1 μM; Sigma-Aldrich) were added 1 h prior to the TNFα treatment.

For NIR cell cycle reporters studies by flow cytometry, microscopy, and in vivo experiments, cells were synchronized by double thymidine block-release procedure as described in (53, 69). To quantify DNA content, DNA was labeled with 5 µg/ml of Hoechst33342 (BD Biosciences) for 30 min prior to flow cytometry.

For characterization of reporters in mice they were fed with AIN-93M Maintenance Purified Diet (TestDiet) to reduce the intrinsic autofluorescence level. For imaging belly fur was removed using a depilatory cream. All animal experiments were performed in an AAALAC approved facility using protocols approved by the Albert Einstein College of Medicine Animal Usage Committee.

For IκBα reporter characterization, in vivo transfection of mouse hepatocytes was performed using the hydrodynamic method as described previously (50). Briefly, IκBα-miRFP703 (20 Gg) or miRFP703 control plasmids (20 Gg) were diluted in PBS in a volume of 1 ml/10 g body weight and injected rapidly (5-7 s) into tail veins of mice using a 3 ml syringe fitted with a 27G needle. The 5-7 week-old female FVB mice (National Cancer Institute, NIH) were used. Twenty-four hours later, mice were anesthetized (isoflurane) and imaged for liver miRFP expression using the IVIS Spectrum system using 675/30 nm excitation and 720/20 nm emission filter set. Immediately following this pretreatment imaging, LPS (4 µg/g body weight, i.v.) was administered. Post-treatment imaging was performed (as above) 2 h later. To quantify fluorescence signals, regions of interest (ROI) were defined manually over the liver. The fluorescence signals of the same ROIs in untreated mice were considered as a background and subtracted.

For NIR cell cycle reporter characterization, 107 cells expressing the reporter were subcutaneously implanted into the mammary gland of SCID/NCr mice (female, 5-7 weeks old) (Taconic) and imaged 2 h later using the IVIS Spectrum. Background-subtracted images of total radiant efficiencies of the regions corresponding to cells or tumors were used for quantification. Filter channels used for calculation of the ratio between miRFP670v1 and miRFP709 signals were 640/30 nm excitation and 680/20 nm emission; and 710 nm excitation and 760 nm emission. The tumors were excised postmortem and imaged using the IVIS Spectrum. All quantitative analysis of fluorescence signals was performed using the Living Image software (PerkinElmer/Caliper).

Characterization of FRET pairs in caspase-3 biosensor. The fusions contained a 11 amino acid linkers with the caspase-3 recognition site (-GGDEVDGPVAT-) (SEQ ID NO: 19). A gene of the first NIR FP was PCR amplified from a pN1 vectors containing the respective FP. A 5'-primer contained BglII site at the end followed by the Kozak sequence and N-terminal coding sequence of the respective FP. A 3'-primer contained sequence encoding the C-terminus of the FP followed by sequence encoding GGDEVDGPVAT amino acids with a DEVD cleavage site, followed by an AgeI site. PCR product was digested with BglII and AgeI and inserted into the digested with same restriction enzymes pN1 vector containing the second FP. Then the constructs were tested in HeLa cells. HeLa cells were transfected with the plasmid encoding a caspase biosensor. Cells were grown in DMEM supplemented with glutamax (Gibco) containing 10% FBS and 0.5% penicillin-streptomycin (Invitrogen). Cells were transfected either using Effectene (Qiagen), or using Mirus transfection reagent LT1 (Mirus Bio) according to manufacturer's protocols. 48 h after transfections cells were either treated with 2 µM staurosporine for 6 h or untreated. Then the cells were removed from the surface by pipetting, washed with PBS and resuspended in the PBS buffer. The spectra corresponding to NIR caspase sensors before (untreated samples) and after cleavage (cells treated with staurosporin) were measured using FluoroMax-3 spectrofluorometer (Jobin Yvon).

REFERENCES

1. Shcherbakova D M, Baloban M, Verkhusha V V. 2015. *Curr Opin Chem Biol* 27: 52-63
2. Weissleder R. 2001. *Nat Biotechnol* 19: 316-7
3. Shu X, Royant A, Lin M Z, Aguilera T A, Lev-Ram V, et al. 2009. *Science* 324: 804-7
4. Filonov G S, Piatkevich K D, Ting L M, Zhang J, Kim K, Verkhusha V V. 2011. *Nat Biotechnol* 29: 757-61
5. Shcherbakova D M, Shemetov A A, Kaberniuk A A, Verkhusha V V. 2015. *Annu Rev Biochem* 84: 519-50
6. Rockwell N C, Lagarias J C. 2010. *Chemphyschem* 11: 1172-80
7. Kapitulnik J, Maines M D. 2012. *Front Pharmacol* 3: 136
8. Tran M T, Tanaka J, Hamada M, Sugiyama Y, Sakaguchi S, et al. 2014. *Exp Anim* 63: 311-9
9. Auldridge M E, Satyshur K A, Anstrom D M, Forest K T. 2012. *J Biol Chem* 287: 7000-9
10. Shcherbo D, Murphy C S, Ermakova G V, Solovieva E A, Chepurnykh T V, et al. 2009. *Biochem J* 418: 567-74
11. Morozova K S, Piatkevich K D, Gould T J, Zhang J, Bewersdorf J, Verkhusha V V. 2010. *Biophys J* 99: L13-5
12. Chu J, Haynes R D, Corbel S Y, Li P, Gonzalez-Gonzalez E, et al. 2014. *Nat Methods* 11: 572-8
13. Wagner J R, Zhang J, von Stetten D, Gunther M, Murgida D H, et al. 2008. *J Biol Chem* 283: 12212-26
14. Lehtivuori H, Rissanen I, Takala H, Bamford J, Tkachenko N V, Ihalainen J A. 2013. *J Phys Chem B* 117: 11049-57
15. Shaner N C, Steinbach P A, Tsien R Y. 2005. *Nat Methods* 2: 905-9
16. Shcherbakova D M, Verkhusha V V. 2013. *Nat Methods* 10: 751-4
17. Yu D, Baird M A, Allen J R, Howe E S, Klassen M P, et al. 2015. *Nat Methods* 12: 763-5
18. Yu D, Gustafson W C, Han C, Lafaye C, Noirclerc-Savoye M, et al. 2014. *Nat Commun* 5: 3626
19. Bhattacharya S, Auldridge M E, Lehtivuori H, Ihalainen J A, Forest K T. 2014. *J Biol Chem* 289: 32144-52
20. Altschul S F, Gish W, Miller W, Myers E W, Lipman D J. 1990. *J Mol Biol* 215: 403-10
21. Filonov G S, Verkhusha V V. 2013. *Chem Biol* 20: 1078-86
22. Tchekanda E, Sivanesan D, Michnick S W. 2014. *Nat Methods* 11: 641-4
23. Pandey N, Nobles C L, Zechiedrich L, Maresso A W, Silberg J J. 2015. *ACS Synth Biol* 4: 615-24
24. Chen M, Li W, Zhang Z, Liu S, Zhang X, et al. 2015. *Biomaterials* 48: 97-107
25. Shcherbakova D M, Baloban M, Pletnev S, Malashkevich V N, Xiao H, et al. 2015. *Chem Biol* 22: 1540-51
26. Gustin K E, Burk R D. 1993. *Biotechniques* 14: 22, 4
27. Barany F. 1985. *Gene* 37: 111-23
28. Colicelli J, Lobel L I, Goff S P. 1985. *Mol Gen Genet* 199: 537-9
29. Higgins D G, Sharp P M. 1989. *Comput Appl Biosci* 5: 151-3
30. Keown W A, Campbell C R, Kucherlapati R S. 1990. *Methods Enzymol* 185: 527-37
31. Sakaue-Sawano A, Kurokawa H, Morimura T, Hanyu A, Hama H, et al. 2008. *Cell* 132: 487-98
32. Sakaue-Sawano A, Ohtawa K, Hama H, Kawano M, Ogawa M, Miyawaki A. 2008. *Chem Biol* 15: 1243-8

33. Matz M V, Fradkov A F, Labas Y A, Savitsky A P, Zaraisky A G, et al. 1999. *Nat Biotechnol* 17: 969-73
34. Zlobovskaya O A, Sergeeva T F, Shirmanova M V, Dudenkova V V, Sharonov G V, et al. 2016. *Biotechniques* 60: 62-8
35. Filippin L, Magalhaes P J, Di Benedetto G, Colella M, Pozzan T. 2003. *J Biol Chem* 278: 39224-34
36. Nagai T, Sawano A, Park E S, Miyawaki A. 2001. *Proc Natl Acad Sci USA* 98: 3197-202
37. Nagai T, Yamada S, Tominaga T, Ichikawa M, Miyawaki A. 2004. *Proc Natl Acad Sci USA* 101: 10554-9
38. Ntziachristos V, Razansky D. 2010. *Chem Rev* 110: 2783-94
39. Razansky D, Buehler A, Ntziachristos V. 2011. *Nat Protoc* 6: 1121-9
40. Wang L V, Hu S. 2012. *Science* 335: 1458-62
41. Bellini D, Papiz M Z. 2012. *Structure* 20: 1436-46
42. Shcherbakova D M, Baloban M, Emelyanov A V, Brenowitz M, Guo P, Verkhusha V V. 2016. *Nat Commun* 7: 12405
43. Strack R L, Strongin D E, Bhattacharyya D, Tao W, Berman A, et al. 2008. *Nat Methods* 5: 955-7
44. Tao W, Evans B G, Yao J, Cooper S, Cornetta K, et al. 2007. *Stem Cells* 25: 670-8
45. Strack R L, Hein B, Bhattacharyya D, Hell S W, Keenan R J, Glick B S. 2009. *Biochemistry* 48: 8279-81
46. Wu B, Chen J, Singer R H. 2014. *Sci Rep* 4: 3615
47. Ozawa T, Natori Y, Sato M, Umezawa Y. 2007. *Nat Methods* 4: 413-9
48. Oeckinghaus A, Ghosh S. 2009. *Cold Spring Harb Perspect Biol* 1: a000034
49. Gross S, Piwnica-Worms D. 2005. *Nat Methods* 2: 607-14
50. Liu F, Song Y, Liu D. 1999. *Gene Ther* 6: 1258-66
51. Zielke N, Edgar B A. 2015. *Wiley Interdiscip Rev Dev Biol* 4: 469-87
52. Ogura Y, Sakaue-Sawano A, Nakagawa M, Satoh N, Miyawaki A, Sasakura Y. 2011. *Development* 138: 577-87
53. Harper J V. 2005. *Methods Mol Biol* 296: 157-66
54. Domingo B, Sabariegos R, Picazo F, Llopis J. 2007. *Microsc Res Tech* 70: 1010-21
55. Gordon G W, Berry G, Liang X H, Levine B, Herman B. 1998. *Biophys J* 74: 2702-13
56. Morell M, Espargaro A, Aviles F X, Ventura S. 2007. *Proteomics* 7: 1023-36
57. MacDonald M L, Lamerdin J, Owens S, Keon B H, Bilter G K, et al. 2006. *Nat Chem Biol* 2: 329-37
58. Wehr M C, Rossner M J. 2015. *Drug Discov Today*
59. Miller K E, Kim Y, Huh W K, Park H O. 2015. *J Mol Biol* 427: 2039-55
60. Meffert M K, Chang J M, Wiltgen B J, Fanselow M S, Baltimore D. 2003. *Nat Neurosci* 6: 1072-8
61. Li Q, Verma I M. 2002. *Nat Rev Immunol* 2: 725-34
62. Karin M, Yamamoto Y, Wang Q M. 2004. *Nat Rev Drug Discov* 3: 17-26
63. Piatkevich K D, Subach F V, Verkhusha V V. 2013. *Nat Commun* 4: 2153
64. Sens R, Drexhage K H. 1981. *J. Luminesc* 24: 709-12
65. Subach O M, Cranfill P J, Davidson M W, Verkhusha V V. 2011. *PLoS One* 6: e28674
66. Miyoshi H, Blomer U, Takahashi M, Gage F H, Verma I M. 1998. *J Virol* 72: 8150-7
67. Guryanova O A, Makhanov M, Chenchik A A, Chumakov P M, Frolova E I. 2006. *Mol Biol* 40: 396-405
68. Buxbaum A R, Wu B, Singer R H. 2014. *Science* 343: 419-22
69. Whitfield M L, Zheng L X, Baldwin A, Ohta T, Hurt M M, Marzluff W F. 2000. *Mol Cell Biol* 20: 4188-98

```
SEQUENCES
miRFP670v1 protein sequence
                                                                                  (SEQ ID NO: 1)
mvaghasgspafgtashsnseheeihlagsiqphgallvvsehdhrvigasanaaeflnlgsvlgvplaeidgdllikilphldptaegm pvavrcrignpsteycglmhrppeggliieleragpsidlsgtlapalerirtagslralcddtvllfqqctgydrvmvyrfdeqghglvfse chvpglesyfgnrypsstvpqmarqlyvrqrvrvlvdvtyqpvpleprlspltgrdldmsgcflrsmspchlqflkdmgvratlavslv vggklwglvvchhylprfirfelraickrlaeriatritales miRFP670v1 DNA sequence
                                                                                 (SEQ ID NO: 20)
atggtagcaggtcatgcctctggcagccccgcattcgggaccgcctctcattcgaattccgaacatgaagagatccacctcgccggctcgat ccagccgcatggcgcgcttctggtcgtcagcgaacatgatcatcgcgtcatccaggccagcgccaacgccgcggaatttctgaatctcgga agcgtactcggcgttccgctcgccgagatcgacggcgatctgttgatcaagatcctgccgcatctcgatcccaccgccgaaggcatgccg gtcgcggtgcgctgccggatcggcaatccctctacggagtactgcggtctgatgcatcggcctccggaaggcgggctgatcatcgaactc gaacgtgccggcccgtcgatcgatctgtcaggcacgctggcgccggcgctggagcggatccgcacggcgggttcactgcgcgcgctgt gcgatgacaccgtgctgctgtttcagcagtgcaccggctacgacgggtgatggtgtatcgtttcgatgagcaaggccacggcctggtattc tccgagtgccatgtgcctgggctcgaatcctatttcggcaaccgctatccgtcgtcgactgtcccgcagatggcgcggcagctgtacgtgcg gcagcgcgtccgcgtgctggtcgacgtcacctatcagccggtgccgctggagccgcggctgtcgccgctgaccgggcgcgatctcgaca tgtcgggctgcttcctgcgctcgatgtcgccgtgccatctgcagttcctgaaggacatgggcgtgcgcgccaccctggcggtgtcgctggt ggtcggcggcaagctgtggggcctggttgtctgtcaccattatctgccgcgcttcatccgtttcgagctgcgggcgatctgcaaacggctcg ccgaaaggatcgcgacgcggatcaccgcgcttgagagc
```

-continued miRFP670 protein sequence
(SEQ ID NO: 2)
mvaghasgspafgtashsnceheeihlagsiqphgallvvsehdhrvigasanaaeflnlgsvlgvplaeidgdllikilphldptaegm
pvavrcrignpsteycglmhrppeggliieleragpsidlsgtlapalerirtagslralcddtvllfqqctgydrvmvyrfdeqghglvfse
chvpglesyfgnrypsstvpqmarqlyvrqrvrvlvdvtyqpvpleprlspltgrdldmsgcflrsmspchlqflkdmgvratlavslv
vggklwglvvchhylprfirfelraickrlaeriatritales miRFP670 DNA sequence
(SEQ ID NO: 21)
atggtagcaggtcatgcctctggcagccccgcattcgggaccgcctctcattcgaattgcgaacatgaagagatccacctcgccggctcga
tccagccgcatggcgcgcttctggtcgtcagcgaacatgatcatcgcgtcatccaggccagcgccaacgccgcggaatttctgaatctcgg
aagcgtactcggcgttccgctcgccgagatcgacggcgatctgttgatcaagatcctgccgcatctcgatcccaccgccgaaggcatgccg
gtcgcggtgcgctgccggatcggcaatccctctacggagtactgcggtctgatgcatcggcctccggaaggcgggctgatcatcgaactc
gaacgtgccggcccgtcgatcgatctgtcaggcacgctggcgccggcgctggagcggatccgcacggcgggttcactgcgcgcgctgt
gcgatgacaccgtgctgctgtttcagcagtgcaccggctacgaccgggtgatggtgtatcgtttcgatgagcaaggccacggcctggtattc
tccgagtgccatgtgcctgggctcgaatcctatttcggcaaccgctatccgtcgtcgactgtcccgcagatggcgcggcagctgtacgtgcg
gcagcgcgtccgcgtgctggtcgacgtcacctatcagccggtgccgctggagccgcggctgtcgccgctgaccgggcgcgatctcgaca
tgtcgggctgcttcctgcgctcgatgtcgccgtgccatctgcagttcctgaaggacatgggcgtgcgcgccaccctggcggtgtcgctggt
ggtcggcggcaagctgtggggcctggttgtctgtcaccattatctgccgcgcttcatccgtttcgagctgcgggcgatctgcaaacggctcg
ccgaaaggatcgcgacgcggatcaccgcgcttgagagc miRFP703 protein sequence
(SEQ ID NO: 3)
mvaghasgspafgtashsnceheeihlagsiqphgallvvsehdhrvigasanaaeflnlgsvlgvplaeidgdllikilphldptaegm
pvavrcrignpsteycglmhrppeggliieleragpsidlsgtlapalerirtagslralcddtvllfqqctgydrvmvyrfdeqghglvfse
chvpglesyfgnrypsslvpqmarqlyvrqrvrvlvdvtyqpvpleprlspltgrdldmsgcflrsmspihlqflkdmgvratlavslv
vggklwglvvchhylprfirfelraickrlaeriatritales miRFP703 DNA sequence
(SEQ ID NO: 22)
atggtagcaggtcatgcctctggcagccccgcattcgggaccgcctctcattcgaattgcgaacatgaagagatccacctcgccggctcga
tccagccgcatggcgcgcttctggtcgtcagcgaacatgatcatcgcgtcatccaggccagcgccaacgccgcggaatttctgaatctcgg
aagcgtactcggcgttccgctcgccgagatcgacggcgatctgttgatcaagatcctgccgcatctcgatcccaccgccgaaggcatgccg
gtcgcggtgcgctgccggatcggcaatccctctacggagtactgcggtctgatgcatcggcctccggaaggcgggctgatcatcgaactc
gaacgtgccggcccgtcgatcgatctgtcaggcacgctggcgccggcgctggagcggatccgcacggcgggttcactgcgcgcgctgt
gcgatgacaccgtgctgctgtttcagcagtgcaccggctacgaccgggtgatggtgtatcgtttcgatgagcaaggccacggcctggtattc
tccgagtgccatgtgcctgggctcgaatcctatttcggcaaccgctatccgtcgtcgctggtcccgcagatggcgcggcagctgtacgtgcg
gcagcgcgtccgcgtgctggtcgacgtcacctatcagccggtgccgctggagccgcggctgtcgccgctgaccgggcgcgatctcgaca
tgtcgggctgcttcctgcgctcgatgtcgccgatccatctgcagttcctgaaggacatgggcgtgcgcgccaccctggcggtgtcgctggtg
gtcggcggcaagctgtggggcctggttgtctgtcaccattatctgccgcgcttcatccgtttcgagctgcgggcgatctgcaaacggctcgc
cgaaaggatcgcgacgcggatcaccgcgcttgagagc miRFP709 protein sequence
(SEQ ID NO: 4)
mvaghasgspafgtashsnceheeihlagsiqphgallvvsehdhrviqasanaaeflnlgsvlgvplaeidgdllikilphldptaegm
pvavrcrignpsteycglmhrppeggliieleragpsidlsgtlapalerirtagslralcddtvllfqqctgydrvmvyrfdeqghglvfse
chvpglesyfgnrypssfipqmarqlyvrqrvrvlvdvtyqpvpleprlspltgrdldmsgcflrsmspihlqflkdmgvratlayslvv
ggklwglvvchhylprfirfelraickrlaeriatritales miRFP709 DNA sequence (SEQ ID NO: 23)

atggtagcaggtcatgcctctggcagccccgcattcgggaccgcctctcattcgaattgcgaacatgaagagatccacctcgccggctcga
tccagccgcatggcgcgcttctggtcgtcagcgaacatgatcatcgcgtcatccaggccagcgccaacgccgcggaatttctgaatctcgg
aagcgtactcggcgttccgctcgccgagatcgacggcgatctgttgatcaagatcctgccgcatctcgatcccaccgccgaaggcatgccg
gtcgcggtgcgctgccggatcggcaatccctctacggagtactgcggtctgatgcatcggcctccggaaggcgggctgatcatcgaactc
gaacgtgccggcccgtcgatcgatctgtcaggcacgctggcgccggcgctggagcggatccgcacgcgggttcactgcgcgcgctgt
gcgatgacaccgtgctgctgtttcagcagtgcaccggctacgacgggtgatggtgtatcgtttcgatgagcaaggccacggcctggtattc
tccgagtgccatgtgcctgggctcgaatcctatttcggcaaccgctatccgtcgtcgttcatcccgcagatggcgcggcagctgtacgtgcg
gcagcgcgtccgcgtgctggtcgacgtcacctatcagccggtgccgctggagccgcggctgtcgccgctgaccgggcgcgatctcgaca
tgtcgggctgcttcctgcgctcgatgtcgccgatccatctgcagttcctgaaggacatgggcgtgcgcgccaccctggcggtgtcgctggtg
gtcggcggcaagctgtggggcctggttgtctgtcaccattatctgccgcgcttcatccgtttcgagctgcgggcgatctgcaaacggctcgc
cgaaaggatcgcgacgcggatcaccgcgcttgagagc miRFP-PAS protein sequence (SEQ ID NO: 5)

mvaghasgspafgtashsnceheeihlagsiqphgallvvsehdhrviqasanaaeflnlgsvlgvplaeidgdllikilphldptaegm
pvavrcrignpsteycglmhrppeggliieleragp miRFP-PAS DNA sequence (SEQ ID NO: 24)

atggtagcaggtcatgcctctggcagccccgcattcgggaccgcctctcattcgaattgcgaacatgaagagatccacctcgccggctcga
tccagccgcatggcgcgcttctggtcgtcagcgaacatgatcatcgcgtcatccaggccagcgccaacgccgcggaatttctgaatctcgg
aagcgtactcggcgttccgctcgccgagatcgacggcgatctgttgatcaagatcctgccgcatctcgatcccaccgccgaaggcatgccg
gtcgcggtgcgctgccggatcggcaatccctctacggagtactgcggtctgatgcatcggcctccggaaggcgggctgatcatcgaactc
gaacgtgccggcccg miRFP-PAS1 protein sequence (SEQ ID NO: 6)

mvaghasgspafgtashsnseheeihlagsiqphgallvvsehdhrviqasanaaeflnlgsvlgvplaeidgdllikilphldptaegm
pvavrcrignpsteycglmhrppeggliieleragp miRFP-PAS1 DNA sequence (SEQ ID NO: 25)

atggtagcaggtcatgcctctggcagccccgcattcgggaccgcctctcattcgaattccgaacatgaagagatccacctcgccggctcgat
ccagccgcatggcgcgcttctggtcgtcagcgaacatgatcatcgcgtcatccaggccagcgccaacgccgcggaatttctgaatctcgga
agcgtactcggcgttccgctcgccgagatcgacggcgatctgttgatcaagatcctgccgcatctcgatcccaccgccgaaggcatgccg
gtcgcggtgcgctgccggatcggcaatccctctacggagtactgcggtctgatgcatcggcctccggaaggcgggctgatcatcgaactc
gaacgtgccggcccg miRFP-GAF670 protein sequence (SEQ ID NO: 7)

ragpsidlsgtlapalerirtagslralcddtvllfqqctgydrvmvyrfdeqghglvfsechvpglesyfgnrypsstvpqmarqlyvrqr
vrvlvdvtyqpvpleprlspltgrdldmsgcflrsmspchlqflkdmgvratlavslvvggklwglvvchhylprfirfelraickrlaeri
atritales miRFP-GAF670 DNA sequence (SEQ ID NO: 26)

cgtgccggcccgtcgatcgatctgtcaggcacgctggcgccggcgctggagcggatccgcacggcgggttcactgcgcgcgctgtgcg
atgacaccgtgctgctgtttcagcagtgcaccggctacgacgggtgatggtgtatcgtttcgatgagcaaggccacggcctggtattctcc
gagtgccatgtgcctgggctcgaatcctatttcggcaaccgctatccgtcgtcgactgtcccgcagatggcgcggcagctgtacgtgcggc
agcgcgtccgcgtgctggtcgacgtcacctatcagccggtgccgctggagccgcggctgtcgccgctgaccgggcgcgatctcgacatg
tcgggctgcttcctgcgctcgatgtcgccgtgccatctgcagttcctgaaggacatgggcgtgcgcgccaccctggcggtgtcgctggtgg -continued tcggcggcaagctgtggggcctggttgtctgtcaccattatctgccgcgcttcatccgtttcgagctgcgggcgatctgcaaacggctcgcc gaaaggatcgcgacgcggatcaccgcgcttgagagc miRFP-GAF703 protein sequence (SEQ ID NO: 8)

ragpsidlsgtlapalerirtagslralcddtvllfqqctgydrvmvyrfdeqghglvfsechvpglesyfgnrypsslvpqmarqlyvrqr vrvlvdvtyqpvpleprlspltgrdldmsgcflrsmspihlqflkdmgvratlavslvvggklwglvvchhylprfirfelraickrlaeri atritales miRFP-GAF703 DNA sequence (SEQ ID NO: 27)

cgtgccggcccgtcgatcgatctgtcaggcacgctggcgccggcgctggagcggatccgcacggcgggttcactgcgcgcgctgtgcg atgacaccgtgctgctgtttcagcagtgcaccggctacgacgggtgatggtgtatcgtttcgatgagcaaggccacggcctggtattctcc gagtgccatgtgcctgggctcgaatcctatttcggcaaccgctatccgtcgtcgctggtcccgcagatggcgcggcagctgtacgtgcggc agcgcgtccgcgtgctggtcgacgtcacctatcagccggtgccgctggagccgcggctgtcgccgctgaccgggcgcgatctcgacatg tcgggctgcttcctgcgctcgatgtcgccgatccatctgcagttcctgaaggacatgggcgtgcgcgccaccctggcggtgtcgctggtggt cggcggcaagctgtggggcctggttgtctgtcaccattatctgccgcgcttcatccgtttcgagctgcgggcgatctgcaaacggctcgccg aaaggatcgcgacgcggatcaccgcgcttgagagc miRFP-GAF709 protein sequence (SEQ ID NO: 9)

ragpsidlsgtlapalerirtagslralcddtvllfqqctgydrvmvyrfdeqghglvfsechvpglesyfgnrypssfipqmarqlyvrqr vrvlvdvtyqpvpleprlspltgrdldmsgcflrsmspihlqflkdmgvratlavslvvggklwglvvchhylprfirfelraickrlaeri atritales miRFP-GAF709 DNA sequence (SEQ ID NO: 28)

cgtgccggcccgtcgatcgatctgtcaggcacgctggcgccggcgctggagcggatccgcacggcgggttcactgcgcgcgctgtgcg atgacaccgtgctgctgtttcagcagtgcaccggctacgacgggtgatggtgtatcgtttcgatgagcaaggccacggcctggtattctcc gagtgccatgtgcctgggctcgaatcctatttcggcaaccgctatccgtcgtcgttcatcccgcagatggcgcggcagctgtacgtgcggca gcgcgtccgcgtgctggtcgacgtcacctatcagccggtgccgctggagccgcggctgtcgccgctgaccgggcgcgatctcgacatgt cgggctgcttcctgcgctcgatgtcgccgatccatctgcagttcctgaaggacatgggcgtgcgcgccaccctggcggtgtcgctggtggt cggcggcaagctgtggggcctggttgtctgtcaccattatctgccgcgcttcatccgtttcgagctgcgggcgatctgcaaacggctcgccg aaaggatcgcgacgcggatcaccgcgcttgagagc

*Rhodopseudomonas palustris* RpBphP1 PAS-GAF domains protein sequence, (SEQ ID NO: 10)

Masvaghasgspafgtadlsncereeihlagsiqphgallvvsepdhriiqasanaaeflnlgsvlgvplaeidgdllikilphldptaeg mpvavrcrignpsteydglmhrppegglıielerapppidlsgtlapalerirtagslralcddtallfqqctgydrvmvyrfdeqghgev fserhypglesyfgnrypssdipqmarrlyerqrvrvlvdvsyqpvpleprlspltgrdldmsgcflrsmspihlqylknmgvratlvvs lvvggklwglvachhylprfmhfelraicellaeaiatritales

*Rhodopseudomonas palustris* RpBphP1 PAS-GAF domains DNA sequence (SEQ ID NO: 29)

Atggctagcgtggcaggtcatgcctctggcagccccgcattcgggaccgccgatctttcgaattgcgaacgtgaagagatccacctcgcc ggctcgatccagccgcatggcgcgcttctggtcgtcagcgagccggatcatcgcatcatccaggccagcgccaacgccgcggaatttctg aatctcggaagcgtgctcggcgttccgctcgccgagatcgacggcgatctgttgatcaagatcctgccgcatctcgatcccaccgccgaag gcatgccggtcgcggtgcgctgccggatcggcaatccctccacggagtacgacggtctgatgcatcggcctccggaaggcgggctgatc atcgagctcgaacgtgccggcccgccgatcgatctgtccggcacgctggcgccggcgctggagcggatccgcacggcgggctcgctgc gcgcgctgtgcgatgacaccgcgctgctgtttcagcagtgcaccggctacgacgggtgatggtgtatcgcttcgacgagcagggccacg gcgaagtgttctccgagcgccacgtgcccgggctcgaatcctatttcggcaaccgctatccgtcgtcggacattccgcagatggcgcggcg gctgtacgagcggcagcgcgtccgcgtgctggtcgacgtcagctatcagccggtgccgctggagccgcggctgtcgccgctgaccggg cgcgatctcgacatgtcgggctgcttcctgcgctcgatgtcgccgatccatctgcagtacctgaagaacatgggcgtgcgcgccaccctgg -continued tggtgtcgctggtggtcggcggcaagctgtggggcctggttgcctgtcatcattatctgccgcgcttcatgcatttcgagctgcgggcgatct gcgaactgctcgccgaagcgatcgcgacgcggatcaccgcgcttgagagc miRFP670-2 protein sequence (SEQ ID NO: 11)

markvdltscdrepihipgsiqpcgcllacdaqavritritenagaffgretprvgelladyfgeteahalrnalaqssdpkrpalifgwrdg ltgrtfdislhrhdgtsiiefepaaaeqadnplrltrqiiartkelksleemaarvprylqamlgyhrvmlyrfaddgsgmvigeakrsdle sflgqhfpaslypqqarllylknairvvsdsrgissrivpehdasgaaldlsfahlrsispchleflrnmgvsasmslsiiidgtlwgliichh yepravpmaqrvaakrfaerlsthftaahhqr miRFP670-2 DNA sequence (SEQ ID NO: 30)

atggcgcgtaaggtcgatctcacctcctgcgatcgcgagccgatccacatccccggcagcattcagccgtgcggctgcctgctagcctgc gacgcgcaggcggtgcggatcacgcgcattacggaaaatgccggcgcgttctttggacgcgaaactccgcgggtcggtgagctactcgc cgattacttcggcgagaccgaagcccatgcgctgcgcaacgcactggcgcagtcctccgatccaaagcgaccggcgctgatcttcggttg gcgcgacggcctgaccggccgcaccttcgacatctcactgcatcgccatgacggtacatcgatcatcgagttcgagcctgcggcggccga acaggccgacaatccgctgcggctgacgcggcagatcatcgcgcgcaccaaagaactgaagtcgctcgaagagatggccgcacgggt gccgcgctatctgcaggcgatgctcggctatcaccgcgtgatgttgtaccgcttcgcggacgacggctccgggatggtgatcggcgaggc gaagcgcagcgacctcgagagctttctcggtcagcactttccggcgtcgctggtcccgcagcaggcgcggctactgtacttgaagaacgc gatccgcgtggtctcggattcgcgcggcatcagcagccggatcgtgcccgagcacgacgcctccggcgccgcgctcgatctgtcgttcgc gcacctgcgcagcatctcgccctgccatctcgaatttctgcggaacatgggcgtcagcgcctcgatgtcgctgtcgatcatcattgacggca cgctatggggattgatcatctgtcatcattacgagccgcgtgccgtgccgatggcgcagcgcgtcgcggccaagaggttcgccgagaggt tatcgactcacttcaccgccgccaccaccaacgctaa miRFP702 protein sequence (SEQ ID NO: 12)

markvdltscdrepihipgsiqpcgcllacdaqavritritenagaffgretprvgelladyfgeteahalrnalaqssdpkrpalifgwrdg ltgrtfdislhrhdgtsiiefepaaaeqadnplrltrqiiartkelksleemaarvprylqamlgyhrvmlyrfaddgsgkvigeakrsdles flgqhfpaslypqqarllylknairvvsdsrgissrivpehdasgaaldlsfahlrsispihleflrnmgvsasmslsiiidgtlwgliichhy epravpmaqrvaakrfaerlsthftaahhqr miRFP702 DNA sequence (SEQ ID NO: 31)

atggcgcgtaaggtcgatctcacctcctgcgatcgcgagccgatccacatccccggcagcattcagccgtgcggctgcctgctagcctgc gacgcgcaggcggtgcggatcacgcgcattacggaaaatgccggcgcgttctttggacgcgaaactccgcgggtcggtgagctactcgc cgattacttcggcgagaccgaagcccatgcgctgcgcaacgcactggcgcagtcctccgatccaaagcgaccggcgctgatcttcggttg gcgcgacggcctgaccggccgcaccttcgacatctcgctgcatcgccatgacggtacatcgatcatcgagttcgagcctgcggcggccga acaggccgacaatccgctgcggctgacgcggcagatcatcgcgcgcaccaaagaactgaagtcgctcgaagagatggccgcacgggt gccgcgctatctgcaggcgatgctcggctatcaccgcgtgatgttgtaccgcttcgcggacgacggctccggcaaagtgatcggcgaggc gaagcgcagcgacctcgagagctttctcggtcagcactttccggcgtcgctggtcccgcagcaggcgcggctactgtacttgaagaacgc gatccgcgtggtctcggattcgcgcggcatcagcagccggatcgtgcccgagcacgacgcctccggcgccgcgcttgatctgtcgttcgc gcacctgcgcagcatctcgcctatccatctcgaatttctgcggaacatgggcgtcagcgcctcgatgtcgctgtcgatcatcattgacggcac gctatggggattgatcatctgtcatcattacgagccgcgtgccgtgccgatggcgcagcgcgtcgcggccaagaggttcgccgagaggtt atcgactcacttcaccgccgccaccaccaacgctaa miRFP682 protein sequence (SEQ ID NO: 13)

maegsvarqpdlltcddepihipgaiqphglllalaadmtivagsdnlpeltglaigaligrsaadvfdsethnrltialaepgaavgapitv gftmrkdagfigswhrhdqlifleleppqrdvaepqaffrrtnsairrlqaaetlesacaaaaqevrkitgfdrvmiyrfasdfsgvviaed rcaevesklglhypasavpaqarrlytinpvriipdinyrpvpvtpdlnpvtgrpidlsfailrsvspchlefmrnigmhgtmsisilrgerl wglivchhrtpyyvdldgrqackrvaerlatqigvmee miRFP682 DNA sequence (SEQ ID NO: 32)

atggcggaaggatccgtcgccaggcagcctgacctcttgacctgcgacgatgagccgatccatatccccggtgccatccaaccgcatgga ctgctgctcgccctcgccgccgacatgacgatcgttgccggcagcgacaaccttcccgaactcaccggactggcgatcggcgccctgatc ggccgctctgcggccgatgtcttcgactcggagacgcacaaccgtctgacgatcgccttggccgagcccggggcggccgtcggagcac cgatcactgtcggcttcacgatgcgaaaggacgcaggcttcatcggctcctggcatcgccatgatcagctcatcttcctcgagctcgagcct ccccagcggacgtcgccgagccgcaggcgttcttccgccgcaccaacagcgccatccgccgcctgcaggccgccgaaaccttggaaa gcgcctgcgccgccgcggcgcaagaggtgcggaagattaccggcttcgatcgggtgatgatctatcgcttcgcctccgacttcagcgggg tggtgatcgcagaggatcgatgcgccgaggtcgagtcaaaactaggcctgcactatcctgcctcagcggtgccggcgcaggcccgtcgg ctctataccatcaacccggtacggatcattcccgatatcaattatcggccggtgccggtcaccccagacctcaatccggtcaccgggcggcc gattgatcttagcttcgccatcctgcgcagcgtctcgccctgccatttggagttcatgcgcaacataggcatgcacggcacgatgtcgatctc gattttgcgcggcgagcgactgtggggattgatcgtttgccatcaccgaacgccgtactacgtcgatctcgatggccgccaagcctgcaag agggtcgccgagaggctggccactcagatcggcgtgatggaagagtga miRFP713 protein sequence (SEQ ID NO: 14)

maegsvarqpdlltcddepihipgaiqphglllalaadmtivagsdnlpeltglaigaligrsaadvfdsethnrltialaepgaavgapitv gftmrkdagfigswhrhdqliflefleppqrdvaepqaffrrtnsairrlqaaetlesacaaaaqevrkitgfdrvmiyrfasdfsgeviaedr caevesklglhypastvpaqarrlytinpvriipdinyrpvpvtpdlnpvtgrpidlsfailrsvspvhlefmrnigmhgtmsisilrgerl wglivchhrtpyyvdldgrqackrvaerlatqigvmee miRFP713 DNA sequence (SEQ ID NO: 33)

atggcggaaggatccgtcgccaggcagcctgacctcttgacctgcgacgatgagccgatccatatccccggtgccatccaaccgcatgga ctgctgctcgccctcgccgccgacatgacgatcgttgccggcagcgacaaccttcccgaactcaccggactggcgatcggcgccctgatc ggccgctctgcggccgatgtcttcgactcggagacgcacaaccgtctgacgatcgccttggccgagcccggggcggccgtcggagcac cgatcactgtcggcttcacgatgcgaaaggacgcaggcttcatcggctcctggcatcgccatgatcagctcatcttcctcgagctcgagcct ccccagcggacgtcgccgagccgcaggcgttcttccgccgcaccaacagcgccatccgccgcctgcaggccgccgaaaccttggaaa gcgcctgcgccgccgcggcgcaagaggtgcggaagattaccggcttcgatcgggtgatgatctatcgcttcgcctccgacttcagcggcg aagtgatcgcagaggatcggtgcgccgaggtcgagtcaaaactaggcctgcactatcctgcctcaaccgtgccggcgcaggcccgtcgg ctctataccatcaacccggtacggatcattcccgatatcaattatcggccggtgccggtcaccccagacctcaatccggtcaccgggcggcc gattgatcttagatcgccatcctgcgcagcgtctcgcccgtccatctggaattcatgcgcaacataggcatgcacggcacgatgtcgatctc gattttgcgcggcgagcgactgtggggattgatcgtttgccatcaccgaacgccgtactacgtcgatctcgatggccgccaagcctgcaag agggtcgccgagaggctggccactcagatcggcgtgatggaagagtga miRFP720 protein sequence (SEQ ID NO: 15)

maegsvarqpdlltcddepihipgaiqphglllalaadmtivagsdnlpeltglaigaligrsaadvfdsethnrltialaepgaavgapitv gftmrkdagfigswhrhdqliflefleppqrdvaepqaffrrtnsairrlqaaetlesacaaaaqevrkitgfdrvmiyrfasdfsgsviaedr caevesklglhypasfipaqarrlytinpvriipdinyrpvpvtpdlnpvtgrpidlsfailrsvspnhlefmrnigmhgtmsisilrgerl wglivchhrtpyyvdldgrqackrvaerlatqigvmee miRFP720 DNA sequence (SEQ ID NO: 34)

atggcggaaggatccgtcgccaggcagcctgacctcttgacctgcgacgatgagccgatccatatccccggtgccatccaaccgcatgga ctgctgctcgccctcgccgccgacatgacgatcgttgccggcagcgacaaccttcccgaactcaccggactggcgatcggcgccctgatc ggccgctctgcggccgatgtcttcgactcggagacgcacaaccgtctgacgatcgccttggccgagcccggggcggccgtcggagcac cgatcactgtcggcttcacgatgcgaaaggacgcaggcttcatcggctcctggcatcgccatgatcagctcatcttcctggagctggagcct

```
ccccagcgggacgtcgccgagccgcaggcgttcttccgccgcaccaacagcgccatccgccgcctgcaggccgccgaaaccttggaaa gcgcctgcgccgccgcggcgcaagaggtgcggaagattaccggcttcgatcgggtgatgatctatcgcttcgcctccgacttcagcgggt ccgtgatcgcagaggatcggtgcgccgaggtcgagtcaaaactaggcctgcactatcctgcctcattcatcccggcgcaggcccgtcggc tctataccatcaacccggtacggatcattcccgatatcaattatcggccggtgccggtcaccccagacctcaatccggtcaccgggcggcc gattgatcttagcttcgccatcctgcgcagcgtctcgcccaaccatctggagttcatgcgcaacataggcatgcacggcacgatgtcgatctc gattttgcgcggcgagcgactgtggggattgatcgtttgccatcaccgaacgccgtactacgtcgatctcgatggccgccaagcctgcaag agggtcgccgagaggctggccactcagatcggcgtgatggaagagtga
```

*Rhodopseudomonas palustris* RpBphP6 PAS-GAF domains protein sequence
(SEQ ID NO: 16)

```
mprkvdltscdrepihipgsiqpcgcllacdaqavritrisenagaffgretprvgelladyfgeteahalrnalaqssdpkrpalifgwrd gltgrtfdislhrhdgtsivefepaaadqadnplrltrqiiartkelksleemaarvprylqamlgyhrvmmyrfaddgsgkvigeakrsd lesflgqhfpasdipqqarllylknairvisdsrgissrivperdasgaaldlsfahlrsvspihleylrnmgvsasmslsiiidgtlwgliach hyepravpmaqrvaaemfadffslhftaahhqr
```

*Rhodopseudomonas palustris* RpBphP6 PAS-GAF domains DNA sequence
(SEQ ID NO: 35)

```
atgccgcgtaaggtcgatctcacctcctgcgatcgcgagccgatccacatccccggcagcattcagccgtgcggctgcctgctggcctgc gacgcgcaggcggtgcggatcacgcgcatttcggaaaatgccggcgcgttctttggacgcgaaactccgcgggtcggtgagctactcgc cgattacttcggcgagaccgaagcccatgcgctgcgcaacgcactggcgcagtcctccgatccaaagcggccggcgctgatcttcggttg gcgcgacggcctgaccggccgcaccttcgacatctcgctgcatcgccatgacggtacatcgatcgtcgaattcgagcctgcggcggcga tcaggccgacaatccgctgcggctgacgcggcagatcatcgcgcgcaccaaagaactgaagtcgctcgaggagatggccgcacgggtg ccgcgctatctgcaggcgatgctcggctataccgcgtgatgatgtaccgcttcgcggacgacggctccggcaaagtgatcggcgaggc gaagcgcagcgacctcgagagctttctcggtcagcactttccggcgtcggacatcccgcagcaggcgcggctgctgtacttgaagaacgc gatccgcgtgatctcggattcgcgcggcatcagcagccggatcgtgcccgagcgcgacgcctccggccgcgctcgatctgtcgttcgc gcacctgcgcagcgtctcgcccatccatctcgaatatctgcggaacatgggcgtcagcgcctcgatgtcgctgtcgatcatcattgacggca cgctatgggattgatcgcctgtcatcattacgagccgcgtgccgtgccgatggcgcagcgcgtcgccgccgaaatgttcgccgacttcttc tcgctgcacttcaccgccgccaccaccaacgc
```

*Rhodopseudomonas palustris* RpBphP2 PAS-GAF domains protein sequence
(SEQ ID NO: 17)

```
mtegsvarqpdlstcddepihipgaiqphglllalaadmtivagsdnlpeltglaigaligrsaadvfdsethnrltialaepgaavgapia vgftmrkdagfvgswhrhdqlvflelepppqrdvaepqaffrrtnsairrlqaaetlesacaaaaqevreitgfdrvmiyrfasdfsgevia edrcaevesylglhfpasdipaqarrlytinpvriipdinyrpvpvtpdlnpvtgrpidlsfailrsvspvhleymrnigmhgtmsisilrg erlwgliachhrkpnyvdldgrqacelvaqvlawqigymee
```

*Rhodopseudomonas palustris* RpBphP2 PAS-GAF domains DNA sequence
(SEQ ID NO: 36)

```
atgacagaaggatccgtcgccaggcagcctgacctctcgacctgcgacgatgagccgatccatatccccggtgccatccaaccgcatgga ctgctgctcgccctcgccgccgacatgacgatcgttgccggcagcgacaaccttcccgaactcaccggactggcgatcggcgccctgatc ggccgctctgcggccgatgtcttcgactcggagacgcacaaccgtctgacgatcgccttggccgagcccggggcggccgtcggagcac cgatcgctgtcggcttcacgatgcgaaaggacgcaggcttcgtcggctcctggcatcgccatgatcagctcgtcttcctcgagctcgagcct ccccagcgggacgtcgccgagccgcaggcgttcttccgccgcaccaacagcgccatccgccgcctgcaggccgccgaaaccttggaaa gcgcctgcgccgccgcggcgcaagaggtgcgggagattaccggcttcgatcgggtgatgatctatcgcttcgcctccgacttcagcggcg aagtgatcgcagaggatcggtgcgccgaggtcgagtcatatctaggcctgcactttcctgcctcagacatcccggcgcaggcccgtcggct ctataccatcaacccggtacggatcattcccgatatcaattatcggccggtgccggtcacccagacctcaatccggtcaccgggcggccg attgatcttagatcgccatcctgcgcagcgtctcgcccgtccatctggaatacatgcgcaacatcggcatgcacggcacgatgtcgatctcg attttgcgcggcgagcgactgtggggattgatcgcctgccatcaccgaaagccgaactacgtcgatctcgatggccgccaagcctgcgag ctagtcgcccaggttctggcctggcagatcggcgtgatggaagagca
```

What is claimed is:

1. An isolated nucleic acid, encoding a monomeric near-infrared fluorescent protein comprising consecutive amino acid residues, wherein the said protein has 98.5% or greater identity with SEQ ID NO:15 and comprises at least one of D301, E301, K301, R301, D302, E302, K302, R302, D305, E305, K305, R305, D306, E306, K306, R306, T309, and wherein the amino acid positions correspond to amino acid residue number positions in SEQ ID NO:15.

2. A vector comprising the nucleic acid according to claim 1.

3. An expression cassette comprising: (a) a transcriptional initiation region functional in an expression host; (b) the nucleic acid according to claim 1; and (c) a transcriptional termination region functional in said expression host.

4. A host cell or progeny thereof, comprising the expression cassette according to claim 3 as part of an extrachromosomal element or integrated into the genome of a host cell as a result of introduction of the expression cassette into the host cell.

5. A transgenic cell, or progeny thereof, comprising the nucleic acid according to claim 1.

6. A kit comprising the nucleic acid according claim 1 and written instructions for use.

7. The nucleic acid of claim 1, wherein protein is miRFP682 (SEQ ID NO:13), miRFP713 (SEQ ID NO:14), miRFP720 (SEQ ID NO:15).

* * * * *

SEQUENCE LISTING

<160> NUMBER OF SEQ ID NOS: 36

<210> SEQ ID NO 1
<211> LENGTH: 315
<212> TYPE: PRT
<213> ORGANISM: Artificial Sequence
<220> FEATURE:
<223> OTHER INFORMATION: Artificial sequence based on bacterial sequence

<400> SEQUENCE: 1

Met Val Ala Gly His Ala Ser Gly Ser Pro Ala Phe Gly Thr Ala Ser
1               5                   10                  15

His Ser Asn Ser Glu His Glu Glu Ile His Leu Ala Gly Ser Ile Gln
            20                  25                  30

Pro His Gly Ala Leu Leu Val Val Ser Glu His Asp His Arg Val Ile
        35                  40                  45

Gln Ala Ser Ala Asn Ala Ala Glu Phe Leu Asn Leu Gly Ser Val Leu
    50                  55                  60

Gly Val Pro Leu Ala Glu Ile Asp Gly Asp Leu Leu Ile Lys Ile Leu
65                  70                  75                  80

Pro His Leu Asp Pro Thr Ala Glu Gly Met Pro Val Ala Val Arg Cys
                85                  90                  95

Arg Ile Gly Asn Pro Ser Thr Glu Tyr Cys Gly Leu Met His Arg Pro
            100                 105                 110

Pro Glu Gly Gly Leu Ile Ile Glu Leu Glu Arg Ala Gly Pro Ser Ile
        115                 120                 125

Asp Leu Ser Gly Thr Leu Ala Pro Ala Leu Glu Arg Ile Arg Thr Ala
    130                 135                 140

Gly Ser Leu Arg Ala Leu Cys Asp Asp Thr Val Leu Leu Phe Gln Gln
145                 150                 155                 160

Cys Thr Gly Tyr Asp Arg Val Met Val Tyr Arg Phe Asp Glu Gln Gly
                165                 170                 175

His Gly Leu Val Phe Ser Glu Cys His Val Pro Gly Leu Glu Ser Tyr
            180                 185                 190

Phe Gly Asn Arg Tyr Pro Ser Ser Thr Val Pro Gln Met Ala Arg Gln
        195                 200                 205

Leu Tyr Val Arg Gln Arg Val Arg Val Leu Val Asp Val Thr Tyr Gln
    210                 215                 220

Pro Val Pro Leu Glu Pro Arg Leu Ser Pro Leu Thr Gly Arg Asp Leu
225                 230                 235                 240

Asp Met Ser Gly Cys Phe Leu Arg Ser Met Ser Pro Cys His Leu Gln
                245                 250                 255

Phe Leu Lys Asp Met Gly Val Arg Ala Thr Leu Ala Val Ser Leu Val
            260                 265                 270

Val Gly Gly Lys Leu Trp Gly Leu Val Val Cys His His Tyr Leu Pro
        275                 280                 285

Arg Phe Ile Arg Phe Glu Leu Arg Ala Ile Cys Lys Arg Leu Ala Glu
    290                 295                 300

Arg Ile Ala Thr Arg Ile Thr Ala Leu Glu Ser
305                 310                 315

<210> SEQ ID NO 2
<211> LENGTH: 315
<212> TYPE: PRT
<213> ORGANISM: Artificial Sequence
<220> FEATURE:
<223> OTHER INFORMATION: Artificial sequence based on bacterial sequence

<400> SEQUENCE: 2

Met Val Ala Gly His Ala Ser Gly Ser Pro Ala Phe Gly Thr Ala Ser
1               5                   10                  15

His Ser Asn Cys Glu His Glu Glu Ile His Leu Ala Gly Ser Ile Gln
            20                  25                  30

Pro His Gly Ala Leu Leu Val Val Ser Glu His Asp His Arg Val Ile
        35                  40                  45

Gln Ala Ser Ala Asn Ala Ala Glu Phe Leu Asn Leu Gly Ser Val Leu
    50                  55                  60

Gly Val Pro Leu Ala Glu Ile Asp Gly Asp Leu Leu Ile Lys Ile Leu
65                  70                  75                  80

Pro His Leu Asp Pro Thr Ala Glu Gly Met Pro Val Ala Val Arg Cys
                85                  90                  95

Arg Ile Gly Asn Pro Ser Thr Glu Tyr Cys Gly Leu Met His Arg Pro
            100                 105                 110

Pro Glu Gly Gly Leu Ile Ile Glu Leu Glu Arg Ala Gly Pro Ser Ile
        115                 120                 125

Asp Leu Ser Gly Thr Leu Ala Pro Ala Leu Glu Arg Ile Arg Thr Ala
    130                 135                 140

Gly Ser Leu Arg Ala Leu Cys Asp Asp Thr Val Leu Leu Phe Gln Gln
145                 150                 155                 160

Cys Thr Gly Tyr Asp Arg Val Met Val Tyr Arg Phe Asp Glu Gln Gly
                165                 170                 175

His Gly Leu Val Phe Ser Glu Cys His Val Pro Gly Leu Glu Ser Tyr
            180                 185                 190

Phe Gly Asn Arg Tyr Pro Ser Ser Thr Val Pro Gln Met Ala Arg Gln
        195                 200                 205

Leu Tyr Val Arg Gln Arg Val Arg Val Leu Val Asp Val Thr Tyr Gln
    210                 215                 220

Pro Val Pro Leu Glu Pro Arg Leu Ser Pro Leu Thr Gly Arg Asp Leu
225                 230                 235                 240

Asp Met Ser Gly Cys Phe Leu Arg Ser Met Ser Pro Cys His Leu Gln
                245                 250                 255

Phe Leu Lys Asp Met Gly Val Arg Ala Thr Leu Ala Val Ser Leu Val
            260                 265                 270

Val Gly Gly Lys Leu Trp Gly Leu Val Val Cys His His Tyr Leu Pro
        275                 280                 285

Arg Phe Ile Arg Phe Glu Leu Arg Ala Ile Cys Lys Arg Leu Ala Glu
    290                 295                 300

Arg Ile Ala Thr Arg Ile Thr Ala Leu Glu Ser
305                 310                 315

<210> SEQ ID NO 3
<211> LENGTH: 315
<212> TYPE: PRT
<213> ORGANISM: Artificial Sequence
<220> FEATURE:
<223> OTHER INFORMATION: Artificial sequence based on bacterial sequence

<400> SEQUENCE: 3

Met Val Ala Gly His Ala Ser Gly Ser Pro Ala Phe Gly Thr Ala Ser
1               5                   10                  15

His Ser Asn Cys Glu His Glu Glu Ile His Leu Ala Gly Ser Ile Gln
            20                  25                  30

```
Pro His Gly Ala Leu Leu Val Val Ser Glu His Asp His Arg Val Ile
         35                  40                  45

Gln Ala Ser Ala Asn Ala Ala Glu Phe Leu Asn Leu Gly Ser Val Leu
 50                  55                  60

Gly Val Pro Leu Ala Glu Ile Asp Gly Asp Leu Leu Ile Lys Ile Leu
 65                  70                  75                  80

Pro His Leu Asp Pro Thr Ala Glu Gly Met Pro Val Ala Val Arg Cys
                 85                  90                  95

Arg Ile Gly Asn Pro Ser Thr Glu Tyr Cys Gly Leu Met His Arg Pro
            100                 105                 110

Pro Glu Gly Gly Leu Ile Ile Glu Leu Glu Arg Ala Gly Pro Ser Ile
        115                 120                 125

Asp Leu Ser Gly Thr Leu Ala Pro Ala Leu Glu Arg Ile Arg Thr Ala
130                 135                 140

Gly Ser Leu Arg Ala Leu Cys Asp Asp Thr Val Leu Leu Phe Gln Gln
145                 150                 155                 160

Cys Thr Gly Tyr Asp Arg Val Met Val Tyr Arg Phe Asp Glu Gln Gly
                165                 170                 175

His Gly Leu Val Phe Ser Glu Cys His Val Pro Gly Leu Glu Ser Tyr
            180                 185                 190

Phe Gly Asn Arg Tyr Pro Ser Ser Leu Val Pro Gln Met Ala Arg Gln
        195                 200                 205

Leu Tyr Val Arg Gln Arg Val Arg Val Leu Val Asp Val Thr Tyr Gln
    210                 215                 220

Pro Val Pro Leu Glu Pro Arg Leu Ser Pro Leu Thr Gly Arg Asp Leu
225                 230                 235                 240

Asp Met Ser Gly Cys Phe Leu Arg Ser Met Ser Pro Ile His Leu Gln
                245                 250                 255

Phe Leu Lys Asp Met Gly Val Arg Ala Thr Leu Ala Val Ser Leu Val
            260                 265                 270

Val Gly Gly Lys Leu Trp Gly Leu Val Val Cys His His Tyr Leu Pro
        275                 280                 285

Arg Phe Ile Arg Phe Glu Leu Arg Ala Ile Cys Lys Arg Leu Ala Glu
    290                 295                 300

Arg Ile Ala Thr Arg Ile Thr Ala Leu Glu Ser
305                 310                 315

<210> SEQ ID NO 4
<211> LENGTH: 315
<212> TYPE: PRT
<213> ORGANISM: Artificial Sequence
<220> FEATURE:
<223> OTHER INFORMATION: Artificial sequence based on bacterial sequence

<400> SEQUENCE: 4

Met Val Ala Gly His Ala Ser Gly Ser Pro Ala Phe Gly Thr Ala Ser
1               5                   10                  15

His Ser Asn Cys Glu His Glu Ile His Leu Ala Gly Ser Ile Gln
            20                  25                  30

Pro His Gly Ala Leu Leu Val Val Ser Glu His Asp His Arg Val Ile
         35                  40                  45

Gln Ala Ser Ala Asn Ala Ala Glu Phe Leu Asn Leu Gly Ser Val Leu
 50                  55                  60

Gly Val Pro Leu Ala Glu Ile Asp Gly Asp Leu Leu Ile Lys Ile Leu
 65                  70                  75                  80
```

```
Pro His Leu Asp Pro Thr Ala Glu Gly Met Pro Val Ala Val Arg Cys
            85                  90                  95

Arg Ile Gly Asn Pro Ser Thr Glu Tyr Cys Gly Leu Met His Arg Pro
        100                 105                 110

Pro Glu Gly Gly Leu Ile Ile Glu Leu Glu Arg Ala Gly Pro Ser Ile
    115                 120                 125

Asp Leu Ser Gly Thr Leu Ala Pro Ala Leu Glu Arg Ile Arg Thr Ala
130                 135                 140

Gly Ser Leu Arg Ala Leu Cys Asp Asp Thr Val Leu Leu Phe Gln Gln
145                 150                 155                 160

Cys Thr Gly Tyr Asp Arg Val Met Val Tyr Arg Phe Asp Glu Gln Gly
                165                 170                 175

His Gly Leu Val Phe Ser Glu Cys His Val Pro Gly Leu Glu Ser Tyr
            180                 185                 190

Phe Gly Asn Arg Tyr Pro Ser Ser Phe Ile Pro Gln Met Ala Arg Gln
        195                 200                 205

Leu Tyr Val Arg Gln Arg Val Arg Val Leu Val Asp Val Thr Tyr Gln
    210                 215                 220

Pro Val Pro Leu Glu Pro Arg Leu Ser Pro Leu Thr Gly Arg Asp Leu
225                 230                 235                 240

Asp Met Ser Gly Cys Phe Leu Arg Ser Met Ser Pro Ile His Leu Gln
                245                 250                 255

Phe Leu Lys Asp Met Gly Val Arg Ala Thr Leu Ala Val Ser Leu Val
            260                 265                 270

Val Gly Gly Lys Leu Trp Gly Leu Val Val Cys His His Tyr Leu Pro
        275                 280                 285

Arg Phe Ile Arg Phe Glu Leu Arg Ala Ile Cys Lys Arg Leu Ala Glu
    290                 295                 300

Arg Ile Ala Thr Arg Ile Thr Ala Leu Glu Ser
305                 310                 315

<210> SEQ ID NO 5
<211> LENGTH: 126
<212> TYPE: PRT
<213> ORGANISM: Artificial Sequence
<220> FEATURE:
<223> OTHER INFORMATION: Artificial sequence based on bacterial sequence

<400> SEQUENCE: 5

Met Val Ala Gly His Ala Ser Gly Ser Pro Ala Phe Gly Thr Ala Ser
1               5                   10                  15

His Ser Asn Cys Glu His Glu Ile His Leu Ala Gly Ser Ile Gln
            20                  25                  30

Pro His Gly Ala Leu Leu Val Val Ser Glu His Asp His Arg Val Ile
        35                  40                  45

Gln Ala Ser Ala Asn Ala Ala Glu Phe Leu Asn Leu Gly Ser Val Leu
    50                  55                  60

Gly Val Pro Leu Ala Glu Ile Asp Gly Asp Leu Leu Ile Lys Ile Leu
65                  70                  75                  80

Pro His Leu Asp Pro Thr Ala Glu Gly Met Pro Val Ala Val Arg Cys
                85                  90                  95

Arg Ile Gly Asn Pro Ser Thr Glu Tyr Cys Gly Leu Met His Arg Pro
            100                 105                 110

Pro Glu Gly Gly Leu Ile Ile Glu Leu Glu Arg Ala Gly Pro
        115                 120                 125
```

<210> SEQ ID NO 6
<211> LENGTH: 126
<212> TYPE: PRT
<213> ORGANISM: Artificial Sequence
<220> FEATURE:
<223> OTHER INFORMATION: Artificial sequence based on bacterial sequence

<400> SEQUENCE: 6

```
Met Val Ala Gly His Ala Ser Gly Ser Pro Ala Phe Gly Thr Ala Ser
1               5                   10                  15

His Ser Asn Ser Glu His Glu Glu Ile His Leu Ala Gly Ser Ile Gln
            20                  25                  30

Pro His Gly Ala Leu Leu Val Val Ser Glu His Asp His Arg Val Ile
        35                  40                  45

Gln Ala Ser Ala Asn Ala Ala Glu Phe Leu Asn Leu Gly Ser Val Leu
    50                  55                  60

Gly Val Pro Leu Ala Glu Ile Asp Gly Asp Leu Leu Ile Lys Ile Leu
65                  70                  75                  80

Pro His Leu Asp Pro Thr Ala Glu Gly Met Pro Val Ala Val Arg Cys
                85                  90                  95

Arg Ile Gly Asn Pro Ser Thr Glu Tyr Cys Gly Leu Met His Arg Pro
            100                 105                 110

Pro Glu Gly Gly Leu Ile Ile Glu Leu Glu Arg Ala Gly Pro
        115                 120                 125
```

<210> SEQ ID NO 7
<211> LENGTH: 193
<212> TYPE: PRT
<213> ORGANISM: Artificial Sequence
<220> FEATURE:
<223> OTHER INFORMATION: Artificial sequence based on bacterial sequence

<400> SEQUENCE: 7

```
Arg Ala Gly Pro Ser Ile Asp Leu Ser Gly Thr Leu Ala Pro Ala Leu
1               5                   10                  15

Glu Arg Ile Arg Thr Ala Gly Ser Leu Arg Ala Leu Cys Asp Asp Thr
            20                  25                  30

Val Leu Leu Phe Gln Gln Cys Thr Gly Tyr Asp Arg Val Met Val Tyr
        35                  40                  45

Arg Phe Asp Glu Gln Gly His Gly Leu Val Phe Ser Glu Cys His Val
    50                  55                  60

Pro Gly Leu Glu Ser Tyr Phe Gly Asn Arg Tyr Pro Ser Ser Thr Val
65                  70                  75                  80

Pro Gln Met Ala Arg Gln Leu Tyr Val Arg Gln Arg Val Arg Val Leu
                85                  90                  95

Val Asp Val Thr Tyr Gln Pro Val Pro Leu Glu Pro Arg Leu Ser Pro
            100                 105                 110

Leu Thr Gly Arg Asp Leu Asp Met Ser Gly Cys Phe Leu Arg Ser Met
        115                 120                 125

Ser Pro Cys His Leu Gln Phe Leu Lys Asp Met Gly Val Arg Ala Thr
    130                 135                 140

Leu Ala Val Ser Leu Val Val Gly Gly Lys Leu Trp Gly Leu Val Val
145                 150                 155                 160

Cys His His Tyr Leu Pro Arg Phe Ile Arg Phe Glu Leu Arg Ala Ile
                165                 170                 175

Cys Lys Arg Leu Ala Glu Arg Ile Ala Thr Arg Ile Thr Ala Leu Glu
            180                 185                 190
```

Ser

<210> SEQ ID NO 8
<211> LENGTH: 193
<212> TYPE: PRT
<213> ORGANISM: Artificial Sequence
<220> FEATURE:
<223> OTHER INFORMATION: Artificial sequence based on bacterial sequence

<400> SEQUENCE: 8

```
Arg Ala Gly Pro Ser Ile Asp Leu Ser Gly Thr Leu Ala Pro Ala Leu
1               5                   10                  15
Glu Arg Ile Arg Thr Ala Gly Ser Leu Arg Ala Leu Cys Asp Asp Thr
            20                  25                  30
Val Leu Leu Phe Gln Gln Cys Thr Gly Tyr Asp Arg Val Met Val Tyr
        35                  40                  45
Arg Phe Asp Glu Gln Gly His Gly Leu Val Phe Ser Glu Cys His Val
    50                  55                  60
Pro Gly Leu Glu Ser Tyr Phe Gly Asn Arg Tyr Pro Ser Ser Leu Val
65                  70                  75                  80
Pro Gln Met Ala Arg Gln Leu Tyr Val Arg Gln Arg Val Arg Val Leu
                85                  90                  95
Val Asp Val Thr Tyr Gln Pro Val Pro Leu Glu Pro Arg Leu Ser Pro
            100                 105                 110
Leu Thr Gly Arg Asp Leu Asp Met Ser Gly Cys Phe Leu Arg Ser Met
        115                 120                 125
Ser Pro Ile His Leu Gln Phe Leu Lys Asp Met Gly Val Arg Ala Thr
    130                 135                 140
Leu Ala Val Ser Leu Val Val Gly Gly Lys Leu Trp Gly Leu Val Val
145                 150                 155                 160
Cys His His Tyr Leu Pro Arg Phe Ile Arg Phe Glu Leu Arg Ala Ile
                165                 170                 175
Cys Lys Arg Leu Ala Glu Arg Ile Ala Thr Arg Ile Thr Ala Leu Glu
            180                 185                 190
Ser
```

<210> SEQ ID NO 9
<211> LENGTH: 193
<212> TYPE: PRT
<213> ORGANISM: Artificial Sequence
<220> FEATURE:
<223> OTHER INFORMATION: Artificial sequence based on bacterial sequence

<400> SEQUENCE: 9

```
Arg Ala Gly Pro Ser Ile Asp Leu Ser Gly Thr Leu Ala Pro Ala Leu
1               5                   10                  15
Glu Arg Ile Arg Thr Ala Gly Ser Leu Arg Ala Leu Cys Asp Asp Thr
            20                  25                  30
Val Leu Leu Phe Gln Gln Cys Thr Gly Tyr Asp Arg Val Met Val Tyr
        35                  40                  45
Arg Phe Asp Glu Gln Gly His Gly Leu Val Phe Ser Glu Cys His Val
    50                  55                  60
Pro Gly Leu Glu Ser Tyr Phe Gly Asn Arg Tyr Pro Ser Ser Phe Ile
65                  70                  75                  80
Pro Gln Met Ala Arg Gln Leu Tyr Val Arg Gln Arg Val Arg Val Leu
                85                  90                  95
```

```
Val Asp Val Thr Tyr Gln Pro Val Pro Leu Glu Pro Arg Leu Ser Pro
            100                 105                 110

Leu Thr Gly Arg Asp Leu Asp Met Ser Gly Cys Phe Leu Arg Ser Met
        115                 120                 125

Ser Pro Ile His Leu Gln Phe Leu Lys Asp Met Gly Val Arg Ala Thr
    130                 135                 140

Leu Ala Val Ser Leu Val Val Gly Gly Lys Leu Trp Gly Leu Val Val
145                 150                 155                 160

Cys His His Tyr Leu Pro Arg Phe Ile Arg Phe Glu Leu Arg Ala Ile
                165                 170                 175

Cys Lys Arg Leu Ala Glu Arg Ile Ala Thr Arg Ile Thr Ala Leu Glu
            180                 185                 190

Ser

<210> SEQ ID NO 10
<211> LENGTH: 317
<212> TYPE: PRT
<213> ORGANISM: Artificial Sequence
<220> FEATURE:
<223> OTHER INFORMATION: Artificial sequence based on bacterial sequence

<400> SEQUENCE: 10

Met Ala Ser Val Ala Gly His Ala Ser Gly Ser Pro Ala Phe Gly Thr
1               5                   10                  15

Ala Asp Leu Ser Asn Cys Glu Arg Glu Ile His Leu Ala Gly Ser
            20                  25                  30

Ile Gln Pro His Gly Ala Leu Leu Val Val Ser Glu Pro Asp His Arg
        35                  40                  45

Ile Ile Gln Ala Ser Ala Asn Ala Ala Glu Phe Leu Asn Leu Gly Ser
    50                  55                  60

Val Leu Gly Val Pro Leu Ala Glu Ile Asp Gly Asp Leu Leu Ile Lys
65                  70                  75                  80

Ile Leu Pro His Leu Asp Pro Thr Ala Glu Gly Met Pro Val Ala Val
                85                  90                  95

Arg Cys Arg Ile Gly Asn Pro Ser Thr Glu Tyr Asp Gly Leu Met His
            100                 105                 110

Arg Pro Pro Glu Gly Gly Leu Ile Ile Glu Leu Glu Arg Ala Gly Pro
        115                 120                 125

Pro Ile Asp Leu Ser Gly Thr Leu Ala Pro Ala Leu Glu Arg Ile Arg
    130                 135                 140

Thr Ala Gly Ser Leu Arg Ala Leu Cys Asp Asp Thr Ala Leu Leu Phe
145                 150                 155                 160

Gln Gln Cys Thr Gly Tyr Asp Arg Val Met Val Tyr Arg Phe Asp Glu
                165                 170                 175

Gln Gly His Gly Glu Val Phe Ser Glu Arg His Val Pro Gly Leu Glu
            180                 185                 190

Ser Tyr Phe Gly Asn Arg Tyr Pro Ser Ser Asp Ile Pro Gln Met Ala
        195                 200                 205

Arg Arg Leu Tyr Glu Arg Gln Arg Val Arg Val Leu Val Asp Val Ser
    210                 215                 220

Tyr Gln Pro Val Pro Leu Glu Pro Arg Leu Ser Pro Leu Thr Gly Arg
225                 230                 235                 240

Asp Leu Asp Met Ser Gly Cys Phe Leu Arg Ser Met Ser Pro Ile His
                245                 250                 255

Leu Gln Tyr Leu Lys Asn Met Gly Val Arg Ala Thr Leu Val Val Ser
```

```
            260                 265                 270
Leu Val Val Gly Gly Lys Leu Trp Gly Leu Val Ala Cys His His Tyr
            275                 280                 285

Leu Pro Arg Phe Met His Phe Glu Leu Arg Ala Ile Cys Glu Leu Leu
            290                 295                 300

Ala Glu Ala Ile Ala Thr Arg Ile Thr Ala Leu Glu Ser
305                 310                 315
```

<210> SEQ ID NO 11
<211> LENGTH: 311
<212> TYPE: PRT
<213> ORGANISM: Artificial Sequence
<220> FEATURE:
<223> OTHER INFORMATION: Artificial sequence based on bacterial sequence

<400> SEQUENCE: 11

```
Met Ala Arg Lys Val Asp Leu Thr Ser Cys Asp Arg Glu Pro Ile His
1               5                   10                  15

Ile Pro Gly Ser Ile Gln Pro Cys Gly Cys Leu Leu Ala Cys Asp Ala
            20                  25                  30

Gln Ala Val Arg Ile Thr Arg Ile Thr Glu Asn Ala Gly Ala Phe Phe
        35                  40                  45

Gly Arg Glu Thr Pro Arg Val Gly Glu Leu Leu Ala Asp Tyr Phe Gly
    50                  55                  60

Glu Thr Glu Ala His Ala Leu Arg Asn Ala Leu Ala Gln Ser Ser Asp
65                  70                  75                  80

Pro Lys Arg Pro Ala Leu Ile Phe Gly Trp Arg Asp Gly Leu Thr Gly
                85                  90                  95

Arg Thr Phe Asp Ile Ser Leu His Arg His Asp Gly Thr Ser Ile Ile
            100                 105                 110

Glu Phe Glu Pro Ala Ala Ala Glu Gln Ala Asp Asn Pro Leu Arg Leu
        115                 120                 125

Thr Arg Gln Ile Ile Ala Arg Thr Lys Glu Leu Lys Ser Leu Glu Glu
    130                 135                 140

Met Ala Ala Arg Val Pro Arg Tyr Leu Gln Ala Met Leu Gly Tyr His
145                 150                 155                 160

Arg Val Met Leu Tyr Arg Phe Ala Asp Asp Gly Ser Gly Met Val Ile
                165                 170                 175

Gly Glu Ala Lys Arg Ser Asp Leu Glu Ser Phe Leu Gly Gln His Phe
            180                 185                 190

Pro Ala Ser Leu Val Pro Gln Gln Ala Arg Leu Leu Tyr Leu Lys Asn
        195                 200                 205

Ala Ile Arg Val Val Ser Asp Ser Arg Gly Ile Ser Ser Arg Ile Val
    210                 215                 220

Pro Glu His Asp Ala Ser Gly Ala Ala Leu Asp Leu Ser Phe Ala His
225                 230                 235                 240

Leu Arg Ser Ile Ser Pro Cys His Leu Glu Phe Leu Arg Asn Met Gly
                245                 250                 255

Val Ser Ala Ser Met Ser Leu Ser Ile Ile Asp Gly Thr Leu Trp
            260                 265                 270

Gly Leu Ile Ile Cys His His Tyr Glu Pro Arg Ala Val Pro Met Ala
        275                 280                 285

Gln Arg Val Ala Ala Lys Arg Phe Ala Glu Arg Leu Ser Thr His Phe
    290                 295                 300

Thr Ala Ala His His Gln Arg
```

```
<210> SEQ ID NO 12
<211> LENGTH: 311
<212> TYPE: PRT
<213> ORGANISM: Artificial Sequence
<220> FEATURE:
<223> OTHER INFORMATION: Artificial sequence based on bacterial sequence

<400> SEQUENCE: 12

Met Ala Arg Lys Val Asp Leu Thr Ser Cys Asp Arg Glu Pro Ile His
1               5                   10                  15

Ile Pro Gly Ser Ile Gln Pro Cys Gly Cys Leu Leu Ala Cys Asp Ala
            20                  25                  30

Gln Ala Val Arg Ile Thr Arg Ile Thr Glu Asn Ala Gly Ala Phe Phe
        35                  40                  45

Gly Arg Glu Thr Pro Arg Val Gly Glu Leu Leu Ala Asp Tyr Phe Gly
    50                  55                  60

Glu Thr Glu Ala His Ala Leu Arg Asn Ala Leu Ala Gln Ser Ser Asp
65                  70                  75                  80

Pro Lys Arg Pro Ala Leu Ile Phe Gly Trp Arg Asp Gly Leu Thr Gly
                85                  90                  95

Arg Thr Phe Asp Ile Ser Leu His Arg His Asp Gly Thr Ser Ile Ile
            100                 105                 110

Glu Phe Glu Pro Ala Ala Ala Glu Gln Ala Asp Asn Pro Leu Arg Leu
        115                 120                 125

Thr Arg Gln Ile Ile Ala Arg Thr Lys Glu Leu Lys Ser Leu Glu Glu
    130                 135                 140

Met Ala Arg Val Pro Arg Tyr Leu Gln Ala Met Leu Gly Tyr His
145                 150                 155                 160

Arg Val Met Leu Tyr Arg Phe Ala Asp Asp Gly Ser Gly Lys Val Ile
                165                 170                 175

Gly Glu Ala Lys Arg Ser Asp Leu Glu Ser Phe Leu Gly Gln His Phe
            180                 185                 190

Pro Ala Ser Leu Val Pro Gln Gln Ala Arg Leu Leu Tyr Leu Lys Asn
        195                 200                 205

Ala Ile Arg Val Val Ser Asp Ser Arg Gly Ile Ser Ser Arg Ile Val
    210                 215                 220

Pro Glu His Asp Ala Ser Gly Ala Ala Leu Asp Leu Ser Phe Ala His
225                 230                 235                 240

Leu Arg Ser Ile Ser Pro Ile His Leu Glu Phe Leu Arg Asn Met Gly
                245                 250                 255

Val Ser Ala Ser Met Ser Leu Ser Ile Ile Asp Gly Thr Leu Trp
            260                 265                 270

Gly Leu Ile Ile Cys His His Tyr Glu Pro Arg Ala Val Pro Met Ala
        275                 280                 285

Gln Arg Val Ala Ala Lys Arg Phe Ala Glu Arg Leu Ser Thr His Phe
    290                 295                 300

Thr Ala Ala His His Gln Arg
305                 310

<210> SEQ ID NO 13
<211> LENGTH: 316
<212> TYPE: PRT
<213> ORGANISM: Artificial Sequence
<220> FEATURE:
<223> OTHER INFORMATION: Artificial sequence based on bacterial sequence
```

<400> SEQUENCE: 13

Met Ala Glu Gly Ser Val Ala Arg Gln Pro Asp Leu Leu Thr Cys Asp
1               5                   10                  15

Asp Glu Pro Ile His Ile Pro Gly Ala Ile Gln Pro His Gly Leu Leu
            20                  25                  30

Leu Ala Leu Ala Ala Asp Met Thr Ile Val Ala Gly Ser Asp Asn Leu
        35                  40                  45

Pro Glu Leu Thr Gly Leu Ala Ile Gly Ala Leu Ile Gly Arg Ser Ala
    50                  55                  60

Ala Asp Val Phe Asp Ser Glu Thr His Asn Arg Leu Thr Ile Ala Leu
65                  70                  75                  80

Ala Glu Pro Gly Ala Ala Val Gly Ala Pro Ile Thr Val Gly Phe Thr
                85                  90                  95

Met Arg Lys Asp Ala Gly Phe Ile Gly Ser Trp His Arg His Asp Gln
            100                 105                 110

Leu Ile Phe Leu Glu Leu Glu Pro Pro Gln Arg Asp Val Ala Glu Pro
        115                 120                 125

Gln Ala Phe Phe Arg Arg Thr Asn Ser Ala Ile Arg Arg Leu Gln Ala
    130                 135                 140

Ala Glu Thr Leu Glu Ser Ala Cys Ala Ala Ala Gln Glu Val Arg
145                 150                 155                 160

Lys Ile Thr Gly Phe Asp Arg Val Met Ile Tyr Arg Phe Ala Ser Asp
                165                 170                 175

Phe Ser Gly Val Val Ile Ala Glu Asp Arg Cys Ala Glu Val Glu Ser
            180                 185                 190

Lys Leu Gly Leu His Tyr Pro Ala Ser Ala Val Pro Ala Gln Ala Arg
        195                 200                 205

Arg Leu Tyr Thr Ile Asn Pro Val Arg Ile Ile Pro Asp Ile Asn Tyr
    210                 215                 220

Arg Pro Val Pro Val Thr Pro Asp Leu Asn Pro Val Thr Gly Arg Pro
225                 230                 235                 240

Ile Asp Leu Ser Phe Ala Ile Leu Arg Ser Val Ser Pro Cys His Leu
                245                 250                 255

Glu Phe Met Arg Asn Ile Gly Met His Gly Thr Met Ser Ile Ser Ile
            260                 265                 270

Leu Arg Gly Glu Arg Leu Trp Gly Leu Ile Val Cys His His Arg Thr
        275                 280                 285

Pro Tyr Tyr Val Asp Leu Asp Gly Arg Gln Ala Cys Lys Arg Val Ala
    290                 295                 300

Glu Arg Leu Ala Thr Gln Ile Gly Val Met Glu Glu
305                 310                 315

<210> SEQ ID NO 14
<211> LENGTH: 316
<212> TYPE: PRT
<213> ORGANISM: Artificial Sequence
<220> FEATURE:
<223> OTHER INFORMATION: Artificial sequence based on bacterial sequence

<400> SEQUENCE: 14

Met Ala Glu Gly Ser Val Ala Arg Gln Pro Asp Leu Leu Thr Cys Asp
1               5                   10                  15

Asp Glu Pro Ile His Ile Pro Gly Ala Ile Gln Pro His Gly Leu Leu
            20                  25                  30

```
Leu Ala Leu Ala Ala Asp Met Thr Ile Val Ala Gly Ser Asp Asn Leu
            35                  40                  45

Pro Glu Leu Thr Gly Leu Ala Ile Gly Ala Leu Ile Gly Arg Ser Ala
    50                  55                  60

Ala Asp Val Phe Asp Ser Glu Thr His Asn Arg Leu Thr Ile Ala Leu
65                  70                  75                  80

Ala Glu Pro Gly Ala Ala Val Gly Ala Pro Ile Thr Val Gly Phe Thr
                85                  90                  95

Met Arg Lys Asp Ala Gly Phe Ile Gly Ser Trp His Arg His Asp Gln
            100                 105                 110

Leu Ile Phe Leu Glu Leu Glu Pro Pro Gln Arg Asp Val Ala Glu Pro
        115                 120                 125

Gln Ala Phe Phe Arg Arg Thr Asn Ser Ala Ile Arg Arg Leu Gln Ala
    130                 135                 140

Ala Glu Thr Leu Glu Ser Ala Cys Ala Ala Ala Gln Glu Val Arg
145                 150                 155                 160

Lys Ile Thr Gly Phe Asp Arg Val Met Ile Tyr Arg Phe Ala Ser Asp
                165                 170                 175

Phe Ser Gly Glu Val Ile Ala Glu Asp Arg Cys Ala Glu Val Glu Ser
            180                 185                 190

Lys Leu Gly Leu His Tyr Pro Ala Ser Thr Val Pro Ala Gln Ala Arg
        195                 200                 205

Arg Leu Tyr Thr Ile Asn Pro Val Arg Ile Ile Pro Asp Ile Asn Tyr
    210                 215                 220

Arg Pro Val Pro Val Thr Pro Asp Leu Asn Pro Val Thr Gly Arg Pro
225                 230                 235                 240

Ile Asp Leu Ser Phe Ala Ile Leu Arg Ser Val Ser Pro Val His Leu
                245                 250                 255

Glu Phe Met Arg Asn Ile Gly Met His Gly Thr Met Ser Ile Ser Ile
            260                 265                 270

Leu Arg Gly Glu Arg Leu Trp Gly Leu Ile Val Cys His His Arg Thr
        275                 280                 285

Pro Tyr Tyr Val Asp Leu Asp Gly Arg Gln Ala Cys Lys Arg Val Ala
    290                 295                 300

Glu Arg Leu Ala Thr Gln Ile Gly Val Met Glu Glu
305                 310                 315

<210> SEQ ID NO 15
<211> LENGTH: 316
<212> TYPE: PRT
<213> ORGANISM: Artificial Sequence
<220> FEATURE:
<223> OTHER INFORMATION: Artificial sequence based on bacterial sequence

<400> SEQUENCE: 15

Met Ala Glu Gly Ser Val Ala Arg Gln Pro Asp Leu Leu Thr Cys Asp
1               5                   10                  15

Asp Glu Pro Ile His Ile Pro Gly Ala Ile Gln Pro His Gly Leu Leu
            20                  25                  30

Leu Ala Leu Ala Ala Asp Met Thr Ile Val Ala Gly Ser Asp Asn Leu
            35                  40                  45

Pro Glu Leu Thr Gly Leu Ala Ile Gly Ala Leu Ile Gly Arg Ser Ala
    50                  55                  60

Ala Asp Val Phe Asp Ser Glu Thr His Asn Arg Leu Thr Ile Ala Leu
65                  70                  75                  80
```

Ala Glu Pro Gly Ala Ala Val Gly Ala Pro Ile Thr Val Gly Phe Thr
                85                  90                  95

Met Arg Lys Asp Ala Gly Phe Ile Gly Ser Trp His Arg His Asp Gln
            100                 105                 110

Leu Ile Phe Leu Glu Leu Glu Pro Pro Gln Arg Asp Val Ala Glu Pro
        115                 120                 125

Gln Ala Phe Phe Arg Arg Thr Asn Ser Ala Ile Arg Arg Leu Gln Ala
    130                 135                 140

Ala Glu Thr Leu Glu Ser Ala Cys Ala Ala Ala Gln Glu Val Arg
145                 150                 155                 160

Lys Ile Thr Gly Phe Asp Arg Val Met Ile Tyr Arg Phe Ala Ser Asp
                165                 170                 175

Phe Ser Gly Ser Val Ile Ala Glu Asp Arg Cys Ala Glu Val Glu Ser
            180                 185                 190

Lys Leu Gly Leu His Tyr Pro Ala Ser Phe Ile Pro Ala Gln Ala Arg
        195                 200                 205

Arg Leu Tyr Thr Ile Asn Pro Val Arg Ile Ile Pro Asp Ile Asn Tyr
    210                 215                 220

Arg Pro Val Pro Val Thr Pro Asp Leu Asn Pro Val Thr Gly Arg Pro
225                 230                 235                 240

Ile Asp Leu Ser Phe Ala Ile Leu Arg Ser Val Ser Pro Asn His Leu
                245                 250                 255

Glu Phe Met Arg Asn Ile Gly Met His Gly Thr Met Ser Ile Ser Ile
            260                 265                 270

Leu Arg Gly Glu Arg Leu Trp Gly Leu Ile Val Cys His His Arg Thr
        275                 280                 285

Pro Tyr Tyr Val Asp Leu Asp Gly Arg Gln Ala Cys Lys Arg Val Ala
    290                 295                 300

Glu Arg Leu Ala Thr Gln Ile Gly Val Met Glu Glu
305                 310                 315

<210> SEQ ID NO 16
<211> LENGTH: 311
<212> TYPE: PRT
<213> ORGANISM: Artificial Sequence
<220> FEATURE:
<223> OTHER INFORMATION: Artificial sequence based on bacterial sequence

<400> SEQUENCE: 16

Met Pro Arg Lys Val Asp Leu Thr Ser Cys Asp Arg Glu Pro Ile His
1               5                   10                  15

Ile Pro Gly Ser Ile Gln Pro Cys Gly Cys Leu Leu Ala Cys Asp Ala
            20                  25                  30

Gln Ala Val Arg Ile Thr Arg Ile Ser Glu Asn Ala Gly Ala Phe Phe
        35                  40                  45

Gly Arg Glu Thr Pro Arg Val Gly Glu Leu Leu Ala Asp Tyr Phe Gly
    50                  55                  60

Glu Thr Glu Ala His Ala Leu Arg Asn Ala Leu Ala Gln Ser Ser Asp
65                  70                  75                  80

Pro Lys Arg Pro Ala Leu Ile Phe Gly Trp Arg Asp Gly Leu Thr Gly
                85                  90                  95

Arg Thr Phe Asp Ile Ser Leu His Arg His Asp Gly Thr Ser Ile Val
            100                 105                 110

Glu Phe Glu Pro Ala Ala Ala Asp Gln Ala Asp Asn Pro Leu Arg Leu
        115                 120                 125

```
Thr Arg Gln Ile Ile Ala Arg Thr Lys Glu Leu Lys Ser Leu Glu Glu
    130                 135                 140

Met Ala Ala Arg Val Pro Arg Tyr Leu Gln Ala Met Leu Gly Tyr His
145                 150                 155                 160

Arg Val Met Met Tyr Arg Phe Ala Asp Asp Gly Ser Gly Lys Val Ile
                165                 170                 175

Gly Glu Ala Lys Arg Ser Asp Leu Glu Ser Phe Leu Gly Gln His Phe
            180                 185                 190

Pro Ala Ser Asp Ile Pro Gln Gln Ala Arg Leu Leu Tyr Leu Lys Asn
        195                 200                 205

Ala Ile Arg Val Ile Ser Asp Ser Arg Gly Ile Ser Ser Arg Ile Val
210                 215                 220

Pro Glu Arg Asp Ala Ser Gly Ala Ala Leu Asp Leu Ser Phe Ala His
225                 230                 235                 240

Leu Arg Ser Val Ser Pro Ile His Leu Glu Tyr Leu Arg Asn Met Gly
                245                 250                 255

Val Ser Ala Ser Met Ser Leu Ser Ile Ile Ile Asp Gly Thr Leu Trp
            260                 265                 270

Gly Leu Ile Ala Cys His His Tyr Glu Pro Arg Ala Val Pro Met Ala
        275                 280                 285

Gln Arg Val Ala Ala Glu Met Phe Ala Asp Phe Phe Ser Leu His Phe
290                 295                 300

Thr Ala Ala His His Gln Arg
305                 310

<210> SEQ ID NO 17
<211> LENGTH: 316
<212> TYPE: PRT
<213> ORGANISM: Artificial Sequence
<220> FEATURE:
<223> OTHER INFORMATION: Artificial sequence based on bacterial sequence

<400> SEQUENCE: 17

Met Thr Glu Gly Ser Val Ala Arg Gln Pro Asp Leu Ser Thr Cys Asp
1               5                   10                  15

Asp Glu Pro Ile His Ile Pro Gly Ala Ile Gln Pro His Gly Leu Leu
            20                  25                  30

Leu Ala Leu Ala Ala Asp Met Thr Ile Val Ala Gly Ser Asp Asn Leu
        35                  40                  45

Pro Glu Leu Thr Gly Leu Ala Ile Gly Ala Leu Ile Gly Arg Ser Ala
    50                  55                  60

Ala Asp Val Phe Asp Ser Glu Thr His Asn Arg Leu Thr Ile Ala Leu
65                  70                  75                  80

Ala Glu Pro Gly Ala Ala Val Gly Ala Pro Ile Ala Val Gly Phe Thr
                85                  90                  95

Met Arg Lys Asp Ala Gly Phe Val Gly Ser Trp His Arg His Asp Gln
            100                 105                 110

Leu Val Phe Leu Glu Leu Glu Pro Pro Gln Arg Asp Val Ala Glu Pro
        115                 120                 125

Gln Ala Phe Phe Arg Arg Thr Asn Ser Ala Ile Arg Arg Leu Gln Ala
    130                 135                 140

Ala Glu Thr Leu Glu Ser Ala Cys Ala Ala Ala Gln Glu Val Arg
145                 150                 155                 160

Glu Ile Thr Gly Phe Asp Arg Val Met Ile Tyr Arg Phe Ala Ser Asp
                165                 170                 175
```

```
            Phe Ser Gly Glu Val Ile Ala Glu Asp Arg Cys Ala Glu Val Glu Ser
                        180                 185                 190

Tyr Leu Gly Leu His Phe Pro Ala Ser Asp Ile Pro Gln Ala Arg
                    195                 200                 205

Arg Leu Tyr Thr Ile Asn Pro Val Arg Ile Ile Pro Asp Ile Asn Tyr
                        210                 215                 220

Arg Pro Val Pro Val Thr Pro Asp Leu Asn Pro Val Thr Gly Arg Pro
            225                 230                 235                 240

Ile Asp Leu Ser Phe Ala Ile Leu Arg Ser Val Ser Pro Val His Leu
                            245                 250                 255

Glu Tyr Met Arg Asn Ile Gly Met His Gly Thr Met Ser Ile Ser Ile
                        260                 265                 270

Leu Arg Gly Glu Arg Leu Trp Gly Leu Ile Ala Cys His His Arg Lys
                    275                 280                 285

Pro Asn Tyr Val Asp Leu Asp Gly Arg Gln Ala Cys Glu Leu Val Ala
                        290                 295                 300

Gln Val Leu Ala Trp Gln Ile Gly Val Met Glu Glu
            305                 310                 315

<210> SEQ ID NO 18
            <211> LENGTH: 10
            <212> TYPE: DNA
            <213> ORGANISM: Artificial Sequence
            <220> FEATURE:
            <223> OTHER INFORMATION: Artificial sequence based on bacterial sequence

<400> SEQUENCE: 18 ggggsggggs                                                                    10

<210> SEQ ID NO 19
            <211> LENGTH: 11
            <212> TYPE: PRT
            <213> ORGANISM: Artificial Sequence
            <220> FEATURE:
            <223> OTHER INFORMATION: Artificial sequence based on bacterial sequence

<400> SEQUENCE: 19

Gly Gly Asp Glu Val Asp Gly Pro Val Ala Thr
            1               5                   10

<210> SEQ ID NO 20
            <211> LENGTH: 945
            <212> TYPE: DNA
            <213> ORGANISM: Artificial Sequence
            <220> FEATURE:
            <223> OTHER INFORMATION: Artificial sequence based on bacterial sequence

<400> SEQUENCE: 20
atggtagcag gtcatgcctc tgcagccccc gcattcggga ccgcctctca ttcgaattcc       60
gaacatgaag agatccacct cgccggctcg atccagccgc atggcgcgct tctggtcgtc      120
agcgaacatg atcatcgcgt catccaggcc agcgccaacg ccgcggaatt tctgaatctc      180
ggaagcgtac tcggcgttcc gctcgccgag atcgacggcg atctgttgat caagatcctg      240
ccgcatctcg atcccaccgc cgaaggcatg ccggtcgcgg tgcgctgccg gatcggcaat      300
ccctctacgg agtactgcgg tctgatgcat cggcctccgg aaggcgggct gatcatcgaa      360
ctcgaacgtg ccggccccgtc gatcgatctg tcaggcacgc tggcgccggc gctggagcgg      420
atccgcacgg cgggttcact gcgcgcgctg tgcgatgaca ccgtgctgct gtttcagcag      480
tgcaccggct acgaccgggt gatggtgtat cgtttcgatg agcaaggcca cggcctggta      540
```

```
ttctccgagt gccatgtgcc tgggctcgaa tcctatttcg gcaaccgcta tccgtcgtcg      600
actgtcccgc agatggcgcg gcagctgtac gtgcggcagc gcgtccgcgt gctggtcgac      660
gtcacctatc agccggtgcc gctggagccg cggctgtcgc cgctgaccgg gcgcgatctc      720
gacatgtcgg gctgcttcct gcgctcgatg tcgccgtgcc atctgcagtt cctgaaggac      780
atgggcgtgc gcgccaccct ggcggtgtcg ctggtggtcg gcggcaagct gtggggcctg      840
gttgtctgtc accattatct gccgcgcttc atccgtttcg agctgcgggc gatctgcaaa      900
cggctcgccg aaaggatcgc gacgcggatc accgcgcttg agagc                     945

<210> SEQ ID NO 21
<211> LENGTH: 945
<212> TYPE: DNA
<213> ORGANISM: Artificial Sequence
<220> FEATURE:
<223> OTHER INFORMATION: Artificial sequence based on bacterial sequence

<400> SEQUENCE: 21
atggtagcag gtcatgcctc tggcagcccc gcattcggga ccgcctctca ttcgaattgc       60
gaacatgaag agatccacct cgccggctcg atccagccgc atggcgcgct tctggtcgtc      120
agcgaacatg atcatcgcgt catccaggcc agcgccaacg ccgcggaatt tctgaatctc      180
ggaagcgtac tcggcgttcc gctcgccgag atcgacggcg atctgttgat caagatcctg      240
ccgcatctcg atcccaccgc cgaaggcatg ccggtcgcgg tgcgctgccg gatcggcaat      300
ccctctacgg agtactgcgg tctgatgcat cggcctccgg aaggcgggct gatcatcgaa      360
ctcgaacgtg ccggcccgtc gatcgatctg tcaggcacgc tggcgccggc gctggagcgg      420
atccgcacgg cgggttcact gcgcgcgctg tgcgatgaca ccgtgctgct gtttcagcag      480
tgcaccggct acgaccgggt gatggtgtat cgtttcgatg agcaaggcca cggcctggta      540
ttctccgagt gccatgtgcc tgggctcgaa tcctatttcg gcaaccgcta tccgtcgtcg      600
actgtcccgc agatggcgcg gcagctgtac gtgcggcagc gcgtccgcgt gctggtcgac      660
gtcacctatc agccggtgcc gctggagccg cggctgtcgc cgctgaccgg gcgcgatctc      720
gacatgtcgg gctgcttcct gcgctcgatg tcgccgtgcc atctgcagtt cctgaaggac      780
atgggcgtgc gcgccaccct ggcggtgtcg ctggtggtcg gcggcaagct gtggggcctg      840
gttgtctgtc accattatct gccgcgcttc atccgtttcg agctgcgggc gatctgcaaa      900
cggctcgccg aaaggatcgc gacgcggatc accgcgcttg agagc                     945

<210> SEQ ID NO 22
<211> LENGTH: 945
<212> TYPE: DNA
<213> ORGANISM: Artificial Sequence
<220> FEATURE:
<223> OTHER INFORMATION: Artificial sequence based on bacterial sequence

<400> SEQUENCE: 22
atggtagcag gtcatgcctc tggcagcccc gcattcggga ccgcctctca ttcgaattgc       60
gaacatgaag agatccacct cgccggctcg atccagccgc atggcgcgct tctggtcgtc      120
agcgaacatg atcatcgcgt catccaggcc agcgccaacg ccgcggaatt tctgaatctc      180
ggaagcgtac tcggcgttcc gctcgccgag atcgacggcg atctgttgat caagatcctg      240
ccgcatctcg atcccaccgc cgaaggcatg ccggtcgcgg tgcgctgccg gatcggcaat      300
ccctctacgg agtactgcgg tctgatgcat cggcctccgg aaggcgggct gatcatcgaa      360
```

```
ctcgaacgtg ccggcccgtc gatcgatctg tcaggcacgc tggcgccggc gctggagcgg      420
atccgcacgg cgggttcact gcgcgcgctg tgcgatgaca ccgtgctgct gtttcagcag      480
tgcaccggct acgaccgggt gatggtgtat cgtttcgatg agcaaggcca cggcctggta      540
ttctccgagt gccatgtgcc tgggctcgaa tcctatttcg caaccgcta tccgtcgtcg       600 ctggtcccgc agatggcgcg gcagctgtac gtgcggcagc gcgtccgcgt gctggtcgac      660
gtcacctatc agccggtgcc gctggagccg cggctgtcgc cgctgaccgg gcgcgatctc      720
gacatgtcgg gctgcttcct gcgctcgatg tcgccgatcc atctgcagtt cctgaaggac      780
atgggcgtgc gcgccaccct ggcggtgtcg ctggtggtcg gcggcaagct gtggggcctg      840
gttgtctgtc accattatct gccgcgcttc atccgtttcg agctgcgggc gatctgcaaa      900
cggctcgccg aaaggatcgc gacgcggatc accgcgcttg agagc                     945

<210> SEQ ID NO 23
<211> LENGTH: 945
<212> TYPE: DNA
<213> ORGANISM: Artificial Sequence
<220> FEATURE:
<223> OTHER INFORMATION: Artificial sequence based on bacterial sequence

<400> SEQUENCE: 23
atggtagcag gtcatgcctc tggcagcccc gcattcggga ccgcctctca ttcgaattgc       60
gaacatgaag agatccacct cgccggctcg atccagccgc atggcgcgct tctggtcgtc      120
agcgaacatg atcatcgcgt catccaggcc agcgccaacg ccgcggaatt tctgaatctc      180
ggaagcgtac tcggcgttcc gctcgccgag atcgacggcg atctgttgat caagatcctg      240
ccgcatctcg atcccaccgc cgaaggcatg ccggtcgcgg tgcgctgccg gatcggcaat      300
ccctctacgg agtactgcgg tctgatgcat cggcctccgg aaggcgggct gatcatcgaa      360
ctcgaacgtg ccggcccgtc gatcgatctg tcaggcacgc tggcgccggc gctggagcgg      420
atccgcacgg cgggttcact gcgcgcgctg tgcgatgaca ccgtgctgct gtttcagcag      480
tgcaccggct acgaccgggt gatggtgtat cgtttcgatg agcaaggcca cggcctggta      540
ttctccgagt gccatgtgcc tgggctcgaa tcctatttcg caaccgcta tccgtcgtcg       600 ttcatcccgc agatggcgcg gcagctgtac gtgcggcagc gcgtccgcgt gctggtcgac      660
gtcacctatc agccggtgcc gctggagccg cggctgtcgc cgctgaccgg gcgcgatctc      720
gacatgtcgg gctgcttcct gcgctcgatg tcgccgatcc atctgcagtt cctgaaggac      780
atgggcgtgc gcgccaccct ggcggtgtcg ctggtggtcg gcggcaagct gtggggcctg      840
gttgtctgtc accattatct gccgcgcttc atccgtttcg agctgcgggc gatctgcaaa      900
cggctcgccg aaaggatcgc gacgcggatc accgcgcttg agagc                     945

<210> SEQ ID NO 24
<211> LENGTH: 378
<212> TYPE: DNA
<213> ORGANISM: Artificial Sequence
<220> FEATURE:
<223> OTHER INFORMATION: Artificial sequence based on bacterial sequence

<400> SEQUENCE: 24
atggtagcag gtcatgcctc tggcagcccc gcattcggga ccgcctctca ttcgaattgc       60
gaacatgaag agatccacct cgccggctcg atccagccgc atggcgcgct tctggtcgtc      120
agcgaacatg atcatcgcgt catccaggcc agcgccaacg ccgcggaatt tctgaatctc      180
ggaagcgtac tcggcgttcc gctcgccgag atcgacggcg atctgttgat caagatcctg      240
```

-continued

| | |
|---|---|
| ccgcatctcg atcccaccgc cgaaggcatg ccggtcgcgg tgcgctgccg gatcggcaat | 300 |
| ccctctacgg agtactgcgg tctgatgcat cggcctccgg aaggcgggct gatcatcgaa | 360 |
| ctcgaacgtg ccggcccg | 378 |

<210> SEQ ID NO 25
<211> LENGTH: 378
<212> TYPE: DNA
<213> ORGANISM: Artificial Sequence
<220> FEATURE:
<223> OTHER INFORMATION: Artificial sequence based on bacterial sequence

<400> SEQUENCE: 25

| | |
|---|---|
| atggtagcag gtcatgcctc tggcagcccc gcattcggga ccgcctctca ttcgaattcc | 60 |
| gaacatgaag agatccacct cgccggctcg atccagccgc atggcgcgct tctggtcgtc | 120 |
| agcgaacatg atcatcgcgt catccaggcc agcgccaacg ccgcggaatt tctgaatctc | 180 |
| ggaagcgtac tcggcgttcc gctcgccgag atcgacggcg atctgttgat caagatcctg | 240 |
| ccgcatctcg atcccaccgc cgaaggcatg ccggtcgcgg tgcgctgccg gatcggcaat | 300 |
| ccctctacgg agtactgcgg tctgatgcat cggcctccgg aaggcgggct gatcatcgaa | 360 |
| ctcgaacgtg ccggcccg | 378 |

<210> SEQ ID NO 26
<211> LENGTH: 579
<212> TYPE: DNA
<213> ORGANISM: Artificial Sequence
<220> FEATURE:
<223> OTHER INFORMATION: Artificial sequence based on bacterial sequence

<400> SEQUENCE: 26

| | |
|---|---|
| cgtgccggcc cgtcgatcga tctgtcaggc acgctggcgc cggcgctgga gcggatccgc | 60 |
| acggcgggtt cactgcgcgc gctgtgcgat gacaccgtgc tgctgtttca gcagtgcacc | 120 |
| ggctacgacc gggtgatggt gtatcgtttc gatgagcaag gccacggcct ggtattctcc | 180 |
| gagtgccatg tgcctgggct cgaatcctat ttcggcaacc gctatccgtc gtcgactgtc | 240 |
| ccgcagatgg cgcggcagct gtacgtgcgg cagcgcgtcc gcgtgctggt cgacgtcacc | 300 |
| tatcagccgg tgccgctgga gccgcggctg tcgccgctga ccgggcgcga tctcgacatg | 360 |
| tcgggctgct cctgcgctc gatgtcgccg tgccatctgc agttcctgaa ggacatgggc | 420 |
| gtgcgcgcca ccctggcggt gtcgctggtg gtcggcggca gctgtggggg cctggttgtc | 480 |
| tgtcaccatt atctgccgcg cttcatccgt ttcgagctgc gggcgatctg caaacggctc | 540 |
| gccgaaagga tcgcgacgcg gatcaccgcg cttgagagc | 579 |

<210> SEQ ID NO 27
<211> LENGTH: 579
<212> TYPE: DNA
<213> ORGANISM: Artificial Sequence
<220> FEATURE:
<223> OTHER INFORMATION: Artificial sequence based on bacterial sequence

<400> SEQUENCE: 27

| | |
|---|---|
| cgtgccggcc cgtcgatcga tctgtcaggc acgctggcgc cggcgctgga gcggatccgc | 60 |
| acggcgggtt cactgcgcgc gctgtgcgat gacaccgtgc tgctgtttca gcagtgcacc | 120 |
| ggctacgacc gggtgatggt gtatcgtttc gatgagcaag gccacggcct ggtattctcc | 180 |
| gagtgccatg tgcctgggct cgaatcctat ttcggcaacc gctatccgtc gtcgctggtc | 240 |

```
ccgcagatgg cgcggcagct gtacgtgcgg cagcgcgtcc gcgtgctggt cgacgtcacc    300
tatcagccgg tgccgctgga gccgcggctg tcgccgctga ccgggcgcga tctcgacatg    360
tcgggctgct tcctgcgctc gatgtcgccg atccatctgc agttcctgaa ggacatgggc    420
gtgcgcgcca cctggcggt gtcgctggtg gtcggcggca agctgtgggg cctggttgtc    480
tgtcaccatt atctgccgcg cttcatccgt ttcgagctgc gggcgatctg caaacggctc    540
gccgaaagga tcgcgacgcg gatcaccgcg cttgagagc                            579

<210> SEQ ID NO 28
<211> LENGTH: 579
<212> TYPE: DNA
<213> ORGANISM: Artificial Sequence
<220> FEATURE:
<223> OTHER INFORMATION: Artificial sequence based on bacterial sequence

<400> SEQUENCE: 28
cgtgccggcc cgtcgatcga tctgtcaggc acgctggcgc cggcgctgga gcggatccgc     60
acggcgggtt cactgcgcgc gctgtgcgat gacaccgtgc tgctgtttca gcagtgcacc    120
ggctacgacc gggtgatggt gtatcgtttc gatgagcaag ccacggcct ggtattctcc     180 gagtgccatg tgcctgggct cgaatcctat ttcggcaacc gctatccgtc gtcgttcatc    240
ccgcagatgg cgcggcagct gtacgtgcgg cagcgcgtcc gcgtgctggt cgacgtcacc    300
tatcagccgg tgccgctgga gccgcggctg tcgccgctga ccgggcgcga tctcgacatg    360
tcgggctgct tcctgcgctc gatgtcgccg atccatctgc agttcctgaa ggacatgggc    420
gtgcgcgcca cctggcggt gtcgctggtg gtcggcggca agctgtgggg cctggttgtc    480
tgtcaccatt atctgccgcg cttcatccgt ttcgagctgc gggcgatctg caaacggctc    540
gccgaaagga tcgcgacgcg gatcaccgcg cttgagagc                            579

<210> SEQ ID NO 29
<211> LENGTH: 951
<212> TYPE: DNA
<213> ORGANISM: Artificial Sequence
<220> FEATURE:
<223> OTHER INFORMATION: Artificial sequence based on bacterial sequence

<400> SEQUENCE: 29
atggctagcg tggcaggtca tgcctctggc agccccgcat tcgggaccgc cgatctttcg     60
aattgcgaac gtgaagagat ccacctcgcc ggctcgatcc agccgcatgg cgcgcttctg    120
gtcgtcagcg agccggatca tcgcatcatc caggccagcg ccaacgccgc ggaatttctg    180
aatctcggaa gcgtgctcgg cgttccgctc gccgagatcg acggcgatct gttgatcaag    240
atcctgccgc atctcgatcc caccgccgaa ggcatgccgg tcgcggtgcg ctgccggatc    300
ggcaatccct ccacggagta cgacggtctg atgcatcggc ctccggaagg cgggctgatc    360
atcgagctcg aacgtgccgg cccgccgatc gatctgtccg gcacgctggc gccggcgctg    420
gagcggatcc gcacggcggg ctcgctgcgc gcgctgtgcg atgacaccgc gctgctgttt    480
cagcagtgca ccggctacga ccgggtgatg gtgtatcgct tcgacgagca gggccacggc    540
gaagtgttct ccgagcgcca cgtgcccggg ctcgaatcct atttcggcaa ccgctatccg    600
tcgtcggaca ttccgcagat ggcgcggcgg ctgtacgagc ggcagcgcgt ccgcgtgctg    660
gtcgacgtca gctatcagcc ggtgccgctg gagccgcggc tgtcgccgct gaccgggcgc    720
gatctcgaca tgtcgggctg cttcctgcgc tcgatgtcgc cgatccatct gcagtacctg    780
aagaacatgg gcgtgcgcgc caccctggtg gtgtcgctgg tggtcggcgg caagctgtgg    840
```

```
ggcctggttg cctgtcatca ttatctgccg cgcttcatgc atttcgagct gcgggcgatc      900
tgcgaactgc tcgccgaagc gatcgcgacg cggatcaccg cgcttgagag c               951
```

<210> SEQ ID NO 30
<211> LENGTH: 936
<212> TYPE: DNA
<213> ORGANISM: Artificial Sequence
<220> FEATURE:
<223> OTHER INFORMATION: Artificial sequence based on bacterial sequence

<400> SEQUENCE: 30

```
atggcgcgta aggtcgatct cacctcctgc gatcgcgagc cgatccacat ccccggcagc      60
attcagccgt gcggctgcct gctagcctgc gacgcgcagg cggtgcggat cacgcgcatt     120
acggaaaatg ccgcgcgtt ctttggacgc gaaactccgc gggtcggtga gctactcgcc      180
gattacttcg gcgagaccga agcccatgcg ctgcgcaacg cactggcgca gtcctccgat     240
ccaaagcgac cggcgctgat cttcggttgg cgcgacggcc tgaccggccg caccttcgac     300
atctcactgc atcgccatga cggtacatcg atcatcgagt tcgagcctgc ggcggccgaa     360
caggccgaca atccgctgcg gctgacgcgg cagatcatcg cgcgcaccaa agaactgaag     420
tcgctcgaag agatggccgc acgggtgccg cgctatctgc aggcgatgct cggctatcac     480
cgcgtgatgt tgtaccgctt cgcggacgac ggctccggga tggtgatcgg cgaggcgaag     540
cgcagcgacc tcgagagctt tctcggtcag cactttccgg cgtcgctggt cccgcagcag     600
gcgcggctac tgtacttgaa gaacgcgatc cgcgtggtct cggattcgcg cggcatcagc     660
agccggatcg tgcccgagca cgacgcctcc ggcgccgcgc tcgatctgtc gttcgcgcac     720
ctgcgcagca tctcgccctg ccatctcgaa tttctgcgga acatgggcgt cagcgcctcg     780
atgtcgctgt cgatcatcat tgacggcacg ctatggggat tgatcatctg tcatcattac     840
gagccgcgtg ccgtgccgat ggcgcagcgc gtcgcggcca agaggttcgc cgagaggtta     900
tcgactcact tcaccgccgc ccaccaccaa cgctaa                                936
```

<210> SEQ ID NO 31
<211> LENGTH: 936
<212> TYPE: DNA
<213> ORGANISM: Artificial Sequence
<220> FEATURE:
<223> OTHER INFORMATION: Artificial sequence based on bacterial sequence

<400> SEQUENCE: 31

```
atggcgcgta aggtcgatct cacctcctgc gatcgcgagc cgatccacat ccccggcagc      60
attcagccgt gcggctgcct gctagcctgc gacgcgcagg cggtgcggat cacgcgcatt     120
acggaaaatg ccgcgcgtt ctttggacgc gaaactccgc gggtcggtga gctactcgcc      180
gattacttcg gcgagaccga agcccatgcg ctgcgcaacg cactggcgca gtcctccgat     240
ccaaagcgac cggcgctgat cttcggttgg cgcgacggcc tgaccggccg caccttcgac     300
atctcactgc atcgccatga cggtacatcg atcatcgagt tcgagcctgc ggcggccgaa     360
caggccgaca atccgctgcg gctgacgcgg cagatcatcg cgcgcaccaa agaactgaag     420
tcgctcgaag agatggccgc acgggtgccg cgctatctgc aggcgatgct cggctatcac     480
cgcgtgatgt tgtaccgctt cgcggacgac ggctccggca agtgatcgg cgaggcgaag     540 cgcagcgacc tcgagagctt tctcggtcag cactttccgg cgtcgctggt cccgcagcag     600
gcgcggctac tgtacttgaa gaacgcgatc cgcgtggtct cggattcgcg cggcatcagc     660
```

| | |
|---|---|
| agccggatcg tgcccgagca cgacgcctcc ggcgccgcgc ttgatctgtc gttcgcgcac | 720 |
| ctgcgcagca tctcgcctat ccatctcgaa tttctgcgga acatgggcgt cagcgcctcg | 780 |
| atgtcgctgt cgatcatcat tgacggcacg ctatggggat tgatcatctg tcatcattac | 840 |
| gagccgcgtg ccgtgccgat ggcgcagcgc gtcgcggcca agaggttcgc cgagaggtta | 900 |
| tcgactcact tcaccgccgc ccaccaccaa cgctaa | 936 |

<210> SEQ ID NO 32
<211> LENGTH: 951
<212> TYPE: DNA
<213> ORGANISM: Artificial Sequence
<220> FEATURE:
<223> OTHER INFORMATION: Artificial sequence based on bacterial sequence

<400> SEQUENCE: 32

| | |
|---|---|
| atggcggaag gatccgtcgc caggcagcct gacctcttga cctgcgacga tgagccgatc | 60 |
| catatccccg gtgccatcca accgcatgga ctgctgctcg ccctcgccgc cgacatgacg | 120 |
| atcgttgccg gcagcgacaa ccttcccgaa ctcaccggac tggcgatcgg cgccctgatc | 180 |
| ggccgctctg cggccgatgt cttcgactcg gagacgcaca accgtctgac gatcgccttg | 240 |
| gccgagcccg ggcggccgt cggagcaccg atcactgtcg gcttcacgat gcgaaaggac | 300 |
| gcaggcttca tcggctcctg gcatcgccat gatcagctca tcttcctcga gctcgagcct | 360 |
| ccccagcggg acgtcgccga gccgcaggcg ttcttccgcc gcaccaacag cgccatccgc | 420 |
| cgcctgcagg ccgccgaaac cttggaaagc gcctgcgccg ccgcggcgca agaggtgcgg | 480 |
| aagattaccg gcttcgatcg ggtgatgatc tatcgcttcg cctccgactt cagcggggtg | 540 |
| gtgatcgcag aggatcgatg cgccgaggtc gagtcaaaac taggcctgca ctatcctgcc | 600 |
| tcagcggtgc cggcgcaggc ccgtcggctc tataccatca acccggtacg gatcattccc | 660 |
| gatatcaatt atcggccggt gccggtcacc ccagacctca atccggtcac cgggcggccg | 720 |
| attgatctta gcttcgccat cctgcgcagc gtctcgccct gccatttgga gttcatgcgc | 780 |
| aacataggca tgcacggcac gatgtcgatc tcgattttgc gcggcgagcg actgtgggga | 840 |
| ttgatcgttt gccatcaccg aacgccgtac tacgtcgatc tcgatggccg ccaagcctgc | 900 |
| aagagggtcg ccgagaggct ggccactcag atcggcgtga tggaagagtg a | 951 |

<210> SEQ ID NO 33
<211> LENGTH: 951
<212> TYPE: DNA
<213> ORGANISM: Artificial Sequence
<220> FEATURE:
<223> OTHER INFORMATION: Artificial sequence based on bacterial sequence

<400> SEQUENCE: 33

| | |
|---|---|
| atggcggaag gatccgtcgc caggcagcct gacctcttga cctgcgacga tgagccgatc | 60 |
| catatccccg gtgccatcca accgcatgga ctgctgctcg ccctcgccgc cgacatgacg | 120 |
| atcgttgccg gcagcgacaa ccttcccgaa ctcaccggac tggcgatcgg cgccctgatc | 180 |
| ggccgctctg cggccgatgt cttcgactcg gagacgcaca accgtctgac gatcgccttg | 240 |
| gccgagcccg ggcggccgt cggagcaccg atcactgtcg gcttcacgat gcgaaaggac | 300 |
| gcaggcttca tcggctcctg gcatcgccat gatcagctca tcttcctcga gctcgagcct | 360 |
| ccccagcggg acgtcgccga gccgcaggcg ttcttccgcc gcaccaacag cgccatccgc | 420 |
| cgcctgcagg ccgccgaaac cttggaaagc gcctgcgccg ccgcggcgca agaggtgcgg | 480 |
| aagattaccg gcttcgatcg ggtgatgatc tatcgcttcg cctccgactt cagcggcgaa | 540 |

```
gtgatcgcag aggatcggtg cgccgaggtc gagtcaaaac taggcctgca ctatcctgcc    600
tcaaccgtgc cggcgcaggc ccgtcggctc tataccatca acccggtacg gatcattccc    660
gatatcaatt atcggccggt gccggtcacc ccagacctca atccggtcac cgggcggccg    720
attgatctta gcttcgccat cctgcgcagc gtctcgcccg tccatctgga attcatgcgc    780
aacataggca tgcacggcac gatgtcgatc tcgattttgc gcggcgagcg actgtgggga    840
ttgatcgttt gccatcaccg aacgccgtac tacgtcgatc tcgatggccg ccaagcctgc    900
aagagggtcg ccgagaggct ggccactcag atcggcgtga tggaagagtg a             951
```

<210> SEQ ID NO 34
<211> LENGTH: 951
<212> TYPE: DNA
<213> ORGANISM: Artificial Sequence
<220> FEATURE:
<223> OTHER INFORMATION: Artificial sequence based on bacterial sequence

<400> SEQUENCE: 34

```
atggcggaag gatccgtcgc caggcagcct gacctcttga cctgcgacga tgagccgatc     60
catatccccg gtgccatcca accgcatgga ctgctgctcg ccctcgccgc cgacatgacg    120
atcgttgccg gcagcgacaa ccttcccgaa ctcaccggac tggcgatcgg cgccctgatc    180
ggccgctctg cggccgatgt cttcgactcg gagacgcaca accgtctgac gatcgccttg    240
gccgagcccg ggcggccgt cggagcaccg atcactgtcg gcttcacgat gcgaaaggac    300
gcaggcttca tcggctcctg gcatcgccat gatcagctca tcttcctgga gctggagcct    360
ccccagcggg acgtcgccga ccgcaggcg ttcttccgcc gcaccaacag cgccatccgc     420
cgcctgcagg ccgccgaaac cttggaaagc gcctgcgccg ccgcggcgca agaggtgcgg    480
aagattaccg gcttcgatcg ggtgatgatc tatcgcttcg cctccgactt cagcgggtcc    540
gtgatcgcag aggatcggtg cgccgaggtc gagtcaaaac taggcctgca ctatcctgcc    600
tcattcatcc cggcgcaggc ccgtcggctc tataccatca acccggtacg gatcattccc    660
gatatcaatt atcggccggt gccggtcacc ccagacctca atccggtcac cgggcggccg    720
attgatctta gcttcgccat cctgcgcagc gtctcgccca ccatctgga gttcatgcgc    780 aacataggca tgcacggcac gatgtcgatc tcgattttgc gcggcgagcg actgtgggga    840
ttgatcgttt gccatcaccg aacgccgtac tacgtcgatc tcgatggccg ccaagcctgc    900
aagagggtcg ccgagaggct ggccactcag atcggcgtga tggaagagtg a             951
```

<210> SEQ ID NO 35
<211> LENGTH: 933
<212> TYPE: DNA
<213> ORGANISM: Artificial Sequence
<220> FEATURE:
<223> OTHER INFORMATION: Artificial sequence based on bacterial sequence

<400> SEQUENCE: 35

```
atgccgcgta aggtcgatct cacctcctgc gatcgcgagc cgatccacat ccccggcagc     60
attcagccgt gcggctgcct gctggcctgc gacgcgcagg cggtgcggat cacgcgcatt    120
tcggaaaatg ccggcgcgtt ctttggacgc gaaactccgc gggtcggtga gctactcgcc    180
gattacttcg gcgagaccga agcccatgcg ctgcgcaacg cactggcgca gtcctccgat    240
ccaaagcggc cggcgctgat cttcggttgg cgcgacggcc tgaccggccg caccttcgac    300
atctcgctgc atcgccatga cggtacatcg atcgtcgaat tcgagcctgc ggcggccgat    360
```

```
caggccgaca atccgctgcg gctgacgcgg cagatcatcg cgcgcaccaa agaactgaag      420
tcgctcgagg agatggccgc acgggtgccg cgctatctgc aggcgatgct cggctatcac      480
cgcgtgatga tgtaccgctt cgcggacgac ggctccggca aagtgatcgg cgaggcgaag      540
cgcagcgacc tcgagagctt tctcggtcag cactttccgg cgtcggacat cccgcagcag      600
gcgcggctgc tgtacttgaa gaacgcgatc cgcgtgatct cggattcgcg cggcatcagc      660
agccggatcg tgcccgagcg cgacgcctcc ggcgccgcgc tcgatctgtc gttcgcgcac      720
ctgcgcagcg tctcgcccat ccatctcgaa tatctgcgga acatgggcgt cagcgcctcg      780
atgtcgctgt cgatcatcat tgacggcacg ctatggggat tgatcgcctg tcatcattac      840
gagccgcgtg ccgtgccgat ggcgcagcgc gtcgccgccg aaatgttcgc cgacttcttc      900
tcgctgcact tcaccgccgc ccaccaccaa cgc                                   933

<210> SEQ ID NO 36
<211> LENGTH: 950
<212> TYPE: DNA
<213> ORGANISM: Artificial Sequence
<220> FEATURE:
<223> OTHER INFORMATION: Artificial sequence based on bacterial sequence

<400> SEQUENCE: 36
atgacagaag gatccgtcgc caggcagcct gacctctcga cctgcgacga tgagccgatc       60
catatccccg gtgccatcca accgcatgga ctgctgctcg ccctcgccgc cgacatgacg      120
atcgttgccg gcagcgacaa ccttcccgaa ctcaccggac tggcgatcgg cgccctgatc      180
ggccgctctg cggccgatgt cttcgactcg gagacgcaca accgtctgac gatcgccttg      240
gccgagcccg gggcggccgt cggagcaccg atcgctgtcg gcttcacgat gcgaaaggac      300
gcaggcttcg tcggctcctg gcatcgccat gatcagctcg tcttcctcga gctcgagcct      360
ccccagcggg acgtcgccga gccgcaggcg ttcttccgcc gcaccaacag cgccatccgc      420
cgcctgcagg ccgccgaaac cttggaaagc gcctgcgccg ccgcggcgca agaggtgcgg      480
gagattaccg gcttcgatcg ggtgatgatc tatcgcttcg cctccgactt cagcggcgaa      540
gtgatcgcag aggatcggtg cgccgaggtc gagtcatatc taggcctgca ctttcctgcc      600
tcagacatcc cggcgcaggc ccgtcggctc tataccatca acccggtacg gatcattccc      660
gatatcaatt atcggccggt gccggtcacc ccagacctca atccggtcac cgggcggccg      720
attgatctta gcttcgccat cctgcgcagc gtctcgcccg tccatctgga atacatgcgc      780
aacatcggca tgcacggcac gatgtcgatc tcgattttgc gcggcgagcg actgtgggga      840
ttgatcgcct gccatcaccg aaagccgaac tacgtcgatc tcgatggccg ccaagcctgc      900
gagctagtcg cccaggttct ggcctggcag atcggcgtga tggaagagca                950
```